United States Patent [19]
Häbich et al.

[11] Patent Number: 4,863,916
[45] Date of Patent: Sep. 5, 1989

[54] SUBSTITUTED 6-HYDROXYMETHYL-CARBAPENEM ANTIBIOTICS

[75] Inventors: Dieter Häbich, Wuppertal, Fed. Rep. of Germany; Wolfgang Hartwig, Chicago, Ill.; Karl G. Metzger, Wuppertal; Hans-Joachim Zeiler, Velbert, both of Fed. Rep. of Germany

[73] Assignee: Bayer Aktiengesellschaft, Leverkusen, Fed. Rep. of Germany

[21] Appl. No.: 47,371

[22] Filed: May 6, 1987

[30] Foreign Application Priority Data

May 26, 1986 [DE] Fed. Rep. of Germany ....... 3617626

[51] Int. Cl.[4] .................... C07D 487/04; A61K 31/40
[52] U.S. Cl. ..................................... 514/210; 540/350
[58] Field of Search ......................... 540/350; 514/210

[56] References Cited
FOREIGN PATENT DOCUMENTS 0017992 10/1980 European Pat. Off. .
0181702 5/1986 European Pat. Off. .

Primary Examiner—Robert Gerstl
Attorney, Agent, or Firm—Sprung Horn Kramer & Woods

[57] ABSTRACT

Substituted 6-hydroxymethyl-carbapenem antibiotics of the formula

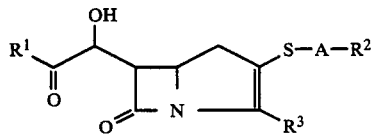

in which
$R^1$ is $-OR^4$,

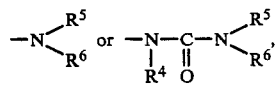

A is a direct bond, or an alkylene and/or cycloalkylene radical,
$R^2$ is a group of the formula

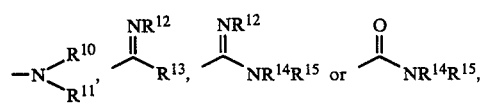

an aryl or heterocyclic radical,

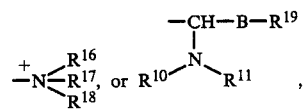

$R^3$ is a COOH radical, or salt or ester thereof.

12 Claims, No Drawings

SUBSTITUTED 6-HYDROXYMETHYL-CARBAPENEM ANTIBIOTICS

The present invention relates to substituted 6-hydroxymethyl-carbapenem antibiotics, process for the preparation thereof, and the use thereof as medicaments.

It is known that carbapenems of the thienamycin type [cf. T. Kametani, Heterocycles, 17, 463 (1982)] are distinguished by a good antibacterial action, which also includes methicillin- and oxacillin-resistant Staphylococci. Since the discovery of thienamycin, a large number of derivatives have been synthesized, but most of these compounds are unstable, as the substance alone, towards degradation by liver peptidases, specifically dehydropeptidase (I) (DHP-I) [cf. H. Kropp et al., Antimicrob. Agents., Chemother. 22, 62 (1982)]. This enzyme is responsible for the metabolic deactivation of carbapenems and for the formation of toxic metabolites.

In addition, it is known that the instability of this class of compounds towards dehydropeptidase (I) can be partially suppressed by the addition of a dipeptidase inhibitor [cf. Drugs of the Future 9, 227 (1984)], by the incorporation of a 1-β-methyl group [cf. D. H. Shih et al., Heterocycles 21, 29 (1984); Drugs of the Future 9, 336 (1984)], and by varying the side chains in the 2 position [cf. B. G. Christensen et al., in A. G. Brown and S. M. Roberts (eds), Recent Advances in the Chemistry of β-Lactam Antibiotics, Royal Society of Chemistry, Special Publication No. 52, page 86 (1985)].

The present invention relates to substituted 6-hydroxymethyl-carbapenem antibiotics of the general formula (I)

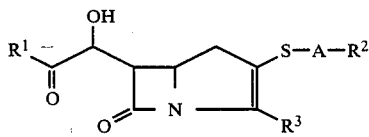

in which
$R^1$ represents a group of the formula $-OR^4$,

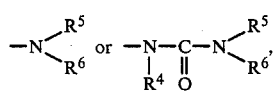

in which $R^4$, $R^5$ and $R^6$ are identical or different and denote hydrogen or $C_6-C_{12}$-aryl which is optionally up to trisubstituted, identically or differently, by nitro, hydroxyl, cyano, halogen, trifluoromethyl, trifluoromethoxy, $C_1-C_6$-alkyl or $C_1-C_6$-alkoxy, or denote $C_1-C_{12}$-alkyl, $C_2-C_{12}$-alkenyl or $C_3-C_8$-cycloalkyl, these radicals being optionally polysubstituted, identically or differently by $C_1-C_4$-alkoxy, halogen, hydroxyl, cyano and/or phenyl, where this phenyl radical may again carry up to three identical or different substituents from the series comprising $C_1-C_4$-alkyl, $C_1-C_4$-alkoxy, nitro, cyano, hydroxyl or halogen, and/or by a group of the formula $-CO_2R^7$ and/or $-NR^8R^9$,
in which
$R^7$ represents hydrogen, phenyl, benzyl, $C_1-C_8$-alkyl or $C_2-C_6$-alkenyl, and $R^8$ and $R^9$ are identical or different and represent hydrogen, $C_1-C_6$-alkyl, phenyl, benzyl or an amino-protecting group, A represents a direct bond or
represents a $C_1-C_{12}$-alkylene or $C_2-C_{12}$-alkenylene chain which is optionally interrupted in the chain by an oxygen atom or a sulphur atom, or
represents cycloalkylene having 3 to 8 carbon atoms, cycloalkylene-alkylene or alkylenecycloalkylene in each case having 3 to 8 carbon atoms in the cycloalkylene part and 1 to 8 carbon atoms in the alkylene chain, or
alkylene-cycloalkylene-alkylene having 3 to 8 carbon atoms in the cycloalkyl part and 1 to 8 carbon atoms in each alkylene part, $R^2$ (a) represents a group of the formula

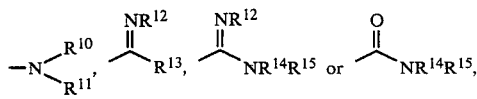

in which
$R^{10}$ denotes hydrogen, $C_1-C_{10}$-alkyl, $C_6-C_{12}$-aryl or $C_7-C_{14}$-aralkyl,
$R^{11}$ represents hydrogen, $C_1-C_{10}$-alkyl, $C_6-C_{12}$-aryl, $C_7-C_{14}$-aralkyl, $C_1-C_{10}$-alkylsulphonyl, $C_6-C_{12}$-arylsulphonyl, $C_7-C_{14}$-aralkylsulphonyl, an amino-protecting group, or a group of the formula

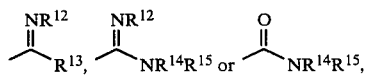

and
$R^{12}$, $R^{13}$, $R^{14}$ and $R^{15}$ are identical or different and denote hydrogen, $C_1-C_{10}$-alkyl, $C_6-C_{12}$ aryl or $C_7-C_{14}$-aralkyl,
or
(b) represents a $C_6-C_{12}$-aryl radical which is optionally up to trisubstituted, identically or differently,
(c) represents a 5- to 7-membered heterocycle, having up to 4 heteroatoms from the series comprising O, S and/or N, which may be substituted and to which 2 further rings may be fused,
(d) represents a group of the formula

in which
$R^{16}$, $R^{17}$ and $R^{18}$ are identical or different and denote a substituted or unsubstituted alkyl radical or a mono- or bicyclic optionally substituted carbocyclic or heterocyclic ring, or
$R^{16}$ represents an optionally substituted alkyl radical or a mono- or bicyclic substituted or unsubstituted carbocyclic or heterocyclic ring, and
$R^{17}$ and $R^{18}$, together with the nitrogen atom, form an optionally substituted mono- or polycyclic ring which may be saturated or unsaturated and which may contain oxygen, sulphur and/or nitrogen as further heteroatoms,
$R^{16}$, $R^{17}$ and $R^{18}$, together with the nitrogen atom, form a bridged, optionally substituted, polycyclic ring which may be saturated or unsaturated and which may contain oxygen, sulphur and/or nitrogen as further heteroatoms,
in which the

group denotes a nitrogen-containing and positively charged heterocyclic 5- to 6-membered ring which is bonded via nitrogen, which may contain a total of up to 4 heteroatoms from the group comprising nitrogen, oxygen and/or sulphur, to which up to 2 further rings may be fused, and which may optionally be substituted, (e) represents $C_1$-$C_8$-alkoxycarbonylmethyl, carboxymethyl, hydroxymethyl or a group of the formula

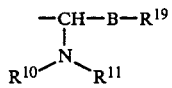

in which
$R^{10}$ and $R^{11}$ have the abovementioned meaning,
B denotes a methylene or carbonyl group, and
$R^{19}$ denotes hydroxyl, amino, $C_1$-$C_6$-alkylamino, di-$C_1$-$C_6$-alkylamino, $C_6$-$C_{12}$-arylamino, $C_7$-$C_{14}$-aralkylamino, $C_2$-$C_7$-acylamino or pyridylamino and
$R^3$ represents a carboxyl group of the formula $COOR^{20}$,
in which
$R^{20}$ denotes hydrogen, a carboxyl-protecting group, or an ester radical which can be cleaved off in vivo, or
represents $COO^-$ if $R^2$ represents a radical having positive charge,
and the salts thereof.

In the context of the abovementioned definition, amino-protecting group generally represents an amino-protecting group which is conventional in β-lactam chemistry. Examples which may preferably be mentioned are: vinyl, allyl, tert-butoxycarbonyl, benzyl, benzyloxycarbonyl, 2-nitrobenzyl, 4-nitrobenzyl, 2-nitrobenzyloxycarbonyl, 2-nitrobenzyloxycarbonyl, 4-methoxybenzyloxycarbonyl, formyl, benzoyl, acetyl, ethylcarbonyl, chloroacetyl, trichloroacetyl, trifluoroacetyl, methyloxycarbonyl, allyloxycarbonyl, trimethylsilyl, triethylsilyl, triphenylsilyl, tert-butyl-dimethylsilyl, methyldiphenylsilyl, 2,4-dimethoxybenzyl, 2,4-dimethoxybenzyloxycarbonyl, 4-methoxybenzyl, 4-methoxymethyloxuyphenyl, bis-(4-methoxyphenyl)-methyl, tert-butoxycarbonylmethyl, allyloxycarbonylmethyl, methoxymethyl, methylthiomethyl, methoxyethoxymethyl, [2-(trimethylsilyl)ethoxy]methyl, 2-(methylthiomethoxy)ethoxycarbonyl or tetrahydropyranyl.

In the context of the abovementioned definition, carboxyl-protecting group represents the carboxyl-protecting groups which are conventional in β-lactam chemistry. Examples which may preferably be mentioned are groups which can easily be cleaved off, such as: methyl, ethyl, tert-butyl, decyl, 2-chloroethyl, 2,2,2-trichloroethyl, cyanoethyl, diphenylmethyl, triphenylmethyl, acetoxymethyl, allyl, benzyl, 4-methoxyphenyl, 4-nitrobenzyl, 2-nitrobenzyl, 4-methoxybenzyl, 2,4-dimethoxybenzyl, trimethylsilylethyl, tert-butyl-dimethyl-silylethyl, trimethylsilyl, tert-butyl-dimethylsilyl, acetonyl, 1-phenoxyethyl or 2-methyl-2-propenyl.

If $R^{20}$ represents an ester radical which can easily be cleaved off in vivo, pharmaceutically acceptable ester radicals which are easily hydrolyzed in vivo to form free carboxyl groups ($R^{20}$=H) are meant here.

Such ester radicals $R^{20}$ are well known in the penicillin area. In most cases, they improve the absorption properties of the β-lactam compound. In addition, the radical $R^{20}$ should be of a type such that it confers pharmaceutically acceptable properties on a compound of the formula (I) and liberates pharmaceutically acceptable fragments on cleavage in vivo.

Examples of such $R^{20}$ groups are contained in DE-OS No.(German Published Specification) No. 2,517,316. Preferred ester groups $R^{20}$ are those of the following formulae:

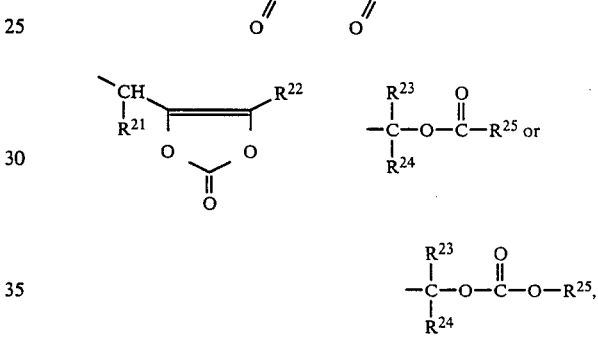

in which
$R^{21}$ and $R^{22}$ are identical or different and denote hydrogen, phenyl or $C_1$-$C_4$-alkyl, preferably methyl,
$R^{23}$ and $R^{24}$ are identical or different and denote hydrogen, or $C_1$-$C_4$-alkyl, preferably methyl, and
$R^{25}$ denotes $C_1$-$C_6$-alkyl, preferably $C_1$-$C_4$-alkyl.

When $R^2$ represents $C_6$-$C_{12}$-aryl which is optionally up to trisubstituted, then it preferably represents phenyl which is up to trisubstituted, preferably up to disubstituted, by halogen, hydroxyl, mercapto, $C_1$-$C_8$-alkyl, $C_1$-$C_8$-alkylthio, $C_1$-$C_8$-alkoxy, cyano, nitro, trifluoromethyl, trifluoromethoxy, trifluoromethylthio, carboxyl, $C_1$-$C_8$-alkoxycarbonyl, sulpho, $C_1$-$C_8$-alkylsulphonyl, phenylsulphonyl, tolylsulphonyl, carbamoyl, sulphamoyl, $C_1$-$C_8$-aminoalkyl, $C_1$-$C_8$-hydroxyalkyl, $C_1$-$C_8$-cyanoalkyl, $C_1$-$C_8$-carboxyalkyl, $C_1$-$C_6$-alkoxycarbonyl-$C_1$-$C_8$-alkyl or a group of the formula

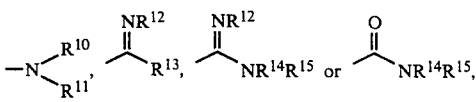

in which
$R^{10}$ denotes hydrogen, $C_1$-$C_{10}$-alkyl, $C_6$-$C_{12}$-aryl or $C_7$-$C_{14}$-aralkyl,
$R^{11}$ denotes hydrogen, $C_1$-$C_{10}$-alkyl, $C_6$-$C_{12}$-aryl, $C_7$-$C_{14}$-aralkyl, $C_1$-$C_{10}$-alkylsulphonyl, $C_6$-$C_{12}$-arylsulphonyl, $C_7$-$C_{14}$-aralkylsulphonyl, an amino-protecting group, or a group of the formula

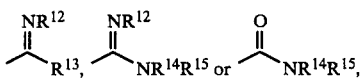

and $R^{12}$, $R^{13}$, $R^{14}$ and $R^{15}$ are identical or different and denote hydrogen, $C_1$-$C_{10}$-alkyl, $C_6$-$C_{12}$-aryl or $C_7$-$C_{14}$-aralkyl.

In the context of the abovementioned definition, alkyl covers straight-chain and branched alkyl radicals, preferably having the specified number of carbon atoms.

In the context of the abovementioned definition, halogen represents fluorine, chlorine, bromine or iodine.

Preferred compounds of the general formula (I),
in which
$R^1$, A and $R^3$ have the meaning specified in claim 1, and
$R^2$ (a) represents a group of the formula

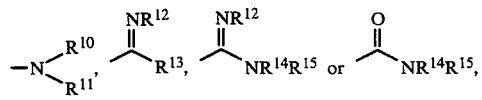

in which
$R^{10}$ denotes hydrogen, $C_1$-$C_8$-alkyl, phenyl or benzyl,
$R^{11}$ denotes hydrogen, $C_1$-$C_8$-alkyl, phenyl, benzyl, $C_1$-$C_8$-alkylsulphonyl, phenylsulphonyl, benzylsulphonyl, an amino-protecting group, or a group of the formula

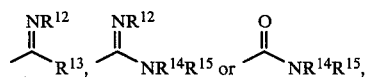

and
$R^{12}$, $R^{13}$, $R^{14}$ and $R^{15}$ are identical or different and denote hydrogen, $C_1$-$C_8$-alkyl, phenyl or benzyl,
(b) represents phenyl which is optionally up to disubstituted by fluorine, chlorine, bromine, hydroxyl, mercapto, $C_1$-$C_4$-alkyl, $C_1$-$C_4$-alkoxy, $C_1$-$C_4$-alkylthio, cyano, nitro, trifluoromethyl, trifluoromethoxy, carboxyl, $C_1$-$C_4$-alkoxycarbonyl, sulpho, $C_1$-$C_4$-alkylsulphonyl, phenylsulphonyl, tolylsulphonyl, carbamoyl, sulphamoyl, $C_1$-$C_4$-aminoalkyl, $C_1$-$C_4$-hydroxyalkyl, $C_1$-$C_4$-cyanoalkyl, $C_1$-$C_4$-carboxyalkyl, $C_1$-$C_4$-alkoxycarbonyl, $C_1$-$C_4$-alkyl or a group of the formula

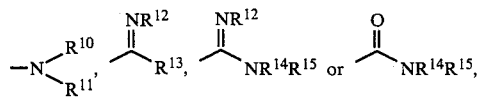

in which
$R^{10}$, $R^{11}$, $R^{12}$, $R^{13}$, $R^{14}$ and $R^{15}$ have the abovementioned meaning,
(c) represents a 5- to 7-membered heterocycle, having up to 4 heteroatoms from the series comprising O, S and/or N, which may be saturated or unsaturated, which may be bound to the radical A via a nitrogen or via a carbon atom, which may be up to disubstituted on the ring carbon atoms or on the ring nitrogen atoms, it being possible for a quaternary nitrogen atom to be present, and to which up to 2 further carbocyclic or heterocyclic rings may be fused,
(d) represents a group of the formula

in which
$R^{16}$, $R^{17}$ and $R^{18}$ are identical or different from one another and represent an optionally substituted $C_1$-$C_6$-alkyl radical or a 3- to 7-membered, optionally substituted ring,
$R^{16}$ has the above meaning and
$R^{17}$ and $R^{18}$, together with the nitrogen atom, form a 3- to 7-membered ring which may be saturated or unsaturated, which may contain 1 or 2 further heteroatoms from the series comprising O, S and/or N, and which may be mono- or polysubstituted, preferably mono- to trisubstituted, identically or differently, it being possible for these substituents to be located on further nitrogen atoms contained in the ring,
or in which the group of the formula

denotes a nitrogen-containing and positively charged five- or six-membered ring which is bonded via nitrogen, which contains up to a total of 4 heteroatoms from the series comprising O, S and/or N, to which up to 2 further rings may be fused, and which may optionally be substituted, or
(e) represents $C_1$-$C_4$-alkoxycarbonylmethyl, carboxymethyl, hydroxymethyl, or a group of the formula

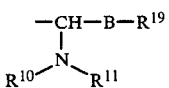

in which
$R^{10}$ and $R^{11}$ have the abovementioned meaning,
B denotes a methylene or a carbonyl group and
$R^{19}$ denotes hydroxyl, amino, $C_1$-$C_4$-alkylamino, di-$C_1$-$C_4$-alkylamino, phenylamino, benzylamino, acetylamino, benzoylamino or pyridylamino,
and the salts thereof.

When $R^2$ represents (c) a 5- to 7-membered heterocycle having up to 4 heteroatoms, then it preferably represents a radical of the formula

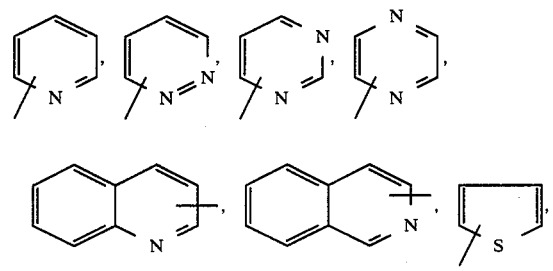

-continued

[chemical structures]

in which
R²⁶ denotes hydrogen, C₁–C₆-alkyl or phenyl,
R²⁷ denotes C₁–C₆-alkyl, C₁–C₆-alkylcarbonyl or a group of the formula

in which
R¹² and R¹³ are identical or different and represent hydrogen, C₁–C₆-alkyl, phenyl or benzyl, and
R²⁸ denotes C₁–C₆-alkyl or phenyl,
which is optionally substituted by C₁–C₄-alkoxy, hydroxyl, amino, C₁–C₄-alkylamino, di-C₁–C₄-alkylamino, acetylamino, benzylamino, formylimidoamino, acetylimidoamino, guanidino, formylamino, halogen, phenyl, benzyl, carbamoyl, sulphamoyl, C₁–C₄-alkyl, C₁–C₄-aminoalkyl, C₁–C₄-hydroxyalkyl, C₁–C₄-alkylamino-C₁–C₄-alkyl, di-C₁–C₄-alkylamino-C₁–C₄-alkyl, formylimidoamino-C₁–C₄-alkyl, acetylimidoamino-C₁–C₄-alkyl, guanidino-C₁–C₄-alkyl or C₁–C₄-carbamoylalkyl.

When R¹⁶ and/or R¹⁷ and/or R¹⁸ represent a substituted alkyl radical, then they preferably represent those having 1 or 2 substituents, preferably hydroxyl, carboxyl, C₁–C₆-alkoxycarbonyl, formyl or C₁–C₆-alkylcarbonyl whose carbonyl groups may also be present in ketalized form, carbamoyl, sulpho, cyano, nitro, halogen, amino, C₁–C₆-alkylamino, di-C₁–C₆-alkylamino, C₁–C₆-alkylcarbonylamino, C₁–C₆-alkoxy, C₁–C₆-alkylthio, C₁–C₆-alkylsulphonyl, phenyl, pyridyl, pyrimidyl or C₃–C₆-cycloalkyl.

When R¹⁶ and/or R¹⁷ and/or R¹⁸ represent a saturated or unsaturated, optionally substituted 3- to 7-membered ring, then they preferably represent a carbocyclic or heterocyclic ring, which may contain up to 3 heteroatoms from the series comprising oxygen, nitrogen and/or sulphur.

If this ring is substituted, preferably it is by one or two substituents, preferably C₁–C₆-alkyl, hydroxyl, C₁–C₆-hydroxy-alkyl, carboxyl, C₁–C₆-alkoxycarbonyl, formyl or C₁–C₆-alkylcarbonyl whose carbonyl groups may also be present in ketalized form, carbamoyl, sulpho, cyano, nitro, halogen, amino, C₁–C₆-alkylamino, di-C₁–C₆-alkylamino, C₁–C₆-alkylcarbonylamino, C₁–C₆-alkoxy, C₁–C₆-alkylthio, C₁–C₆-alkylsulphonyl, phenyl, pyrimidyl or pyridyl.

When R¹⁷ and R¹⁸, together with the nitrogen atom, form an optionally substituted heterocyclic ring, then they preferably represent a 3- to 7-membered ring which may contain one or two double bonds or a carbonyl group and which may contain up to 2 further heteroatoms from the series comprising oxygen, nitrogen or sulphur and to which a further 5- to 6-membered ring may be fused.

When the heterocyclic ring formed by R¹⁷ and R¹⁸ together with the nitrogen atom is substituted, preferably it is by one or two substituents, preferably C₁–C₆-alkyl, hydroxyl, C₁–C₆-hydroxyalkyl, C₁–C₆-aminoalkyl, carboxyl, C₁–C₆-alkoxycarbonyl, formyl or C₁–C₆-alkylcarbonyl whose carbonyl groups may also be present in ketalized form, carbamoyl, sulpho, cyano, nitro, halogen, amino, C₁–C₆-alkylamino, di-C₁–C₆-alkylamino, C₁–C₆-alkylcarbonylamino, C₁–C₆-alkoxy, C₁–C₆-alkylthio, C₁–C₆-alkylsulphonyl, phenylsulphonyl, sulphamoyl, di-C₁–C₆-alkylaminosulphonyl, phenyl, pyridyl or pyrimidyl. If this heterocyclic ring contains a nitrogen atom as further heteroatom, the substituents mentioned may also be bonded to this nitrogen atom.

When the

group represents a nitrogen-containing and positively charged 5- or 6-membered ring which is bonded via nitrogen, which contains a total of up to 4 heteroatoms from the series comprising O, S and/or N, to which up to 2 further rings may be fused, and which may optionally be substituted, then it preferably represents an optionally substituted ring of the formula

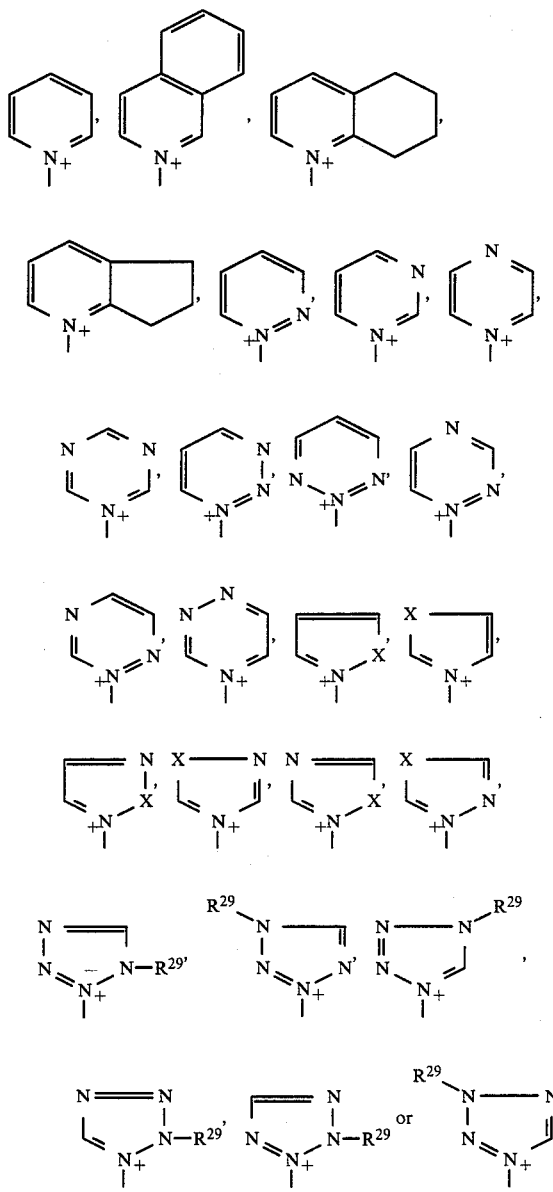

in which
X represents O, S, $CH_2$ or $NR^{29}$, and
$R^{29}$ represents phenyl or $C_1$-$C_4$-alkyl which is optionally substituted by amino, hydroxyl, halogen, $C_1$-$C_4$-alkylamino, di-$C_1$-$C_4$-alkylamino or acetylamino.

If these rings are substituted, preferably it is up to twofold, identically or differently, by substituents from the following series: $C_1$-$C_4$-alkyl, $C_1$-$C_4$-hydroxyalkyl, $C_1$-$C_4$-carboxyalkyl, $C_1$-$C_4$-alkoxycarbonyl-$C_1$-$C_4$-alkyl, $C_1$-$C_4$-formylalkyl, $C_1$-$C_4$-alkylcarbonyl-$C_1$-$C_4$-alkyl, $C_1$-$C_4$-carbamoylalkyl, $C_1$-$C_4$-sulphoalkyl, $C_1$-$C_4$-alkoxy-$C_1$-$C_4$-alkyl, $C_1$-$C_4$-alkylthio-$C_1$-$C_4$-alkyl, $C_1$-$C_4$-alkylsulphonyl-$C_1$-$C_4$-alkyl, $C_1$-$C_3$-cyanoalkyl, trifluoromethyl, trifluoromethoxy, $C_3$-$C_4$-alkenyl, $C_3$-$C_6$-cycloalkyl, $C_3$-$C_6$-cycloalkylmethyl, $C_1$-$C_4$-alkoxy, phenyloxy, amino, $C_1$-$C_4$-alkylamino, di-$C_1$-$C_4$-alkylamino, $C_1$-$C_4$-alkylcarbonylamino, formylamino, formylimidoamino, acetylimidoamino, guanidino, carbamoyl, N-$C_1$-$C_4$-alkylcarbamoyl, N,N-di-$C_1$-$C_4$-alkylcarbamoyl, sulphamoyl, di-$C_1$-$C_4$-alkylaminosulphonyl, cyano, hydroxyl, halogen, $C_1$-$C_4$-alkylthio, $C_1$-$C_4$-alkylsulphonyl, phenyl, benzyl, formyl, carboxy or $C_1$-$C_4$-alkoxycarbonyl.

Particularly preferred compounds of the general formula (I) are those
in which $R^1$ represents a group of the formula

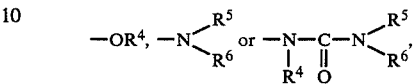

in which $R^4$, $R^5$ and $R^6$ are identical or different and denote hydrogen or phenyl which is optionally substituted by nitro, hydroxyl, fluorine, chlorine, methyl or methoxy, or denote $C_1$-$C_8$-alkyl, $C_2$-$C_4$-alkenyl, cyclopentyl or cyclohexyl, these radicals being optionally up to disubstituted, identically or differently, by methoxy, fluorine, chlorine, bromine, hydroxyl, cyano or phenyl, where this phenyl radical ma8y again carry up to two identical or different substituents from the series comprising methyl, methoxy, nitro, hydroxyl or chlorine, and/or by a group of the formula —$CO_2R^7$ or —$NR^8R^9$,
in which
$R^7$ represents hydrogen, benzyl, $C_1$-$C_6$-alkyl, or $C_2$-$C_4$-alkenyl, and
$R^8$ and $R^9$ are identical or different and represent hydrogen, $C_1$-$C_4$-alkyl, or an amino-protecting group from the series comprising allyl, tert-butoxycarbonyl, benzyl, benzyloxycarbonyl, 4-nitrobenzyl, 4-nitrobenzyloxycarbonyl, 4-methoxybenzyloxycarbonyl, 4-methoxyphenyl, 2,4-dimethoxybenzyl, 2-nitrobenzyloxycarbonyl, tert-butyl-dimethyl-silyl, methyldiphenylsilyl, trimethylsilyl, acetyl, trifluoroacetyl, formyl or trichloroacetyl,
A represents a direct bond or straight-chain or branched $C_1$-$C_8$-alkylene, straight-chain or branched $C_2$-$C_8$-alkylene having up to two double bonds, cyclopentylene, cyclohexylene, cyclopentylene-$C_1$-$C_4$-alkylene, cyclohexylene-$C_1$-$C_4$-alkylene, $C_1$-$C_4$-alkylene-cyclopentylene or $C_1$-$C_4$-alkylene-cyclohexylene,
$R^2$ (a) represents a group of the formula

in which
$R^{10}$ denotes hydrogen, $C_1$-$C_6$-alkyl, phenyl or benzyl,
$R^{11}$ denotes hydrogen, $C_1$-$C_6$-alkyl, phenyl, benzyl, $C_1$-$C_4$-alkylsulphonyl, phenylsulphonyl, benzylsulphonyl, an amino-protecting group from the series comprising allyl, tert-butoxycarbonyl, benzyl, benzyloxycarbonyl, 4-nitrobenzyl, 4-nitrobenzyloxycarbonyl, 4-methoxybenzyloxycarbonyl, formyl, acetyl, trichloroacetyl, 4-methoxyphenyl, 4-methoxybenzyl, 2,4-dimethoxybenzyl, 2-nitrobenzyloxycarbonyl, tert-butyl-dimethylsilyl, methyldiphenylsilyl, trimethylsilyl or trifluoroacetyl, or a gorup of the formula

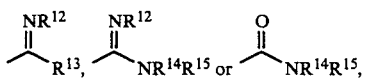

in which
R$^{12}$, R$^{13}$, R$^{14}$ and R$^{15}$ are identical or different and represent hydrogen, C$_1$–C$_6$-alkyl, phenyl or benzyl, or R$^2$ (b) represents phenyl which is optionally substituted by fluorine, chlorine, hydroxyl, methoxy, cyano, trifluoromethyl, carbamoyl, sulphamoyl, C$_1$–C$_4$-alkyl, cyanomethyl, carboxymethyl, hydroxymethyl, aminomethyl or a group of the formula

in which R$^{10}$ and R$^{11}$ have the abovementioned meaning, or

R$^2$ (c) represents a radical of the formula

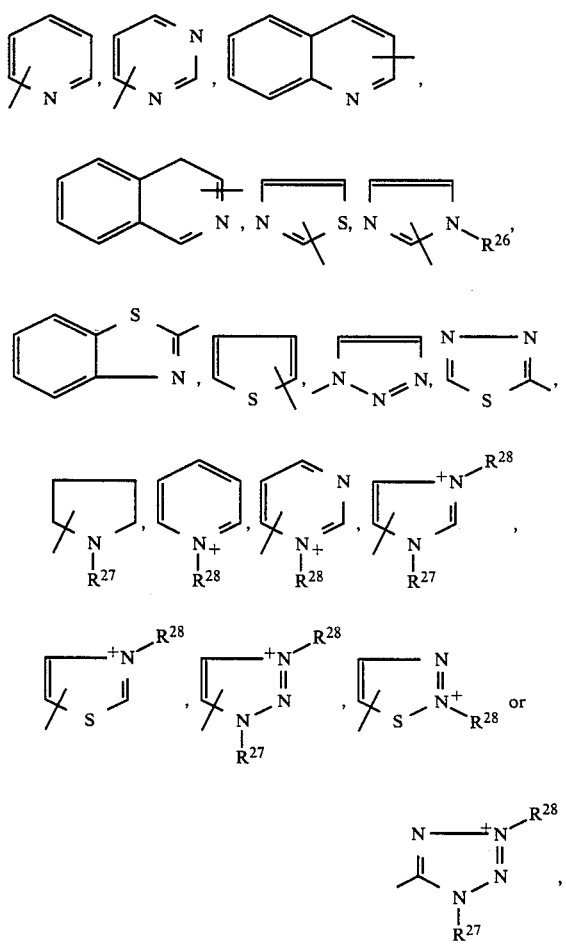

in which
R$^{26}$ denotes hydrogen, C$_1$–C$_4$-alkyl or phenyl,
R$^{27}$ denotes C$_1$–C$_4$-alkyl, C$_1$–C$_4$-alkylcarbonyl or a group of the formula

in which
R$^{12}$ and R$^{13}$ are identical or different and have the abovementioned meaning, and
R$^{28}$ denotes C$_1$–C$_4$-alkyl or phenyl,
which is optionally substituted by methoxy, amino, methylamino, dimethylamino, acetylamino, formylamino, formylimidoamino, acetylimidoamino, guanidino, fluorine, chlorine, carbamoyl, sulphamoyl, C$_1$–C$_4$-alkyl, amino-C$_1$–C$_2$-alkyl, methylamino-C$_1$–C$_2$-alkyl, dimethylamino-C$_1$–C$_2$-alkyl, hydroxy-C$_1$–C$_2$-alkyl or carbamoyl-C$_1$–C$_2$-alkyl, or R$^2$ (d) represents a group of the formula

in which R$^{16}$, R$^{17}$ and R$^{18}$ are identical or different and represent a C$_1$–C$_6$-alkyl radical which is optionally substituted by hydroxyl, amino, carboxyl, cyano, nitro, methoxy, methoxycarbonyl, fluorine, chlorine, cyclopropyl, cyclopentyl, cyclohexyl, phenyl or pyridyl,
or in which
R$^{16}$ has the abovementioned meaning, and
R$^{17}$ and R$^{18}$, together, represent the radical of the formula

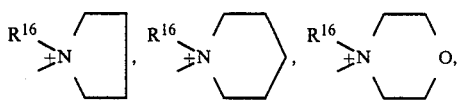

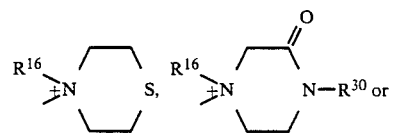

in which R$^{30}$ represents C$_1$–C$_4$-alkyl, carbamoyl, formyl, acetylimido, formylimido, sulphamoyl, C$_1$–C$_4$-hydroxyalkyl, C$_1$–C$_4$-aminoalkyl or C$_1$–C$_4$-alkylsulphonyl, which is optionally substituted by C$_1$–C$_4$-alkyl, C$_1$–C$_4$-hydroxyalkyl, C$_1$–C$_4$-aminoalkyl, carboxyl, methoxycarbonyl, formyl, acetyl, carbamoyl, amino, methylamino, dimethylamino, acetylamino, C$_1$–C$_4$-alkoxy, C$_1$–C$_4$-alkylsulphonyl or dimethylaminosulphonyl, or in which the

group represents a radical of the formula

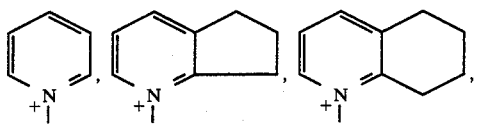

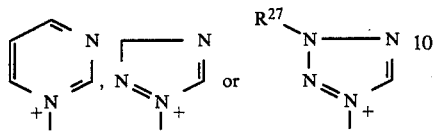

in which $R^{27}$ has the abovementioned meaning, which is optionally substituted by $C_1$-$C_4$-alkyl, hydroxymethyl, carboxymethyl, methoxycarbonylmethyl, formylmethyl, carbamoylmethyl, methoxymethyl, methylsulphonylmethyl, cyanomethyl, trifluoromethyl, cyclopropyl, $C_1$-$C_4$-alkoxy, amino, methylamino, dimethylamino, acetylamino, formylamino, formylimidoamino, acetylimidoamino, guanidino, carbamoyl, N-methylcarbamoyl, dimethylcarbamoyl, dimethylaminosulphonyl, cyano, hydroxyl, fluorine or chlorine, or $R^2$ (e) represents $C_1$-$C_4$-alkoxycarbonylmethyl, carboxymethyl, hydroxymethyl or a group of the formula

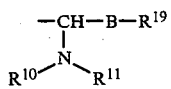

in which $R^{10}$ and $R^{11}$ have the abovementioned meaning,

B denotes a methylene or carbonyl gorup, and $R^{19}$ denotes hydroxyl, amino, $C_1$-$C_4$-alkylamino, di-$C_1$-$C_4$-alkylamino, phenylamino, benzylamino, acetylamino or pyridylamino, and $R^3$ represents a carboxyl group of the formula $COOR^{20}$, in which $R^{20}$ represents hydrogen, methyl, ethyl, tert-butyl, 2,2,2-trichloroethyl, allyl, acetylmethyl, 4-nitrobenzyl, 2-nitrobenzyl, 4-methoxybenzyl, benzyl, trimethylsilylethyl or a radical of the formula

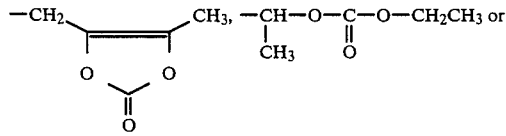

or $R^3$ represents $COO^-$ if $R^2$ represents a radical having a positive charge, and the salts thereof.

Very particularly preferred compounds of the general formula (I) are those in which $R^1$ represents a group of the formula

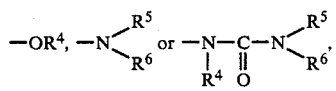

in which $R^4$, $R^5$ and $R^6$ are identical or different and denote hydrogen, allyl or straight-chain or branched $C_1$-$C_4$-alkyl, cyclopentyl or cyclohexyl, the alkyl radical being optionally substituted by chlorine, phenyl, nitrophenyl, amino, tert-butyloxycarbonylamino, benzyloxycarbonylamino, acetylamino and/or a group of the formula $-COOR^7$, in which $R^7$ represents hydrogen, $C_1$-$C_4$-alkyl, allyl or 4-nitrobenzyl, A represents a direct bond or represents straight-chain or branched $C_1$-$C_4$-alkylene or $C_2$-$C_4$-alkylene, or represents cyclohexylene, cyclopentylene, cyclopentylenemethyl, cyclohexylenemethyl, methylenecyclopentylene or methylenecyclohexylene, $R^2$ (a) represents a group of the formula

in which $R^{10}$ denotes hydrogen, $C_1$-$C_4$-alkyl or phenyl, $R^{11}$ denotes hydrogen, $C_1$-$C_4$-alkyl, phenyl, tert-butoxycarbonyl, benzyloxycarbonyl, acetyl, ethylcarbonyl or a group of the formula

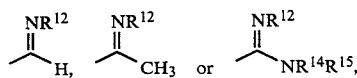

in which $R^{12}$, $R^{14}$ and $R^{15}$ are identical or different and represent hydrogen, methyl or phenyl, or $R^2$ (b) represents phenyl which is optionally substituted by hydroxyl, methyl, methoxy, hydroxymethyl amino, formylimidoamino, acetylimidoamino, guanidino or aminomethyl, or $R^2$ (c) represents a group of the formula

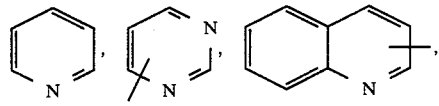

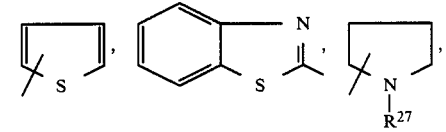

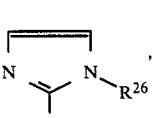 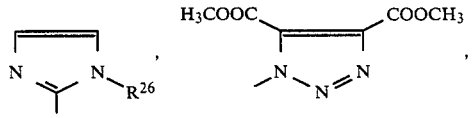

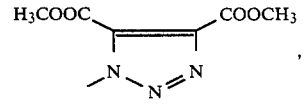

-continued

, 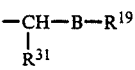, 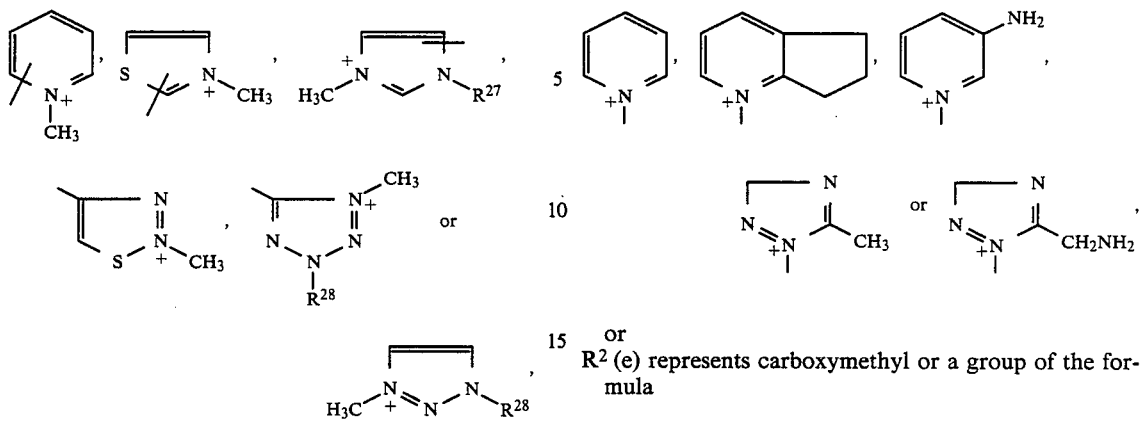

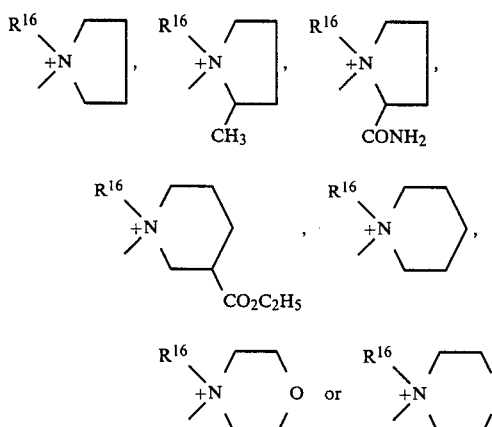

or

in which
R²⁶ represents hydrogen, methyl or phenyl,
R²⁷ represents acetyl, formylimido or acetylimido, and
R²⁸ represents methyl, or phenyl
which is optionally substituted by methyl, amino, formylimidoamino, acetylimidoamino, guanidino or aminomethyl,
R² (d) represents a group of the formula $$-\overset{+}{N}\begin{smallmatrix}R^{16}\\R^{17}\\R^{18}\end{smallmatrix}$$

in which
R¹⁶, R¹⁷ and R¹⁸ are identical or different and denote a $C_1$-$C_4$-alkyl radical which is optionally substituted by hydroxyl, amino, phenyl or pyridyl, or
R¹⁶ denotes methyl or ethyl, and
R¹⁷ and R¹⁸, together, represent a group of the formula

[cyclic ammonium structures with R¹⁶, including pyrrolidinium, N-methylpyrrolidinium, pyrrolidinium-CONH₂, piperidinium-CO₂C₂H₅, piperidinium, morpholinium, piperazinium N-R³⁰]

in which R³⁰ represents $C_1$-$C_4$-alkyl, carbamoyl, formyl, $C_1$-$C_4$-hydroxyalkyl or methylsulphonyl, or the $$-\overset{+}{N}\begin{smallmatrix}R^{16}\\R^{17}\\R^{18}\end{smallmatrix}$$

group represents a group of the formula or
R² (e) represents carboxymethyl or a group of the formula $$-\underset{R^{31}}{\overset{|}{CH}}-B-R^{19}$$

in which
B denotes a methylene or carbonyl group,
R¹⁹ denotes hydroxyl, amino, methylamino, dimethylamino, acetylamino or pyridylamino, and
R³¹ denotes amino, methylamino, dimethylamino or acetylamino, and
R³ represents a carboxyl group of the formula COOR²⁰,
in which
R²⁰ denotes hydrogen, allyl, 4-nitrobenzyl or 4-methoxybenzyl, or
represents COO⁻ if R² represents a radical having a positive charge,
or the salts thereof.

Especially preferred compounds of the general formula (I) are those
in which
R¹ represents a group of the formula

—OCH₃, —OC₂H₅, —OC₃H₇, —OCH(CH₃)₂, —OC₄H₉,

—OC(CH₃)₃, —O—CH₂—CH=CH₂, —O—CH₂—C₆H₅,

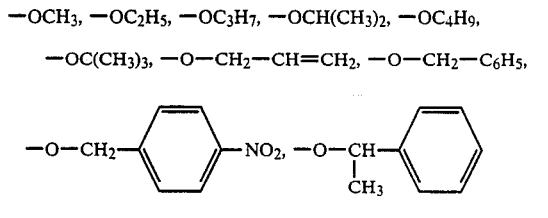

(R form, S form or RS mixture)

—NH₂, —NHCH₃, —N(CH₃)₂, —NHC₂H₅, —N(C₂H₅)₂,

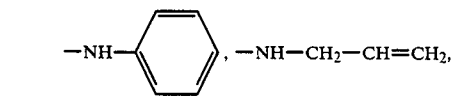

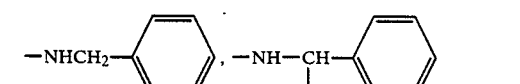

(R form, S form or RS mixture),

-continued
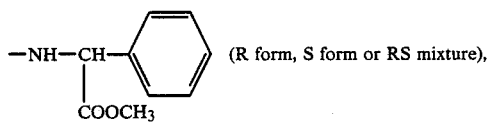 (R form, S form or RS mixture),
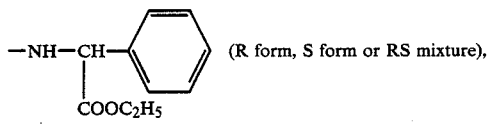 (R form, S form or RS mixture),
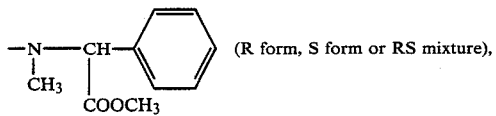 (R form, S form or RS mixture),
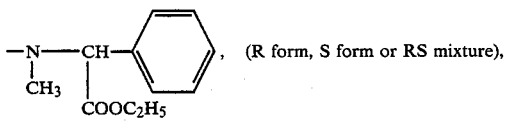 (R form, S form or RS mixture),
—NH—CO—NH$_2$, —NH—CO—NHCH$_3$,
—NH—CO—N(CH$_3$)$_2$, 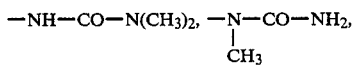
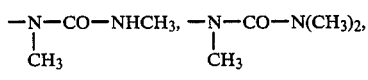
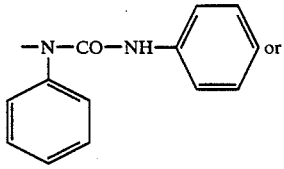 or
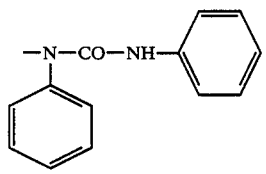,
the AR$^2$ group represents a radical of the formula
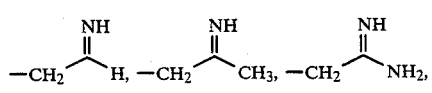
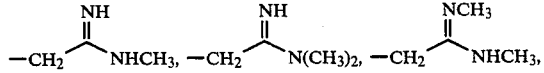
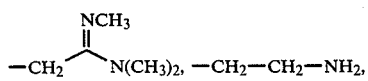
—CH$_2$—CH$_2$—NHCH$_3$, —CH$_2$—CH$_2$—N(CH$_3$)$_2$,
—CH$_2$—CH$_2$—NHCOCH$_3$, 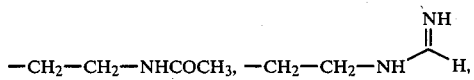
-continued
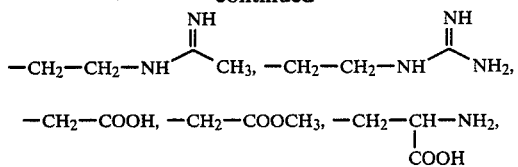
—CH$_2$—COOH, —CH$_2$—COOCH$_3$, 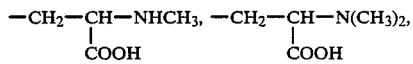
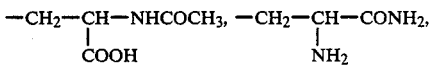
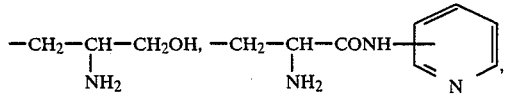
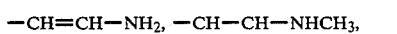
—CH=CH—NH$_2$, —CH=CH—NHCH$_3$,
—CH=CH—N(CH$_3$)$_2$, —CH=CH—NHCOCH$_3$,
—CH=CH—CH$_2$—NH$_2$, 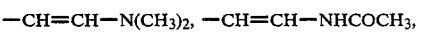
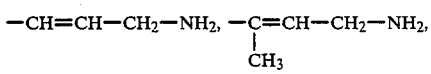
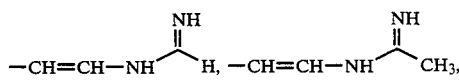
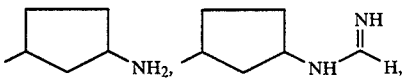
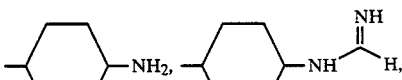
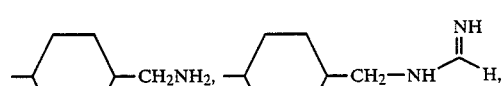
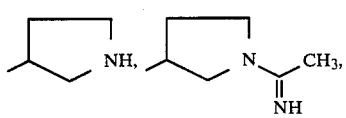
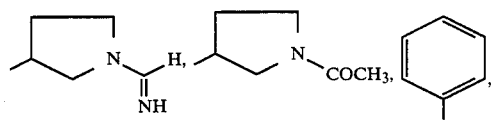
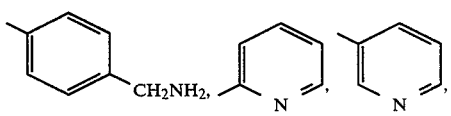
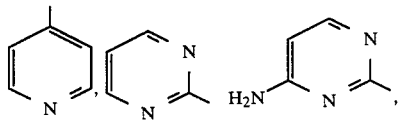

-continued
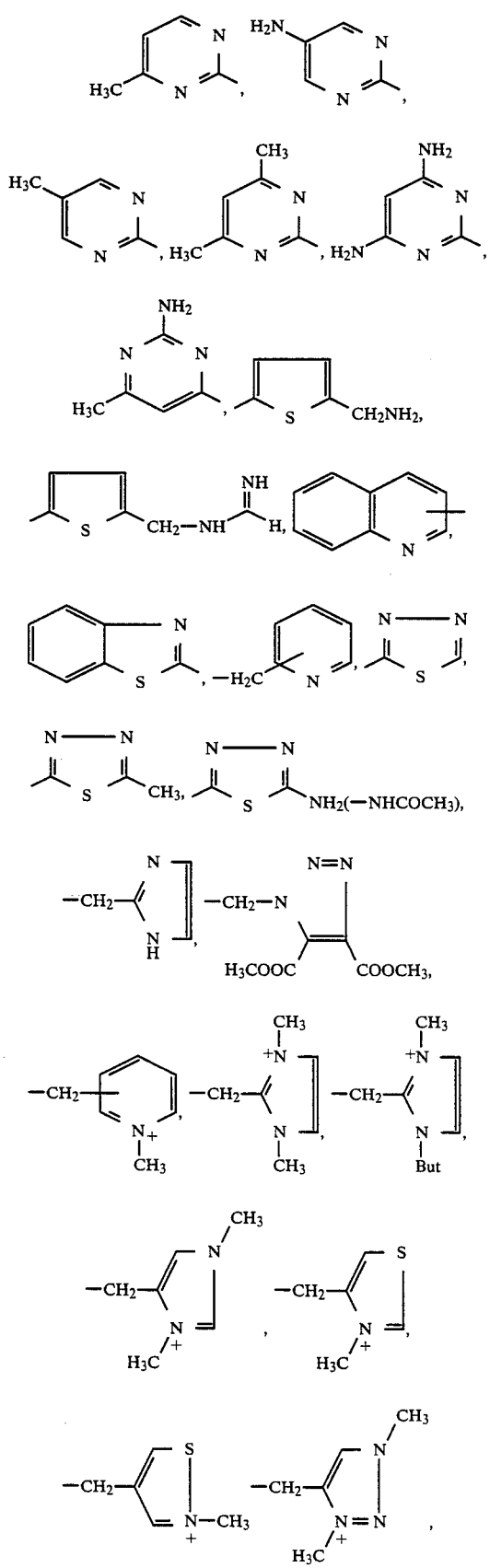
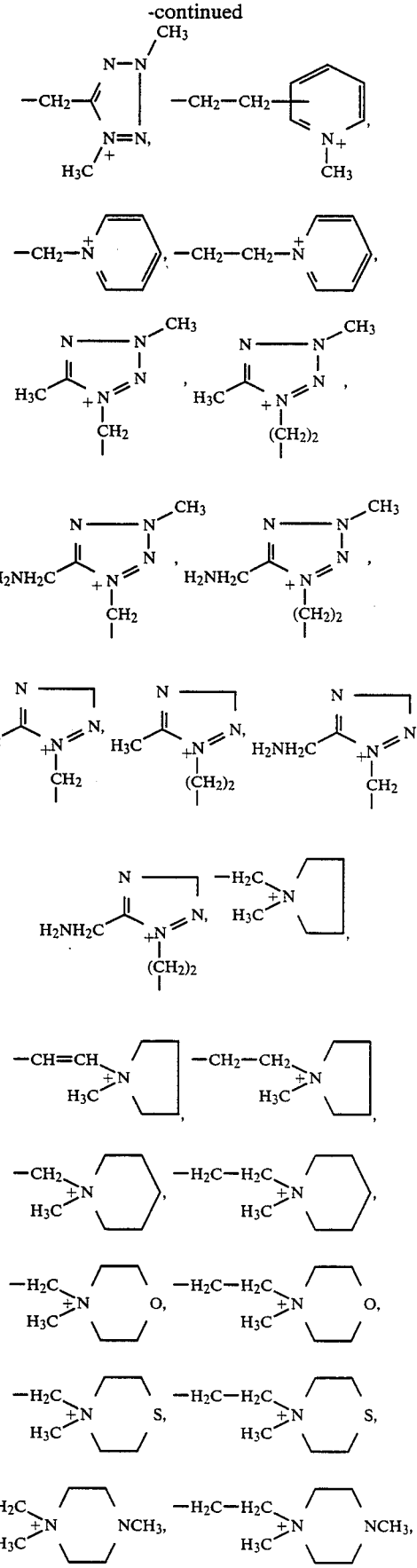

-continued

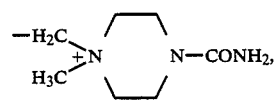

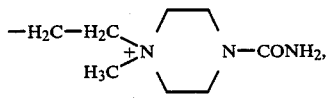

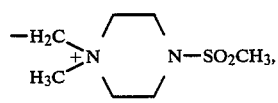

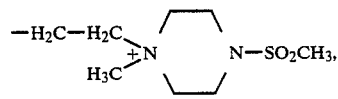

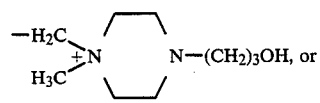

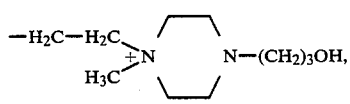

and
R³ represents a carboxyl group COOR²⁰, in which
  R²⁰ denotes hydrogen, allyl, 4-nitrobenzyl or 4-methoxybenzyl, or
  represents COO³¹ if the AR² group represents a positively charged radical,
and the salts thereof.

Besides the products listed in the examples, the following compounds of the general formula (I), and the salts thereof, are especially preferred:

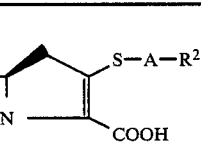

| R¹ | ASR² |
|---|---|
| CH₃O | 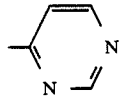 |
| CH₃O | 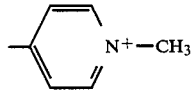 |
| CH₃O | 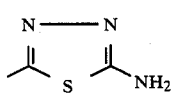 |
| CH₃O |  |

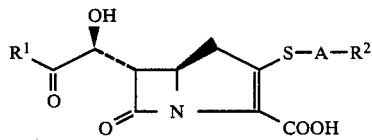

| R¹ | ASR² |
|---|---|
| CH₃O | 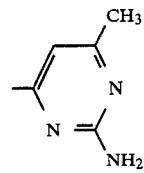 |
| CH₃O | 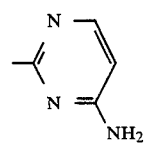 |
| CH₃O | 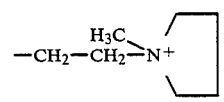 |
| CH₃O | 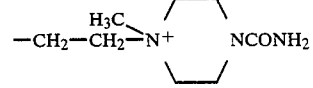 |
| CH₃O | 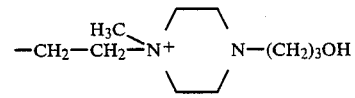 |
| CH₃O | 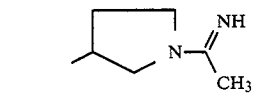 |
| CH₃O | 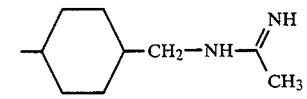 |
| CH₃O | 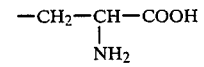 |
| CH₃O | 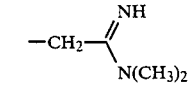 |
| CH₃O | 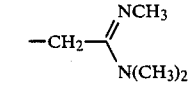 |
| CH₃O | —CH₂—CH₂—NH₂ |
| CH₃O | —CH₂—CH₂—NHCOCH₃ |
| CH₃O | 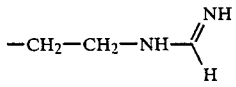 |

| R¹ | ASR² | R¹ | ASR² |
|---|---|---|---|
| CH₃O | −CH₂−CH₂−N⁺(pyridinium) | OH | (4,6-dimethylpyrimidin-2-yl)guanidine substituent with =CH− linker and −NH₂ |
| CH₃O | −CH₂−C(=N⁺(CH₃))−N(CH₃) imidazolinium | OH | 4-aminopyrimidin-2-yl (2-methyl, 4-amino) |
| CH₃O | −CH₂−(1-methylpyridinium-4-yl) | OH | −CH₂−CH₂−N⁺(CH₃)(pyrrolidinium) |
| CH₃O | −CH₂−C(=N−N⁺(CH₃))−N=N−CH₃ (tetrazinium) | OH | −CH₂−CH₂−N⁺(CH₃)(piperazinyl)−NCONH₂ |
| CH₃O | −CH₂−(1H-imidazol-2-yl) | OH | −CH₂−CH₂−N⁺(CH₃)(piperazinyl)−N−(CH₂)₃OH |
| CH₃O | −CH₂−CH₂−N⁺(CH₃)(thiomorpholinium) | OH | 3-methylpyrrolidin-1-yl with C(=NH)CH₃ |
| CH₃O | 5-methylthiophen-2-yl−CH₂−NH−C(=NH)H | OH | 4-methylcyclohexyl−CH₂−NH−C(=NH)CH₃ |
| CH₃O | −CH₂−C(=N−N⁺(CH₃))−S (thiadiazolinium, N-methyl) | OH | −CH₂−CH(NH₂)−COOH |
| OH | 4-methylpyrimidin-2-yl | OH | −CH₂−C(=NH)−N(CH₃)₂ |
| OH | −CH₂−(1-methylpyridinium-4-yl) | OH | −CH₂−C(=NCH₃)−N(CH₃)₂ |
| OH | 1,2,4-triazol-3-yl-S−C(CH₃)=... −S−C(NH₂) | OH | −CH₂−CH₂−NH₂ |
|  |  | OH | −CH₂−CH₂−NHCOCH₃ |
|  |  | OH | −CH₂−CH₂−NH−C(=NH)H |

| 25 | | 26 | |
|---|---|---|---|
| -continued | | -continued | |
| 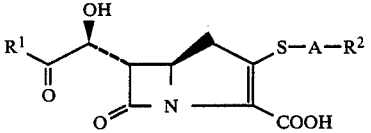 | | 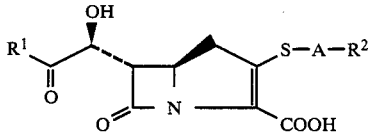 | |
| R¹ | ASR² | R¹ | ASR² |
| OH | 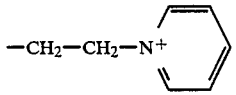 | OC₂H₅ | 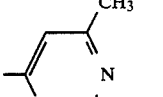 |
| OH | 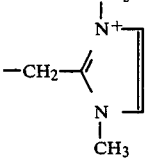 | OC₂H₅ | 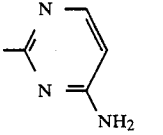 |
| OH | 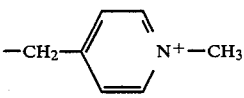 | OC₂H₅ | 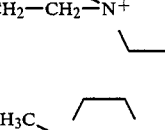 |
| OH | 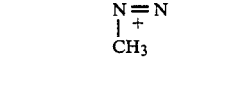 | OC₂H₅ | 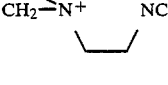 |
| OH | 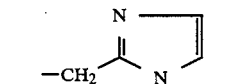 | OC₂H₅ | 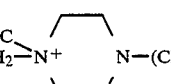 |
| OH | 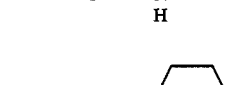 | OC₂H₅ | 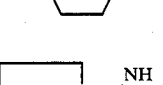 |
| OH | 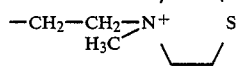 | OC₂H₅ | 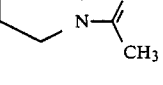 |
| OH | 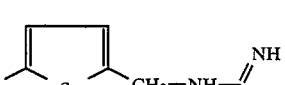 | OC₂H₅ | 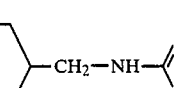 |
| OC₂H₅ | 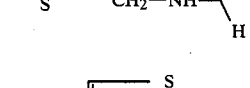 | OC₂H₅ | 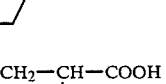 |
| OC₂H₅ | 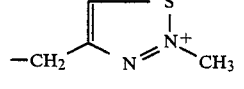 | OC₂H₅ | 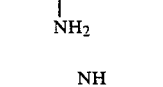 |
| | | OC₂H₅ | —CH₂—CH₂—NH₂ |
| | | OC₂H₅ | —CH₂—CH₂—NHCOCH₃ |
| OC₂H₅ | 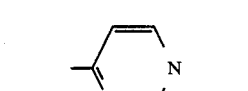 | OC₂H₅ | 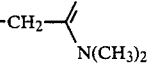 |

4,863,916
| 27 -continued | | 28 -continued | |
|---|---|---|---|
| 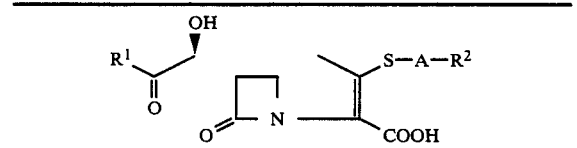 | | 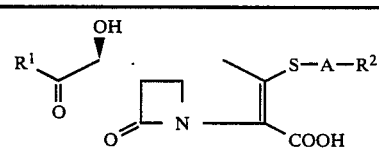 | |
| R¹ | ASR² | R¹ | ASR² |
| OC₂H₅ | 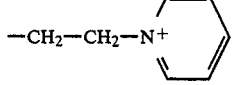 | OCH₂—CH=CH₂ |  |
| OC₂H₅ | 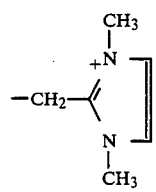 | OCH₂—CH=CH₂ | 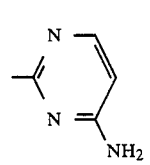 |
| OC₂H₅ | 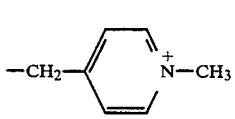 | OCH₂—CH=CH₂ | 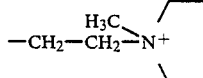 |
| OC₂H₅ | 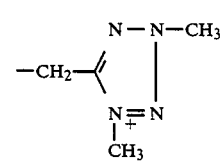 | OCH₂—CH=CH₂ | 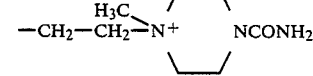 |
| OC₂H₅ | 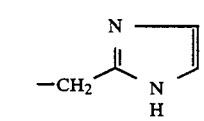 | OCH₂—CH=CH₂ | 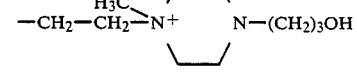 |
| OC₂H₅ | 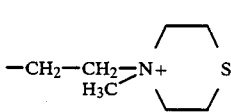 | OCH₂—CH=CH₂ | 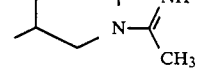 |
| OC₂H₅ | 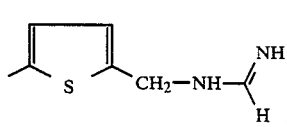 | OCH₂—CH=CH₂ | 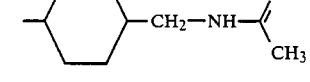 |
| OC₂H₅ | 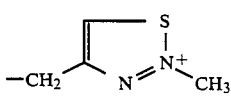 | OCH₂—CH=CH₂ | 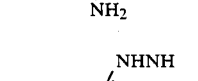 |
| OCH₂—CH=CH₂ | 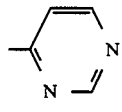 | OCH₂—CH=CH₂ | 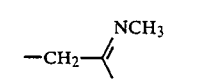 |
| OCH₂—CH=CH₂ | 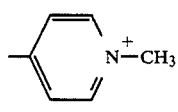 | OCH₂—CH=CH₂<br>OCH₂—CH=CH₂ | —CH₂—CH₂—NH₂<br>—CH₂—CH₂—NHCOCH₃ |
| OCH₂—CH=CH₂ | 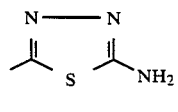 | OCH₂—CH=CH₂ | 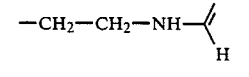 |

-continued
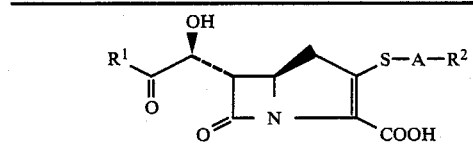
| R¹ | ASR² |
|---|---|
| OCH₂—CH=CH₂ | 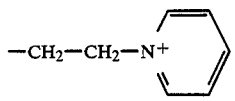 |
| OCH₂—CH=CH₂ | 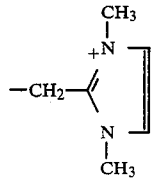 |
| OCH₂—CH=CH₂ | 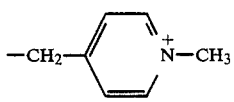 |
| OCH₂—CH=CH₂ | 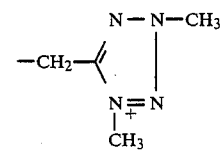 |
| OCH₂—CH=CH₂ | 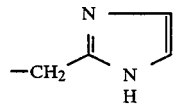 |
| OCH₂—CH=CH₂ | 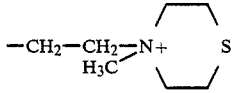 |
| OCH₂—CH=CH₂ | 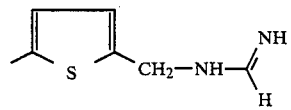 |
| OCH₂—CH=CH₂ | 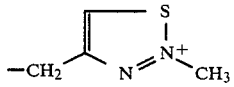 |
| NH₂ | 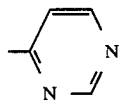 |
| NH₂ | 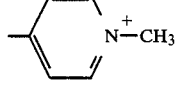 |
| NH₂ | 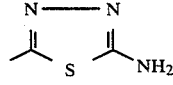 |
-continued
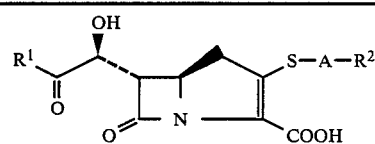
| R¹ | ASR² |
|---|---|
| NH₂ | 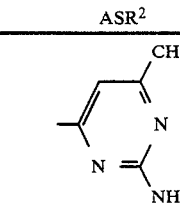 |
| NH₂ | 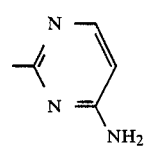 |
| NH₂ | 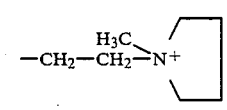 |
| NH₂ | 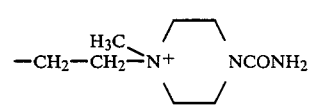 |
| NH₂ | 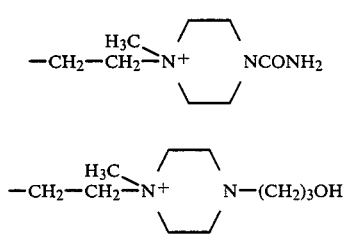 |
| NH₂ | 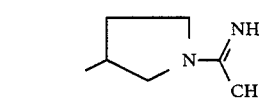 |
| NH₂ | 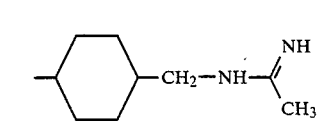 |
| NH₂ | 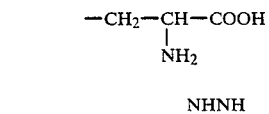 |
| NH₂ | 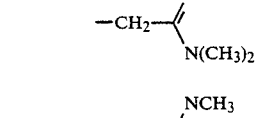 |
| NH₂ | —CH₂—CH₂—NH₂ |
| NH₂ | —CH₂—CH₂—NHCOCH₃ |
| NH₂ | 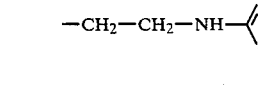 |

4,863,916
| 31 | 32 |
|---|---|

-continued

| R¹ | ASR² | R¹ | ASR² |
|---|---|---|---|
| NH₂ | 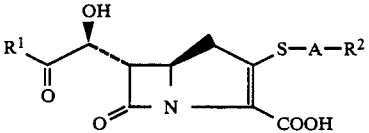 —CH₂—CH₂—N⁺(pyridinium) | N(CH₃)₂ | 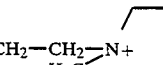 |
| NH₂ | 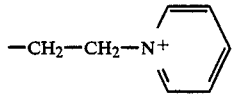 —CH₂—C(=N⁺(CH₃))—N(CH₃) (imidazolinium) | N(CH₃)₂ | 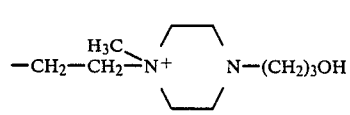 |
| NH₂ | 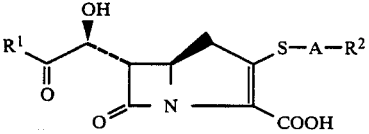 —CH₂—(4-pyridinium-N-CH₃) | N(CH₃)₂ | 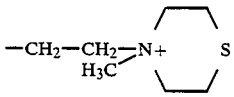 —CH₂—CH₂—N⁺(CH₃)(pyrrolidine) |
| NH₂ | 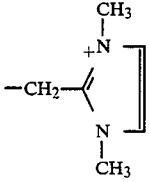 —CH₂—C(=N-N(CH₃))—N⁺=N-CH₃ | N(CH₃)₂ | 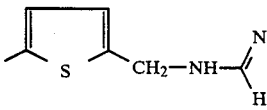 —CH₂—CH₂—N⁺(CH₃)(piperazine-NCONH₂) |
| NH₂ | 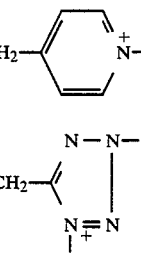 —CH₂—(2-imidazolyl) | N(CH₃)₂ | 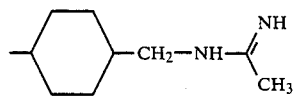 —CH₂—CH₂—N⁺(CH₃)(piperazine-N-(CH₂)₃OH) |
| NH₂ | 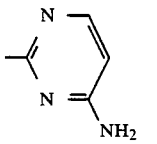 —CH₂—CH₂—N⁺(CH₃)(thiomorpholine) | N(CH₃)₂ | 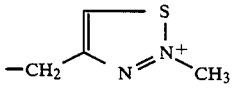 (methylpyrrolidine-CH₂ group with amidine) |
| NH₂ | 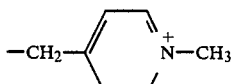 (methylthiophene-CH₂-NH-C(=NH)H) | N(CH₃)₂ | 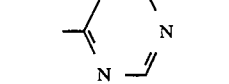 (methylcyclohexyl-CH₂-NH-C(=NH)CH₃) |
| NH₂ | 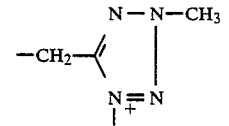 —CH₂—(thiadiazolium-N-CH₃) | N(CH₃)₂ | —CH₂—CH(NH₂)—COOH |
| N(CH₃)₂ | 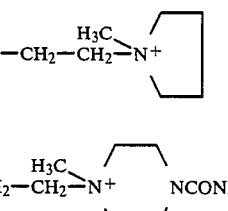 (methylpyrimidine) | N(CH₃)₂ | 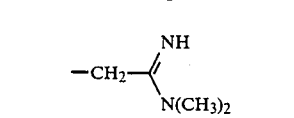 —CH₂—C(=NH)—N(CH₃)₂ |
| N(CH₃)₂ | 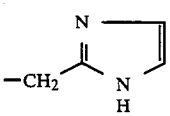 —CH₂—(4-pyridinium-N-CH₃) | N(CH₃)₂ | 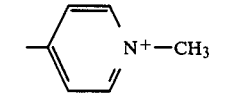 —CH₂—C(=NCH₃)—N(CH₃)₂ |
| N(CH₃)₂ | 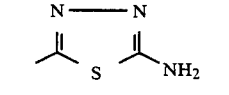 =C(CH₃)₂ linked via S to C(NH₂)=N—N | N(CH₃)₂ | —CH₂—CH₂—NH₂ |
|  |  | N(CH₃)₂ | —CH₂—CH₂—NHCOCH₃ |
|  |  | N(CH₃)₂ | 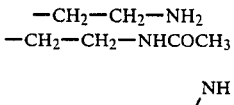 —CH₂—CH₂—NH—C(=NH)H |

4,863,916

-continued

| R¹ | ASR² |
|---|---|
| N(CH₃)₂ | —CH₂—CH₂—N⁺(pyridinium) |
| N(CH₃)₂ | —CH₂—(imidazolium with N-CH₃, N⁺-CH₃) |
| N(CH₃)₂ | —CH₂—(4-pyridyl)-N⁺—CH₃ |
| N(CH₃)₂ | —CH₂—C(=N—N(CH₃))—N⁺=N—CH₃ |
| N(CH₃)₂ | —CH₂—(2-imidazolyl, NH) |
| N(CH₃)₂ | —CH₂—CH₂—N⁺(CH₃)(thiomorpholinyl) |
| N(CH₃)₂ | —(5-methyl-2-thienyl)—CH₂—NH—CH=NH |
| N(CH₃)₂ | —CH₂—C(=N—N⁺(CH₃))—S (thiadiazolium) |
| NH—CH(CH₃)—C₆H₅ | —(pyrimidin-4-yl) |
| NH—CH(CH₃)—C₆H₅ | —(1-methyl-4-pyridinium) |
| NH—CH(CH₃)—C₆H₅ | —C(CH₃)(=N—N=)—S—C(NH₂)= |

-continued

| R¹ | ASR² |
|---|---|
| NH—CH(CH₃)—C₆H₅ | —C(CH₃)=C(CH₃)—N=C(NH₂)—N (guanidinopyrimidine) |
| NH—CH(CH₃)—C₆H₅ | —(2-methyl-4-aminopyrimidinyl) |
| NH—CH(CH₃)—C₆H₅ | —CH₂—CH₂—N⁺(CH₃)(pyrrolidinyl) |
| NH—CH(CH₃)—C₆H₅ | —CH₂—CH₂—N⁺(CH₃)(piperazinyl)—NCONH₂ |
| NH—CH(CH₃)—C₆H₅ | —CH₂—CH₂—N⁺(CH₃)(piperazinyl)—N—(CH₂)₃OH |
| NH—CH(CH₃)—C₆H₅ | —(4-methylcyclohexyl)—CH₂—N=C(CH₃)(NH) via pyrrolidine |
| NH—CH(CH₃)—C₆H₅ | —(cyclohexyl)—CH₂—NH—C(CH₃)=NH |
| NH—CH(CH₃)—C₆H₅ | —CH₂—CH(NH₂)—COOH |
| NH—CH(CH₃)—C₆H₅ | —CH₂—C(=NH)—N(CH₃)₂ |
| NH—CH(CH₃)—C₆H₅ | —CH₂—C(=NCH₃)—N(CH₃)₂ |
| NH—CH(CH₃)—C₆H₅ | —CH₂—CH₂—NH₂ |

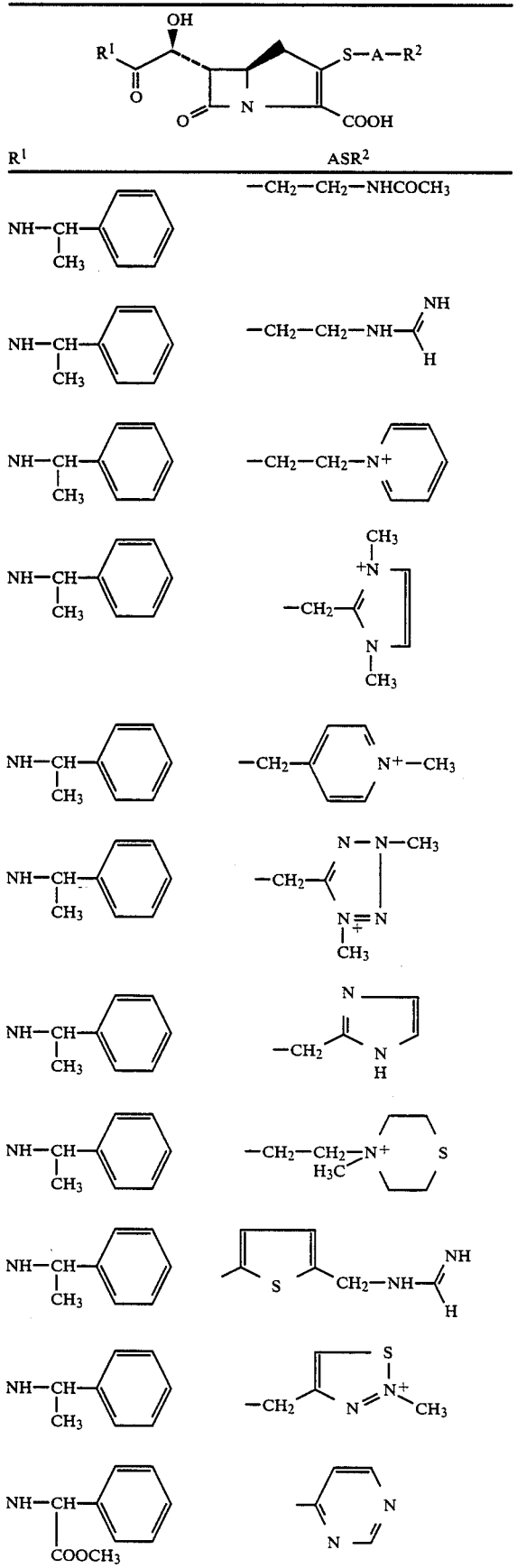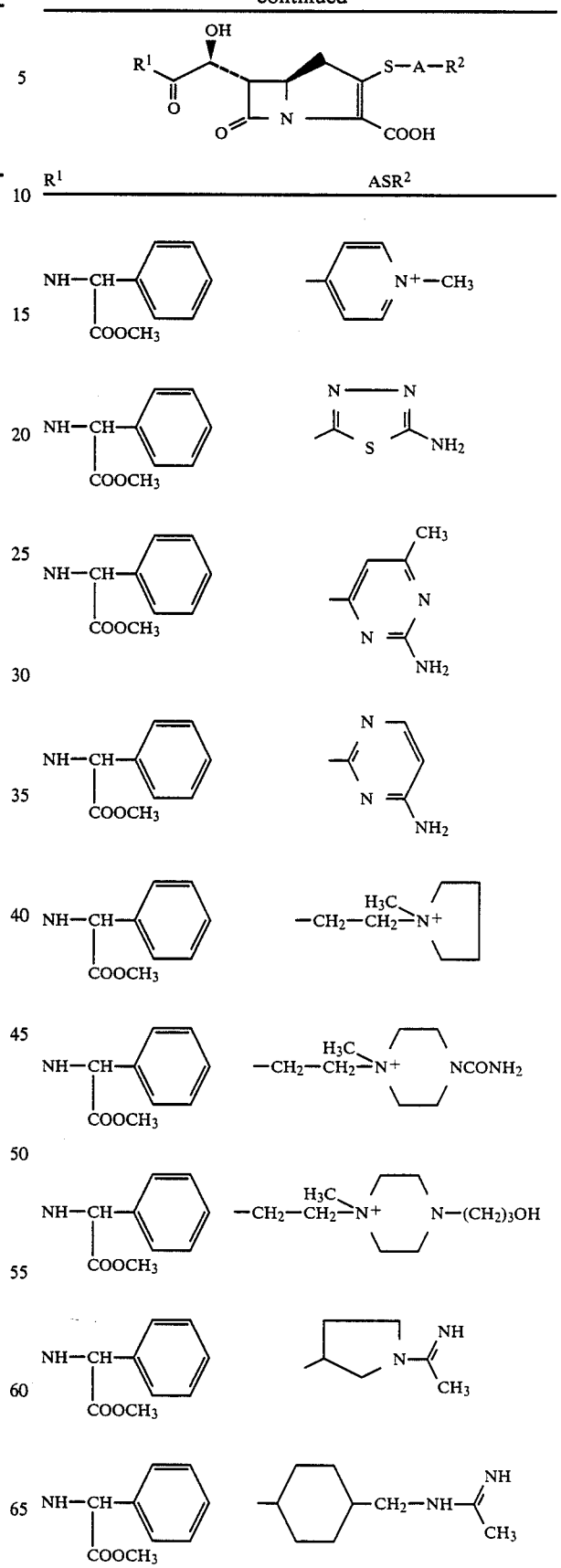

-continued

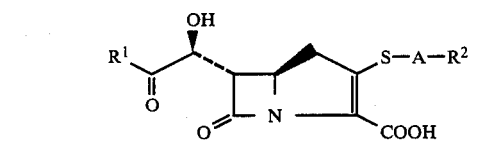

| $R^1$ | $ASR^2$ |
|---|---|
| 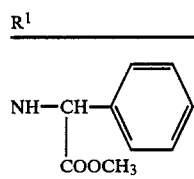 | 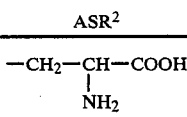 |
| 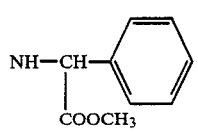 | 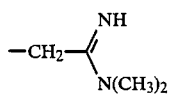 |
| 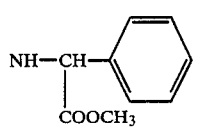 | 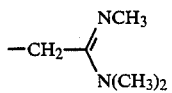 |
| 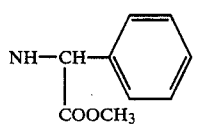 | —CH$_2$—CH$_2$—NH$_2$ |
| 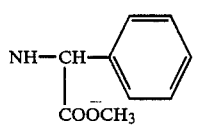 | —CH$_2$—CH$_2$—NHCOCH$_3$ |
| 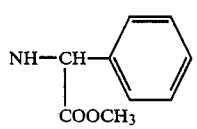 | 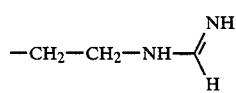 |
| 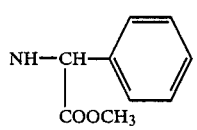 | 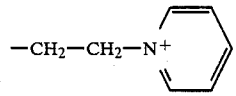 |
| 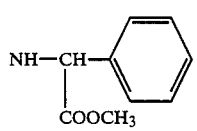 | 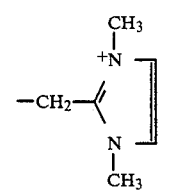 |
| 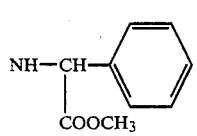 | 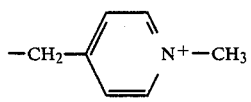 |

-continued

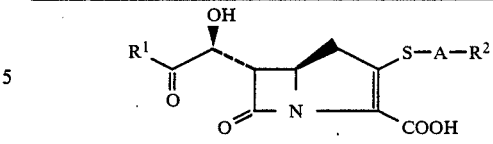

| $R^1$ | $ASR^2$ |
|---|---|
| 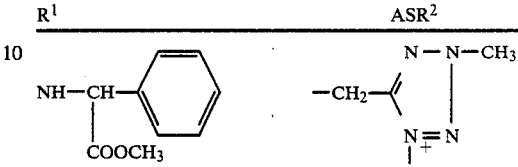 |  |
| 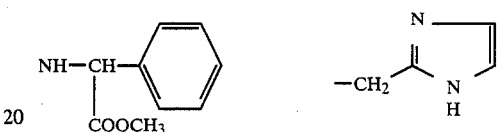 |  |
| 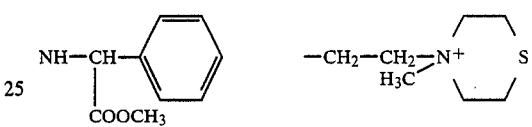 |  |
| 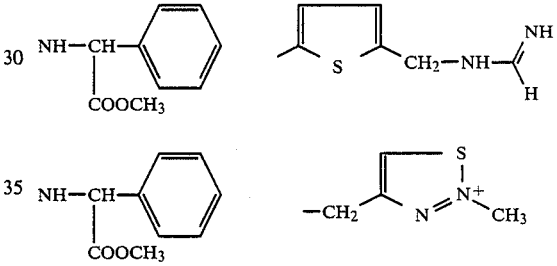 |  |

The compounds, according to the invention, of the general formula (I) may exist as free acids, as esters, as internal salts or as non-toxic, physiologically acceptable salts, either with an external counteranion (when $R^2$ represents a positively charged radical), or with a countercation (when $R^3$ represents $COO^{31}$). As countercations, alkali metal or alkaline earth metal cations, such as, for example, sodium, potassium, magnesium or calcium ions, or aluminum or ammonium ions, and also non-toxic substituted ammonium ions from amines such as di- and tri-lower alkylamines, procaine, dibenzylamine, N,N'-dibenzylethylenediamine, N-benzyl-β-phenyl-ethylamine, N-methylmorpholine, N-ethylmorpholine, 1-ephenamine, dihydroabiethylamine, N,N'-bis-dihydroabiethylethylenediamine, N-lower alkylpiperidines and other amines which can be used for formation of salts of β-lactam compounds may preferably be mentioned.

Suitable counteranions are, in particular, chloride, bromide, iodide, hydroxide, bicarbonate, carbonate, bisulphate, sulphate, or anions of customary organic acids such as, for example, acetate, maleate, fumarate, benzoate, lactate, or sulphonates.

The compounds according to the invention have several asymmetric carbon atoms and can thus exist in several stereochemical forms. The invention covers the mixtures of isomers and the individual stereoisomers. Preferred compounds of the formula (I) are those having the 5R, 6S, 8S configuration:

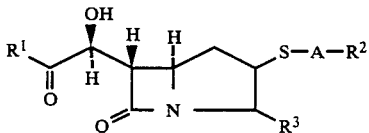

When the side chains, particularly $R^1$, contain further centers of asymmetry, this leads to diastereomeric products, which are likewise covered by the ivnention. The stereochemically homogenous products may be prepared either from the mixtures by conventional separation methods (for example crystallization or chromatography), or by stereo-specific synthesis starting from optically pure material.

The compounds, according to the invention, of the general formula (I), and the salts thereof, are obtained by reacting keto-esters of the general formula (II)

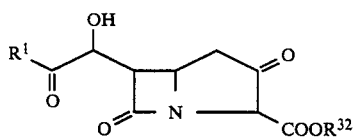

in which
$R^1$ has the abovementioned meaning and
$R^{32}$ has the meaning of $R^{20}$, but may not represent hydrogen, and where the $COOR^{32}$ group may not represent a carboxylate anion, and
thiols of the general formula (III)

 (III)

in which A and $R^2$ have the meaning specified, in inert solvents, if appropriate in the presence of bases with an auxiliary substance, protecting groups are cleaved off, if appropriate, and the desired salts are prepared, if desired, or the salts are converted into the free compounds.

If (2R, 5R, 6S)-3,7-dioxo-6-[(1S)-1-hydroxy-1-methoxycarbonyl]methyl-2-p-nitrobenzyloxycarbonyl-1-azabicyclo[3.2.0]heptane and 4-mercaptopyridine are used as starting materials, then the process may be illustrated by the following equation:

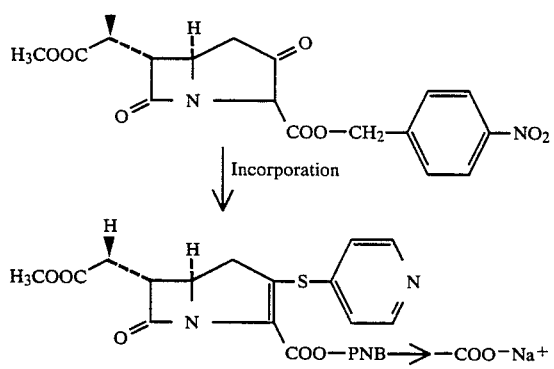

Suitable solvents are all inert organic solvents which do not change under the reaction conditions. These preferably include ethers, such as, for example, diethyl ether, dioxane, tetrahydrofuran, glycol dimethyl ether, or butyl methyl ether, or hydrocarbons, such as benzene, toluene or xylene, or halogenated hydrocarbons, such as, for example, dichloromethane, trichloroethane, tetrachloromethane, 1,1,2-trichloromethane, dichloroethylene or trichloroethylene, chlorobenzene or dichlorobenzene, or acetone, ethyl acetate, acetonitrile, dimethylformamide, hexamethylphosphoric triamide, N,N'-dimethyl-propylene-urea, acetonitrile, or mixtures of the solvents mentioned.

Suitable bases are the conventional organic bases. These preferably include tertiary amines, such as, for example, trimethylamine, triethylamine, tripropylamine, tributylamine, ethyldiisopropylamine, pyridine, dimethylaminopyridine, picoline, lutidine, N-methylmorpholine, N-methylpiperidine, 1,5-diazabicyclo[5.4.0]undec-5-ene (DBU) or 1,5-diazabicyclo[4.3.0]non-3-ene (DBN).

In general, substances which convert the ketoesters of the general formula (II) into compounds of the general formula (IV)

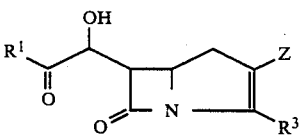

in which Z represents a leaving group from the series comprising

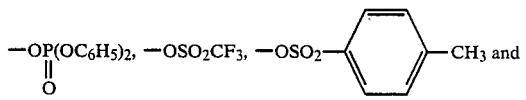

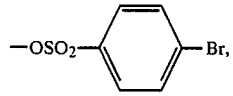

preferably

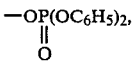

are employed as auxiliary substances.

These preferably include acyl halides or acid anhydrides of 4-toluenesulphonic acid, 4-bromo-phenylsulphonic acid, trifluoromethanesulphonic acid, or diphenyl chlorophosphate. Diphenyl chlorophosphate is particularly preferably used.

The intermediates of the general formula (IV) can be isolated. However, it has proven favorable to carry out the reaction in one stage without isolation of the intermediates.

The process is preferably carried out by reacting the keto-ester, in a suitable solvent, with the base, diphenyl chlorophosphate, and then with the appropriate thiol, if appropriate in the presence of further bases.

It is likewise possible to employ the thiol (III) in the form of its salts, or to prepare the corresponding thiolate by addition of base to the reaction mixture.

The base is generally employed in an amount from 1 to 3 moles, preferably from 1 to 1.5 moles, relative to 1 mole of the keto-ester. The thiol is generally employed in an amount from 1 to 4 moles, preferably from 1 to 2 moles, relative to 1 mole of the keto-ester. If the thiolate is generated in the reaction solution from the thiol, further base is employed in amounts from 1 to 5 moles, preferably from 1 to 2 moles, relative to 1 mole of thiol.

The reaction is generally carried out in a temperature range from −80° C. to +60° C., preferably from −50° C. to +40° C.

In general, the reaction is carried out at atmospheric pressure. However, it is likewise possible to work at reduced pressure or increased pressure.

The thiols of the general formula (III) employed as starting materials are known or can be prepared by known methods [Patent Applications: European Patents 36,650 and 48,168; German Patent 2,738,711; and U.S. Pat. No. 3,798,229].

The compounds of the general formula (II) employed as starting materials are new. They can be prepared by known process steps according to the following equation:

$R^{33}$ represents an amino-protectng group, preferably 4-methoxyphenyl, and $R^{34}$ represents a hydroxyl-protecting group.

The epoxide (V), in which $R^1$ has the abovementioned meaning and $R^{33}$ represents an amino-protecting group, as already defined above, particularly preferably 4-methoxyphenyl, is then reacted, in step [A], with tetrabutylammonium fluoride in inert organic solvents, such as ethers, hydrocarbons or halogenated hydrocarbons, preferably in ethers, such as diethyl ether, dioxane or, particularly preferably, tetrahydrofuran, at temperatures from −80° C. to +40° C., preferably from −30° C. to +10° C., to form the azetidine diones (VI), as described by Ernest et al. in European Patent 126,709.

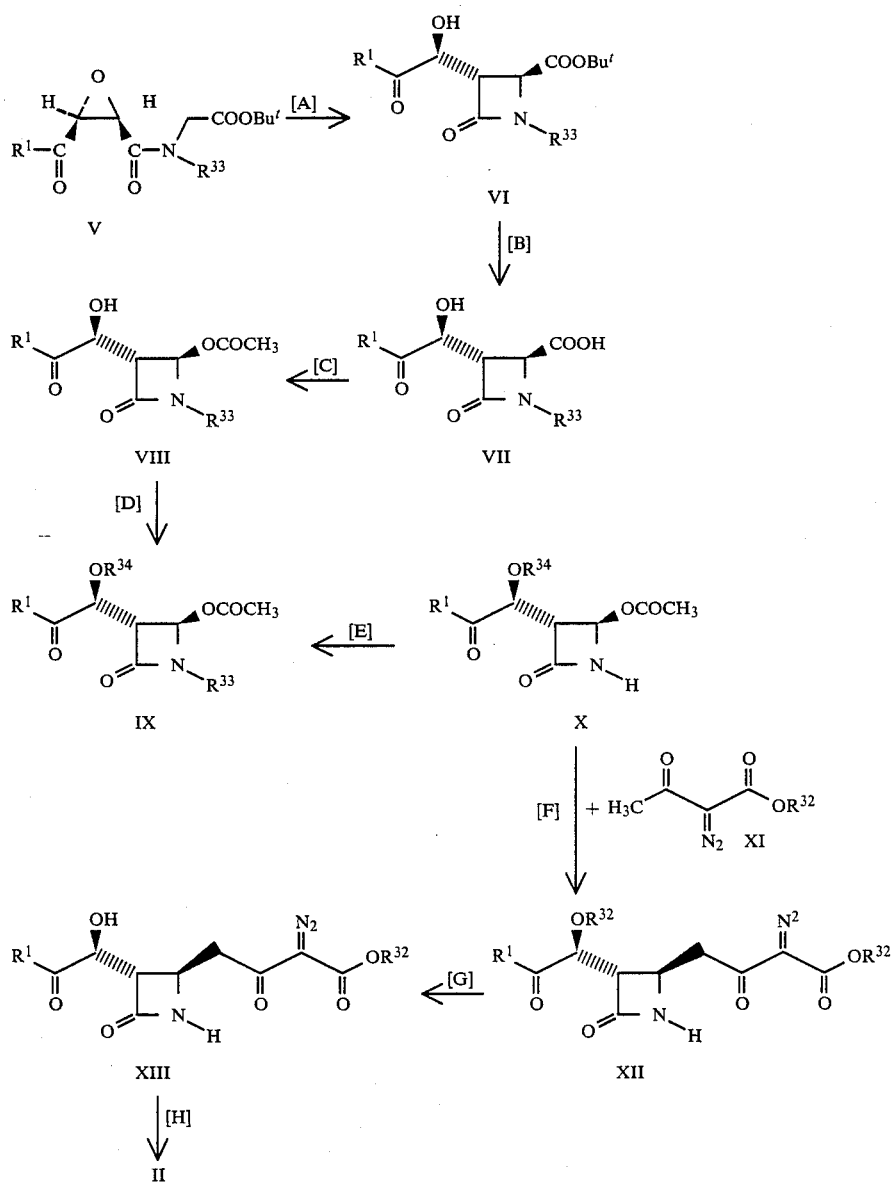

in which $R^1$ and $R^{32}$ have the abovementioned meaning,

In step [B], the acid (VII) is prepared from (VI), as described by M. Shiozaki et al. in Tetrahedron 40, 1795 (1984), with the aid of acids, preferably strong carboxylic acids or sulphonic acids, or particularly preferably trifluoroacetic acid in inert organic solvents, such as ethers, hydrocarbons, or, preferably, halogenated hydrocarbons, such as tetrachloromethane, trichloromethane, or particularly preferably, dichloromethane, at temperatures from $-30°$ C. to $+60°$ C., preferably from $0°$ C. to $+30°$ C.

In step [C], the acetylazetidinone (VIII) is prepared in one step, as described by P. J. Reider et al. in Tetrahedron Lett. 1982, 2293, by oxidative decarboxylation of (VII) with the aid of acids, preferably carboxylic acids, such as acetic acid, propionic acid, chloroacetic acid or trifluoroacetic acid, particularly preferably acetic acid, and using an oxidant, preferably lead tetraacetate, and simultaneous acetylation.

In step [D], the compound (VIII), having a free hyroxyl group, is converted into compounds (IX) with a protected hydroxyl group. $R^{34}$ here represents a conventional hydroxyl-protecting group. These preferably include silyl groups, such as, for example, trimethylsilyl or tert-butyl-dimethylsilyl, or oxycarbonyl groups, such as, for example, benzyloxycarbonyl, 4-nitrobenzyloxycarbonyl, tert-butoxycarbonyl, trichloroethoxycarbonyl or allyloxycarbonyl, or other customary protecting groups, such as formyl or acetyl. Silyl protecting groups are particularly preferred. The tert-butyldimethylsilyl protecting group is very particularly preferably employed. Tert-butyl-dimethylsilyl chloride and dimethylaminopyridine in dimethylformamide are particularly preferably used, as described by M. Shiozaki et al. in Tetrahedron 40, 1795 (1984).

In step [E], the amino-protecting group ($R^{33}$) in (IX) is cleaved off by methods which are conventional in β-lactam chemistry, as described, for example, by D. R. Kronenthal et al. in J. Org. Chem. 47, 2765 (1982). The 4-methoxyphenyl and 2,4-dimethoxybenzyl group are used as preferred amino-protecting groups. The 4-methoxyphenyl group is very particularly preferred. The cleaving-off is preferably carried out with the aid of cerium(IV) nitrate in an acetonitrile/water mixture, as described, for example, by D. R. Kronenthal, C. Y. Han and M. K. Taylor in J. Org. Chem. 47, 2765 (1982).

In step [F], the azetidinone (X) is reacted in several steps with the diazoketo-ester (XI) in the presence of silylating agents with the aid of bases in inert organic solvents, such as ethers, for example diethyl ether, dioxane or tetrahydrofuran, or hydrocarbons, for example benzene, toluene, xylene or petroleum fractions, or halogenated hydrocarbons, for example dichloromethane, trichloromethane or tetrachloromethane, to form the compounds of the formula (XII), as described, for example, by J. B. Buynak et al. in J. Chem. Soc. Chem. Commun. 1984, 948 or by P. J. Reider et al., in Tetrahydron Letters 1982, 379, or by M. Shiozaki et al., in J. Org. Chem. 39, 2399 (1983) or Tetrahedron 40, 1795 (1984), or by A. G. M. Barret in J. Org. Chem. 49, 1679 (1984), or by T. Kametani et al. in Heterocycles 14, 1967 (1980) or in J. Chem. Soc. Perkin I 1981, 228.

However, the compounds (XII) are preferably prepared in process step [F] by a process in which the azetidinones (X) are reacted in a one-pot process with diazoketo-esters (XI) in an inert diluent, in the presence of a base and a silylating agent. The silylating agent here acts simultaneously as catalyst.

Suitable diluents are all inert solvents which do not alter under the reaction conditions. These preferably include ethers, such as dimethoxyethane, diglyme, triglyme, tetrahydrofuran, dioxide, diethyl ether or tert-butyl methyl ether, or halogenated hydrocarbons, such as dichloromethane, trichloromethane, tetrachloromethane, 1,1,2-trichloroethane, dichloroethylene or trichloroethylene, chlorobenzene or dichlorobenzene, or ethyl acetate, toluene or cyclohexane.

The reaction is generally carried out at temperatures from $-30°$ C. to $+50°$ C., preferably at room temperature. Suitable bases are all tertiary amines. Triethylamine, tripropylamine, tributylamine, ethyldiisopropylamine, dimethylaminopyridine, pyridine, picoline, lutidine, N-methylmorpholine, N-methylpiperidine, 1,5-diazabicyclo[5.4.0]undec-5-ene (DBU) or 1,5-diazabicyclo[4.3.0]non-3-ene (DBN) should preferably be mentioned.

Suitable silylating agents or catalysts are all silylating agents which can act simultaneously as Lewis acids. These preferably include trialkylsilyl perfluoroalkanesulphonates, trialkylsilyl alkanesulphonates, trialkylsilyl arylsulphonates, trialkylsilyl perfluoroalkanoates, trialkylsilyl alkanoates, trialkylsilyl halides, trialkylsilyl perchlorates, trialkylsilyldifluorophosphates, trialkylsilyldichlorophosphates, trialkylsilyl fluorosulphonates, N,O-bis(trialkylsilyl)acetamides and trialkylsilyl cyanides, Trimethylsilyl trifluoromethanesulphonate, trimethylsilyl nonafluorobutanesulphonate, trimethylsilyl trifluoroacetate, trimethylsilyl perchlorate, trimethylsilyl fluorosulphonate and N,O-bis(trimethylsilyl)trifluoroacetamide are particularly suitable.

To carry out the process, it is necessary to employ initially (a) 0.1–1.5, preferably 0.5–1 equivalent of the compound X per equivalent of the compound XI, (b) 1–2, preferably 1–1.5 equivalents of silylating agent per equivalent of the compound XI, and (c) 1.01–3, preferably 1.05–2 equivalents of a base (amine) per equivalent of silylating agent, and, after 0.1–24 hours, preferably 0.1–12 hours, to add sufficient further silylating agent so that the silylating agent is present in a slight excess, preferably in a catalytic excess, over the base (amine).

When carrying out the process, one additional equivalent of both silylating agent and base (amine) should be employed in addition to the ratios of silylating agent and base (amine) stated above for each free, i.e. to be protected, hydroxyl, mercapto or amino group in the compounds X and XI (for example when $R^{33}=H$).

The reaction rate is substantially dependent on the amount of catalyst used, i.e. on the silylating agent excess. The reaction occurs within 0.1 to 48 hours, preferably from 0.1 to 24 hours.

This new one-part process may be illustrated by the following reaction equation:

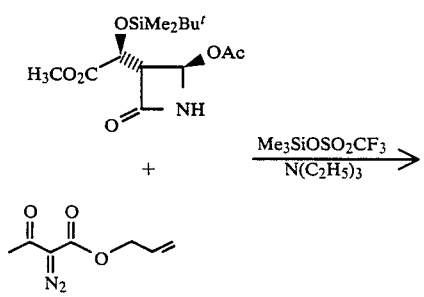

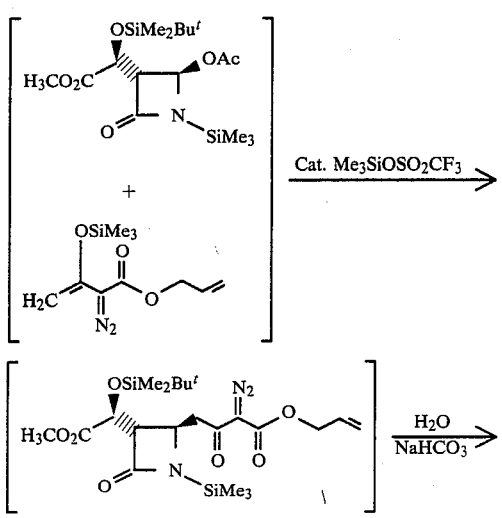

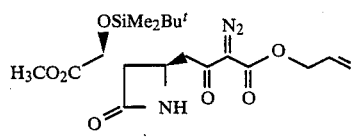

In step [G], the compounds of the formula (XIII) are prepared from the compounds (XII) by cleaving off the hydroxyl-protecting group by conventional methods, as described, for example, by A. Yoshida et al. in tetrahedron Lett. 1984, 2793.

The ring closure of compounds (XIII) to form compounds (II) in step [H] is carried out by conventional methods with the aid of catalysts, such as acid, metal powder or metal salts, preferably noble metals or seminoble metals, or the salts thereof, in inert organic solvents, such as ethers, for example diethyl ether, dioxane or tetrahydrofuran, or hydrocarbons, for example benzene, toluene, xylene or petroleum fractions, or halogenated hydrocarbons, for example methylene chloride, chloroform or carbon tetrachloride, at temperatures from 0° C. to 150° C., preferably from 20° C. to 100° C., as described, for example, by D. H. Shih et al., in Heterocycles 21, 29 (1984).

The ring closure is particularly preferably carried out using rhodium(II) acetate in boiling methylene chloride.

The compounds of the general formula (XI) are known or can be prepared by methods which are known from the literature [cf. S. Julia et al., Compt. Rend. Acad. Sci., Paris, Section C 246, 1890 (1967), European Patent Application 78,026, European Patent 52,299, and R. M. Kellogg et al., J.C.S. Chem. Commun. (1977) 932].

The epoxides of the general formula V employed as starting materials are new and can be prepared by known methods according to the following equation:

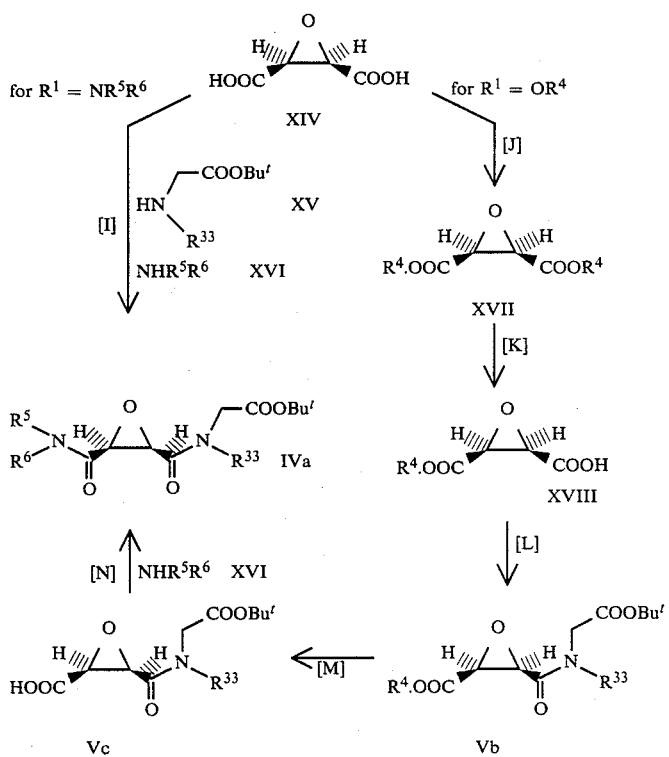

in which $R^5$, $R^6$ and $R^{33}$ have the meaning already specified, and $R^{4'}$ has the meaning of $R^4$, but does not represent H.

Accordingly, for the preparation of the starting materials having $R' = NR^5R^6$ (formula Va), 2,3-oxiranedicarboxylic acid (XIV), if appropriate after activation of the carboxyl groups by conversion into a mixed anhydride, for example using pivaloyl chloride or ethyl or isobutyl chloroformate, after conversion into the mesylate by means of methanesulphonyl chloride, or after conversion into an activated ester, for example using 1-hydroxybenzotriazole or dicyclohexylcarbodiimide, is reacted, in step [I], with an amine (XV) and an amine (XVI)—in the specified or reverse sequence—if appropriate in the presence of a condensing agent, such as carbodiimides, as described, for example, by M. Shiozaki et al. In Tetrahydron 40 1795 (1984).

The reaction is particularly preferably carried out in the presence of condensing agents, such as carbodiimides, for example dicyclohexylcarbodiimide, or by activation using 1-hydroxybenztriazole or with cyclohexylcarbodiimide, in inert organic solvents, such as ethers, for example diethyl ether, dioxane or tetrahydrofuran, or halogenated hydrocarbons, for example methylene chloride, chloroform or carbon tetrachloride, or dimethylformamide.

In the reaction of (XIV) with carbodiimides, compounds of the formula (Vd), having $R^1 = -NR^4CONR^5R^6$, are generally also obtained under reaction conditions which are otherwise identical.

The compounds (Vb), having $R^1 = OR^4$, are prepared according to the equation shown above via the process steps [J]–[L]. During this, the 2,3-oxiranedicarboxylic acid (XIV) is initially converted, in step [J], to the diester (XVII) by known methods, the diester (XVII) is subsequently converted, in step [K], enzymatically into the monoester (XVIII), which is reacted in step [L] with glycines (XV) under the conditions already specified [step I] to form the azetidinones (Vb).

The compounds (Ve) may alternatively be prepared by hydrolysis of the esters (Vb) to form the monocarboxylic acids (Vc) (Step M) and subsequent reaction of the acids (Vc) with amines (XVI) (Step N) under the conditions which have already been described for step I.

The individual process steps may be carried out, for example, as described by M. Schneider et al. in Angew. Chem. 96, 55 (1984), by M. Shiozaki et al. in Tetrahedron 40, 1795 (1985) or in Jpn, Kokai Tokyo Koho 80 85577.

The compounds according to the invention exhibit a broad antibacterial spectrum against Gram-positive and Gram-negative germs, particularly against Enterobacteriaceae, coupled with low toxicity; they are above all active against those which are resistant towards various antibiotics, such as, for example, penicillins, cephalosporins, aminoglycosides, sulphonamides, and tetracyclines. Surprisingly, the carbapenems, according to the invention, of the formula (I), exhibit particularly good metabolic stability towards the enzyme dehydropeptidase I (DHP I) and are thus superior to other compounds of this class of substance with respect to the tolerance.

These valuable properties permit their use as chemotherapeutic active compounds in medicine and as compounds for preserving inorganic and organic materials, in particular organic materials of all kinds, for example polymers, lubricants, paints, fibers, leather, paper and timber, foodstuffs and water.

The compounds according to the invention are active against a very broad spectrum of microorganisms. They can be used to combat Gram-negative and Gram-positive and bacteria-like microorganisms and to prevent, ameliorate and/or heal illnesses caused by these pathogens.

The compounds according to the invention are particularly active against bacteria and bacteria-like microorganisms. They are therefore particularly suitable for the prophylaxis and chemotherapy of local and systemic infections, caused by these pathogens, in human medicine and veterinary medicine.

For example, local and/or systemic illnesses caused by the following pathogens or by mixtures of the following pathogens can be treated and/or prevented:

Gram-positive cocci, for example Staphylococci (*Staph. aureus* and *Staph. epidermidis*) and Streptococci (*Strept. agalactiae, Strept. faecalis, Strept. pneumoniae* and *Strept. pyogenes*); Gram-negative cocci (*Neisseria gonorrhoeae*) and Gram-negative bacilli, such as Enterobacteriacia, for example *Escherichia coli, Haemophilus influenzae, Citrobacter (Citrob. freundii* and *Citrob. divernis*). Salmonella and Shigella; furthermore Klebsiellen (*Klebs. pneumoniae* and *Klebs. oxytoca*), Enterobacter (*Ent. aerogenes* and *Ent. agglomerans*), Hafnia, Serratia (*Serr. marcescens*), Proteus (*Pr. mirabilis, Pr. rettgeri* and *Pr. vulgaris*), Providencia, Yersinia and the *Acinetobacter* genus. In addition, the antibacterial spectrum covers the Pseudomonas genus (*Ps. aeruginosa* and *Ps. maltophilia*) and strictly anaerobic bacteria, such as, for example, *Bacteroides fragilis*, representatives of the peptococcus genus, peptostreptococcus and the Clostridium genus; furthermore Mycoplasma (*M. pneumoniae, M. hominis* and *M. urealyticum*) and Mykobacteria, for example *Mycobacterium tuberculosis*.

The above list of pathogens is purely illustrative and is in no way to be interpreted as restrictive. The following may be mentioned as examples of illnesses which can be prevented, ameliorated and/or healed by the active compounds according to the invention:

Infectious illnesses in humans, such as, for example, otitis, pharyngitis, pneumonia, peritonitis, pyelonephritis, cystitis, endocarditis, systemic infections, bronchitis (acute and chronic), septic infections, illnesses of the upper respiratory tracts, diffuse panbronchiolitis, pulmonary emphysema, dysentery, enteritis, liver abscesses, urethritis, prostatitis, epididymitis, gastro-intestinal infections, bone and joint infections, cystic fibrosis, skin infections, postoperative wound infections, abscesses, phlegmon, wound infections, infected burns, burn wounds, oral infections, infections after dental operations, osteomyelitis, septic arthritis, cholecystitis, peritonitis with appendicitis, cholangitis, intraabdominal abscesses, pancreatitis, sinusitis, mastoiditis, mastitis, tonsillitis, typhoid, meningitis and infections of the nervous system, salpingitis, endometritis, genital infections, pelveoperitonitis and eye infections.

Apart from in humans, bacterial infections can also be treated in other species. Examples which may be mentioned are:

Pig: coli-diarrhoea, enterotoxaemia, sepsis, dysentery, salmonellosis, metritis-mastitis-agalactiae syndrome and mastitis;

Ruminants (cattle, sheep and goat): diarrhoea, sepsis, bronchopneumonia, salmonellosis, pasteurellosis, mycoplasmosis and genital infections;

Horse: bronchopneumonia, joint-ill, puerperal and postpuerperal infections, and salmonellosis;

Dog and cat: bronchopneumonia, diarrhoea, dermatitis, otitis, urinary tract infections and prostatitis;

Poultry (chicken, turkey, quail, dove, cage birds and others): mycoplasmosis, *E. coli* infections, chronic respiratory tract illnesses, salmonellosis, pasteurellosis and psittacosis.

Bacterial infections in the breeding and keeping of productive and ornamental fish can likewise be treated, the antibacterial spectrum extending beyond the previously mentioned pathogens to further pathogens, such as, for example, Pasteurella, Brucella, Campylobacter, Listeria, Erysipelothrix, Corynebacteria, Borellia, Treponema, Nocardia, Rikettsia, Yersinia.

The present invention includes pharmaceutical preparations which, in addition to non-toxic, inert pharmaceutically suitable excipients, contain one or more compounds according to the invention or which comprise one or more active compounds according to the invention, and processes for the production of these preparations.

The present invention also includes pharmaceutical preparations in dosage units. This means that the preparation are in the form of individual parts, for example tablets, dragees, capsules, pills, suppositories and ampules, of which the content of active substance corresponds to a fraction or a multiple of an individual dose. The dosage units can contain, for example, 1, 2, 3 or 4 individual doses ½, ⅓ or ¼ of an individual dose. An individual dose preferably contains the amount of active compound which is given in one administration and which usually corresponds to a whole, a half or a third or a quarter of a daily dose.

Non-toxic, inert pharmaceutically suitable excipients are taken to mean solid, semisolid or liquid diluents, fillers and formulation auxiliaries of all kinds.

Tablets, dragees, capsules, pills, granules, suppositories, solutions, suspensions and emulsions, pastes, ointments, gels, creams, lotions, powders and sprays may be mentioned as preferred pharmaceutical preparations.

Tablets, dragees, capsules, pills and granules can contain the active compound or compounds together with the customary excipients such as (a) fillers and extenders, for example starches, lactose, sucrose, glucose, mannitol and silica, (b) binders, for example carboxymethycellulose, alginates, gelatin and polyvinylpyrrolidone, (c) humectants, for example glycerine, (d) disintegrating agents, for example agar-agar, calcium carbonate and sodium bicarbonate, carbonate, (e) solution retarders, for example paraffin, and (f) absorption accelerators, for example quaternary ammonium compounds, (g) wetting agents, for example cetyl alcohol or glycerine monostearate, (h) adsorbents, for example kaolin and bentonite, and (i) lubricants, for example talc, calcium stearate and magnesium stearate and solid polyethylene glycols, or mixtures of the substances listed under (a) to (i).

The tablets, dragees, capsules, pills and granules can be provided with the customary coatings and shells, optionally containing opacifying agents, and can also be of such composition that they release the active compound or compounds only, or preferentially, in a certain part of the intestinal tract optionally in a delayed manner, examples of embedding compositions which can be used being polymer substances and waxes.

The active compound or compounds, optionally together with one or more of the abovementiond excipients, can also be in a microencapsulated form.

Suppositories can contain, in addition to the active compound or compounds, the customary water-soluble or water-insoluble excipients, for example polyethylene glycols, fats, for example cocoa fat, and higher esters (for example $C_{14}$-alcohol with $C_{16}$-fatty acid) or mixtures of these substances.

Ointments, pastes, creasms and gels can contain the customary excipients in addition to the active compound or compounds, for example animal and vegetable fats, waxes, paraffins, starch, tragacanth, cellulose derivatives, polyethylene glycol, silicones, bentonites, silica, talc and zinc oxide or mixtures of these substances.

Powders and sprays can contain the customary excipients in addition to the active compound or compounds, for example lactose, talc, silica, aluminum hydroxide, calcium silicate and polyamide powders or mixture of these substances. Sprays can additionally contain the customary propellants, for example chlorofluorohydrocarbons.

Solutions and emulsions can contain the customary excipients in addition to the active compound or compounds, such as solvents, solubilising agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, corn germ oil, olive oil, castor oil and sesame oil, glycerine, glycerine-formal, tetrahydrofurfuryl alcohol, polyethylene glycols and fatty acid esters of sorbitan, or mixtures of these substances.

For parenteral administration, the solutions and emulsions can also be in a sterile form which is isotonic with blood.

Suspensions can contain the customary excipients in addition to the active compound or compounds, such as liquid diluents, for example water, ethyl alcohol or propylene alcohol, suspending agents, for example ethoxylated isostearyl alcohols, polyoxyethylene sorbitol esters and polyoxyethylene sorbitan esters, microcrystalline cellulose, aluminum metahydroxide, bentonite, agar-agar tragacanth, or mixtures of these substances.

The formulation forms mentioned can also contain dyestuffs, preservatives and additives which improve the odour and flavour, for example peppermint oil and eucalyptus oil and sweeteners, for example saccharin.

The therapeutically active compounds should preferably be present in the abovementioned pharmaceutical preparations in a concentration of about 0.1 to 99.5, preferably of about 0.5 to 95, % by weight of the total mixture.

The abovementioned pharmaceutical preparations can also contain other pharmaceutically active compounds in addition to compounds according to the invention.

The abovementioned pharmaceutical preparations are manufactured in the usual manner according to known methods, for example by mixing the active compound or the active compounds with the excipient or excipients.

In humans and animals, the preparations mentioned can be administered either orally, rectally, parenterally (intravenously, intramuscularly or subcutaneously), intracisternally, intravaginally, intraperitoneally, locally (powder, ointment or drops) and for therapy of infections in cavities and body cavities. Suitable preparations are injection solutions, solutions and suspensions for oral therapy, gels, pour-on formulations, emulsions, ointments or drops. Ophthalmological and dermatological formulations, silver salts and other salts, ear drops, eye ointments, powders or solutions can be used for local therapy. In the case of animals, intake can also be effected in suitable formulations via the feed or drinking water. Furthermore, gels, oral powders, dusting powders, tablets, retard tablets, premixes, concentrates, granules, pellets, tablets, boli, capsules, aerosols, sprays and inhalants may be used in humans and animals. Furthermore, the compounds according to the invention can be incorporated into other excipient materials, such as, for example, plastics, (plastic chains for local therapy), collagen or bone cement.

In general, it has proved advantageous, both in human medicine and veterinary medicine, to administer the active compound or compounds in total amounts of about 0.5 to about 500, preferably 5 to 100 mg/kg of body weight every 24 hours, if appropriate in the form of several individual administrations, in order to achieve the desired results. An individual administration contains the active compound or the active compounds preferably in amounts of about 1 to about 80, particularly 3 to 30, mg/kg of body weight. However, it may be necessary to deviate from the dosages mentioned and in particular to do so as a function of the nature and the body weight of the subject to be treated, the nature and severity of the illness, the nature of the preparation and of the administration of the medicament, and the time or interval over which the administration takes place.

Thus, it may suffice, in some cases, to manage with less than the abovementioned amount of active compound, whilst in other cases, the abovementioned amount of active compound must be exceeded. The particular optimum dosage required and the type of administration of the active compounds can easily be decided by anyone skilled in the art, on the basis of his expert knowledge.

The new compounds can be administered, in the usual concentrations and preparations, together with the feedstuff or the feedstuff preparations, or with the drinking water. This permits infection by Gram-negative or Gram-positive bacteria to be prevented, ameliorated and/or healed, and thereby allows promotion of growth and improved utilization of the feedstuff to be achieved.

The MIC values of some of the compounds according to the invention are given in the following table, comparing with ciprofloxacin.

Antibacterial action:

The agar solution method was used for determining the antibacterial action, an Iso-sensitest agar being used and the minimum inhibitory concentration (MIC) of the sample being expressed in μg/ml of the nutrient medium (Table).

TABLE

| MIC (μg/ml) for the compound from Example 14 | |
|---|---|
| Germ | MIC |
| Staph. 133 | 0.5 |
| " 24455 | 0.5 |
| " E 25185 | 1.0 |

EXAMPLE FOR A TABLET ACCORDING TO THE INVENTION

Each tablet contains:

| Compound of Example 14 | 583.0 mg |
|---|---|
| Microcrystalline cellulose | 55.0 mg |
| Corn starch | 72.0 mg |
| Poly-(1-vinyl-2-pyrrolidone) insoluble | 30.0 mg |
| Highly disperse silicon dioxide | 5.0 mg |
| Magnesium stearate | 5.0 mg |
| | 750.0 mg |

The lacquer coating contains:

| Poly-(O—hydroxypropyl-O—methyl)-cellulose 15 cp | 6.0 mg |
|---|---|
| Macrogol 4000 rec. INN Polyethylene glycols (DAB) | 2.0 mg |
| Titanium (IV) oxide | 2.0 mg |
| | 10.0 mg |

PREPARATION EXAMPLES

Example 1

Dimethyl 2,3-oxiranedicarboxylate

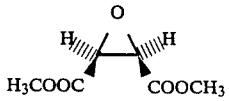

A solution of 247.0 g (1.87 mol) of cis-2.3-oxiranedicarboxylic acid [G. B. Payne et al. J. Org. Chem., 24, 54 (1959)] and 5 ml (94 mmol—0.05 equiv.) of 96% strength sulphuric acid in 1.5 liters of methanol were refluxed in circulation through a Soxhlet extractor, filled with 100 g of dry molecular sieve (3 Å) for 22 hours. After cooling, the reaction solution was stirred into a mixture of ice-cold NaHCO₃ solution and ether, extracted several times with ether, washed with NaCl solution, and dried over MgSO₄. After evaporation of the solvent in vacuo, 200.6 g (67% of theory) of the title compound were obtained as an oil.

Boiling point: 112° C./1 mm.

$^1$H NMR (300 MHz, CDCl₃) δ=3.72 (s, 2H, CH), 3.81 (s, 6H, COOCH₃).

C₆H₈O₅ (160.1) Calc.: C 45.01, H 5.04, Found: C 44.6, H 5.3.

Example 2

Monomethyl (2R,3S)-2,3-oxiranedicarboxylate

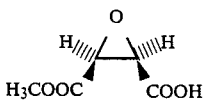

1000 units (about 10 mg) of pig liver esterase are added, with stirring, to a solution of 16.0 g (0.1 mol) of dimethyl 2,3-oxiranedicarboxylate in 100 ml of phosphate buffer (0.1M, pH 7). The mixture was stirred at room temperature for 20 hours, the pH being kept constant by addition of a 1N NaOH from an automatic titrator. After addition of 100 ml (0.1 mol) of NaOH, the mixture was cooled and the pH adjusted to 2, with stirring, using 5N H₂SO₄. The solution was saturated with solid NaCl and extracted to exhaustion with ethyl acetate. After drying the organic phase using MgSO₄ and evaporating the solvent in vacuo, 7.74 g (53% of theory) of the title compound were obtained as a mixture of enantiomers in the ratio 3:2 [determined by NMR spectroscopy by addition of (R)-(+)-1-phenethylamine to the crude product as the ratio of the CH₃ signals at δ 3.60 (s) and 3.63 (s)].

Boiling point: about 150° C./1.5 mm (Kugelrohr)

$[\alpha]_D^{20} = -3.45°$ (c=0.489 in CHCl₃).

C₅H₆O₅ (146.1) Calc.: C 41.11, H 4.14, Found: C 40.8, H 4.4.

EXAMPLE 3

(2R, 3S)-N-(t-butoxycarbonylmethyl)-N-(4-methoxyphenyl)-3-methoxycarbonyl-2,3-epoxypropionamide

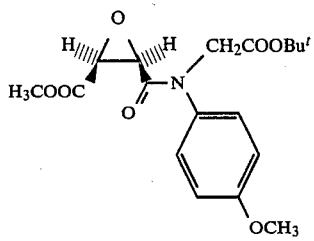

A solution of 188.0 g (0.88 mol) of dicyclohexylcarbodiimide in 300 ml of THF was added dropwise, within 15 minutes, to a solution of 129.0 g (0.88 mol) of monomethyl (2R,2S)-2,3-oxirandicarboxylate and 196.0 g (0.8 mol) of t-butyl-N-(4-methoxyphenyl)glycinate [M. Shiozaki et al., Tetrahedron 40, 1795, (1984)] in 1100 ml of THF. The mixture was subsequently stirred for a further 30 minutes at room temperature, the resultant precipitate was separated off by filtration, and the filtrate solution was evaporated in vacuo. After purification of the product on 1.8 kg of silica gel (toluene-:ethyl acetate=7:3), 263.2 g (90% of theory) of the title compound were obtained as crystals, melting point: 89° C. $[\alpha]_D^{20} = -21.78°$ (c=0.435 in CHCl$_3$). The enantiomer ratio, of 3:2, determined in the preparation example was confirmed by NMR-shift experiments using Eu(TFC)$_3$.

IR (CHCl$_3$) 1737 (C=O, ester) 1681 (C=O, amide) 1509 cm$^{-1}$.

$^1$H NMR (250 MHz, CDCl$_3$): δ=1.44 (s, 9H, CH$_3$—C); 3.46 and 3.51 (AB, J=4.5 Hz, 2H, Oxirane-H); 3.82 (s, 6H, OCH$_3$, COOCH$_3$); 4.08 and 4.36 (AB, J=16 Hz, CH$_2$COO); 6.91 and 7.31 (AB, J=9 Hz, 4H, p—H$_3$CO—C$_6$H$_4$).

EXAMPLE 4

(3S,4S)-4-t-butoxycarbonyl-3-[(1S)-1-hydroxy-1-methoxycarbonyl]methyl-1-(4-methoxyphenyl)azetidin-2-one

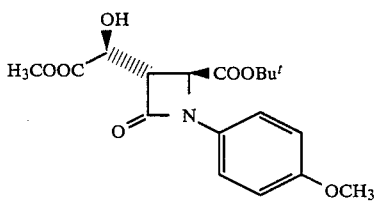

A solution of 4.19 g (11.5 mol) of (2R,3S)-N-(t-butoxycarbonylmethyl)-N-(4-methoxyphenyl)-3-methoxycarbonyl-2,3-epoxypropionamide in 12 ml of THF was added dropwise to a mixture, cooled to 0° C., of 12.6 mmol (1.1 equiv.) of tetrabutylammonium fluoride and 6 g of molecular sieve (4A) in 25 ml of THF. The mixture was filtered after 1.2 hours at 0° C. Toluene was added to the filtrate solution, and the THF was separated off in vacuo. The toluene solution which remained was washed several times with water and dried over MgSO$_4$. After evaporation of the solvent in vacuo and chromatography of the crude product on 150 g of silica gel (toluene:ethyl acetate=4:1), 2.44 g (58% of theory) of the title compound were obtained as crystals, melting point: 82° C., R$_f$=0.21 (toluene:ethyl acetate=7:3).

IR (KBr) 3425, 1758, 1740, 1516 cm$^{-1}$.

$^1$H NMR (250 MHz, CDCl$_3$): δ=1.45 (s, 9H, CH$_3$—C), 3.24 (d, J=4 Hz, 1H, OH); 3.75 (dd, J=3 Hz, 2.5 Hz, H-3); 3.78 (S, 3H, OCH$_3$); 3.86 (S, 3H, COOCH$_3$); 4.46 (d, J=2.5 Hz, 1H, H-4); 4.75 (dd, J=4 Hz, 3 Hz, CH—COOCH$_3$); 6.85 and 7.25 (AB, J=9 Hz, 4H, p—H$_3$CO—C$_6$H$_4$).

MS (70 eV) m/e=365 (M$^+$); calc. 365.4.

EXAMPLE 5

(3S, 4S)-4-carboxy-3-[(1S)-1-hydroxy-1-methoxycarbonyl]methyl-1-(4-methoxyphenyl)azetidin-2-one

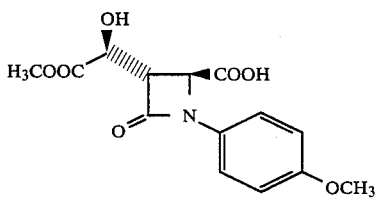

23 ml of trifluoroacetic acid were added at room temperature to a solution of 6.49 g (17.8 mmol) of (3S, 4S)-4-t-butoxycarbonyl-3-[(1S)-1-hydroxy-1-methoxycarbonyl]methyl-1-(4-methoxyphenyl)azetidin-2-one in 23 ml of dichloromethane. After 3 hours, the solution was evaporated in vacuo, toluene was added, and the mixture was re-evaporated. This procedure was repeated twice further, and the crystalline residue was then stirred with ether, filtered off under suction and dried in a high vacuum over P$_4$O$_{10}$. 4.52 g (82% of theory) of the title compound were obtained as colorless crystals, melting point: 147° C.

IR(KBr) 1755, 1729, 1517, 1298 cm$^{-1}$.

$^1$H NMR (250 MHz, DMSO): δ=3.68 (s, OCH$_3$), 3.73 (s, COOCH$_3$); 3.72 (m, H-3) together 7H, 4.51 (d, J=2.5 Hz, 1H, H-4); 4.58 (d, J=3 Hz, 1H, CH—COOCH$_3$); 6.96 and 7.95 (AB, J=9 Hz, 4H, p—H$_3$CO—C$_6$H$_4$).

EXAMPLE 6

(3R, 4R)-4-acetoxy-3-[(1S)-1-hydroxy-1-methoxycarbonyl]methyl-1-(4-methoxyphenyl)azetidin-2-one

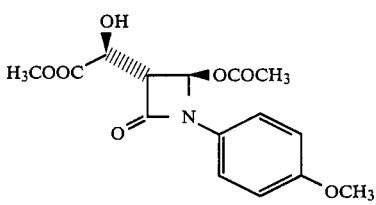

6.27 g (14.2 mmol) of lead tetraacetate were added to a solution of 4.38 g (14.2 mmol) of (3S, 4S)-4-carboxy-3-[(1S)-1-hydroxy-1-methoxycarbonyl]methyl-1-(4-methoxyphenyl)azetidin-2-one in 30 ml of DMF and 8 ml of glacial acetic acid, and the mixture was heated for exactly 7 minutes in an oil bath, preheated to 60° C. The mixture was then cooled and poured into a mixture of water, NaCl solution and ethyl acetate. It was extracted with ethyl acetate (4×) and the organic extracts were washed with water (3×) and NaHCO3 solution until neutral, and dried using MgSO4. After evaporation of the solvent in vacuo, 2.20 g (47% of theory) of the title compound were obtained as colorless crystals, melting point: 138° C., $R_f$=0.35 (toluene:ethyl acetate=1:1).

IR(KBr) 3404 (OH), 1755 (C=O, β-lactam), 1737 (C=O, ester), 1517 cm$^{-1}$.

$^1$HNMR (200 MHz, CDCl3): δ=2.13 (s, 3H, OCOCH3); 3.33 (bs, 1H, OH); 3.62 (dd, J=2 Hz, 1 Hz, 1H, H-3); 3.78 (s, 3H, COOCH3); 3.85 (s, 3H, OCH3); 4.65 (d, J=2 Hz, 1H, CH—COOCH3); 6.18 (d, J=1 Hz, 1H, H-4); 6.85 and 7.33 (AB, J=9 Hz, 4H, p—H3CO—C6H4).

EXAMPLE 7

(3R, 4R)-4-acetoxy-3-[(1S)-1-t-butyldimethylsilyloxy-1-methoxycarbonyl]methyl-1-(4-methoxyphenyl)azetidin-2-one

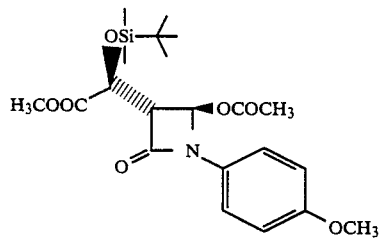

4.32 g (35.4 mmol-1.15 equiv.) of dimethylaminopyridine were added to a solution of 10.29 g (30.8 mmol) of (3R, 4R)-4-acetoxy-3-[(1S)-1-hydroxy-1-methoxycarbonyl]methyl-1-(4-methoxyphenyl)azetidin-2-one and 5.10 g (33.9 mmol-1.1 equiv.) of t-butyldimethylsilyl chloride in 30 ml of DMF, and the mixture was stirred for 22 hours at room temperature. The mixture was worked up by pouring into a mixture of cold 1N HCl and ethyl acetate, extracting with ethyl acetate (2×), washing the extracts with water and NaHCO3 solution, and drying over MgSO4. After evaporation of the solvent in vacuo, 11.61 g (86% of theory) of the title compound were obtained as colorless crystals, melting point: 102° C., $R_f$=0.33 (toluene:ethyl acetate=9:1).

IR(KBr) 1759, 1734, 1516, 1246 cm$^{-1}$.

$^1$H NMR (200 MHz, CDCl3): δ=0.01 and 0.10 (s, je 3H, CH3Si); 0.75 (s, 9H, CH3—C—Si); 2.08 (s, 3H, OCOCH3); 3.60 (dd, J=2 Hz, 0.5 Hz, 1H, H-3); 3.76 (S, 6H, OCH3, COOCH3); 4.63 (d, J=2 Hz, 1H, CH—COOCH3); 6.35 (d, J=0.5 Hz, 1H, H-4); 6.83 and 7.30 (AB, J=9 Hz, 4H, p—H3CO—C6H4).

MS (CI, 150 eV, NH3): m/e=438 (M+H), 455 (M+NH4).

EXAMPLE 8

(3R, 4R)-4-acetoxy-3-[(1S)-t-butyldimethylsilyloxy-1-methoxycarbonyl]methyl-azetidin-2-one

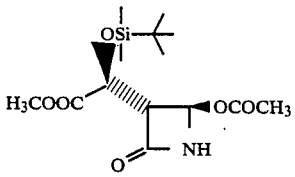

A solution of 5.94 g (10.8 mol-3 equiv.) of ammonium cerium(IV) nitrate in 21 ml of water was added slowly to a solution, cooled to 0° C., of 1.58 g (3.64 mmol) of (3R, 4R)-4-acetoxy-3-[(1S)-1-t-butyldimethylsilyloxy-1-methoxycarbonyl]methyl-1-(4-methoxyphenyl)azetidin-2-one in 18 ml of acetonitrile at a rate such that the internal temperature did not exceed +5° C. The mixture was subsequently stirred at 0° C. for 30 minutes and poured into a mixture of NaCl and NaHCO3 solution and ethyl acetate. The mixture was extracted with ethyl acetate, washed with NaHCO3 and NaCl solution and dried over MgSO4. After evaporation of the solvent in vacuo and chromatography of the residue on 50 g of silica gel (toluene:ethyl acetate=4:1), 930 mg (78% of theory) of the title compound were obtained.

$R_f$=0.24 (toluene:ethyl acetate=4:1)
IR(KBr) 3344, 1791, 1750, 1731 cm$^{-1}$.

$^1$H NMR (200 MHz, CDCl3): δ0.03 and 0.05 (s, 6H, CH3—Si); 0.88 (s, 9H, CH3—C—Si); 2.04 (s, 3H, OCOCH3); 3.57 (dd, J=2 Hz, 1 Hz, H-3); 3.76 (s, 3H, COOCH3); 4.57 (d, J=2 Hz, 1H; CH—COOCH3); 5.83 (d, J=1 Hz, 1H, H-4); 6.51 (bs, 1H, NH).

EXAMPLE 9

4-Nitrobenzyl 2-diazo-3-oxo-butanoate

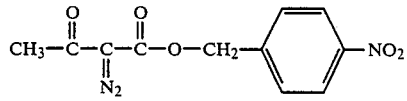

35.0 ml (0.25 mol-1.8 equiv.) of triethylamine were added dropwise to a solution, cooled to 0° C., of 33.18 g (0.14 mol) of 4-nitrobenzyl acetoacetate and 30.40 g (0.15 mol) of p-toluenesulphonyl azide in 280 ml of anhydrous acetonitrile. The mixture was stirred at 0° C. for 2 hours, and the resultant precipitate was then filtered off under suction, washed with ether and dried in a high vacuum over P4O10. 20.3 g (55% of theory) of the title compound were obtained as colorless crystals, melting point: 132° C. A further 6.3 g (17% of theory) of the title compound were obtained by chromatography of the filtrate solution on 400 g of silica gel (toluene:ethyl acetate=9:1), $R_f$=0.35 (toluene:ethyl acetate=9:1).

IR(KBr) 2144 (N2), 1709 (C=O), 1662 (C=O), 1514 (NO2 asym.), 1343 cm$^{-1}$ (NO2 sym.).

$^1$H NMR (200 MHz, DMSO): δ=2.44 (s, 3H, CH3); 5.44 (s, 2H, CH2); 7.72 (d, J=9 Hz, 2H, H$_{arom}$).; 8.28 (d, J=9 Hz, 2H, H$_{arom}$).

$C_{11}H_9N_3O_5$ (263.2) Calc.: C 50.20, H 3.45, N 15.96, Found: C 50.2, H 3.4, N 15.9.

EXAMPLE 10

(3S, 4R)-3-[(1S)-1-t-butyldimethylsilyloxy-1-methoxycarbonyl]methyl-4-(3-p-nitrobenzyloxycarbonyl-3-diazo-2-oxopropyl)-azetidin-2-one

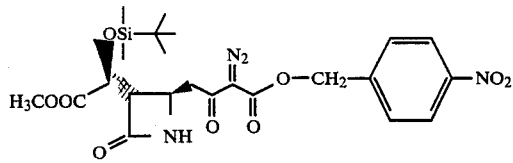

4.74 ml (34.2 mmol) of triethylamine and then, dropwise, 6.08 ml (31.4 mmol) of trimethylsilyl trifluoromethanesulphonate were added to a solution, cooled to 0° C., of 4.53 g (13.7 mmol) of (3R, 4R)-4-acetoxy-3-[(1S)-1-t-butyldimethylsilyloxy-1-methoxycarbonyl]methyl-azetidin-2-one and 4.31 g (16.4 mmol) of 4-nitrobenzyl 2-diazo-3-oxo-butanoate in 125 ml of anhydrous dichloromethane. The cooling bath was removed, the mixture was stirred for 15 minutes at room temperature, 0.79 ml (4.1 mmol) of trimethylsilyl trifluoromethanesulphonate were added, and the mixture was stirred for a further 15 minutes at room temperature. The reaction solution was then poured into a mixture of cold, saturated NaHCO3 solution and ethyl acetate and extracted with ethyl acetate, and the organic extracts were washed with saturated NaCl solution and dried over MgSO4. The solvent was evaporated in vacuo and the residue was chromatographed on 450 g of silica gel (toluene:ethyl acetate=4:1). 4.70 g (64% of theory) of the title compound were obtained, $R_f$=0.40 (toluene:ethyl acetate=1:1).

IR(KBr) 2138, 1758, 1725, 1656, 1526, 1349 cm$^{-1}$.

$^1$H NMR (250 MHz, CDCl3): δ=0.09 and 0.10 (s, 6H, CH3—Si); 0.90 (s, 9H, CH3—C—Si); 3.04 (dd, J=17 Hz, 1H, H-1); 3.26 (m, H-3); 3.27 (dd, J=17 Hz, 4.5 Hz, H-1); together 2H, 3.74 (s, 3H, COOCH3); 4.18 (m, 1H, H-4); 4.59 (d, J=2.5 Hz, 1H, CH—COOCH3); 5.34 (s, 2H, COOCH2); 6.05 (s, 1H, NH); 7.50 and 8.23 (AB, J=9 Hz, 4H, p—NO2—C6H4).

EXAMPLE 11

(3S, 4R)-3-[(1S)-1-hydroxy-1-methoxycarbonyl]methyl-4-[3-diazo-3-p-nitrobenzyloxycarbonyl-2-oxopropyl]-azetidin-2-one

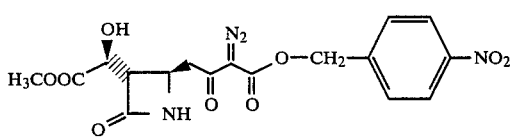

3.92 g (7.33 mmol) of (3S, 4R)-3-[1-(1S)-1-hydroxy-1-methoxycarbonyl]methyl-4-[3-diazo-3-p-nitrobenzyloxycarbonyl-2-oxopropyl]-azetidin-2-one were dissolved at 0° C. in 20 ml of a standard solution of 1.80 ml (14.7 mmol-2 equiv.) of boron trifluoride etherate in acetonitrile, and stirred for 1 hour at this temperature. The reaction solution was then stirred into a cold mixture of NaHCO3 solution and ethyl acetate. The mixture was extracted with ethyl acetate, and the organic extracts were washed with saturated NaCl solution and dried over MgSO4. After evaporation of the solvent in vacuo and chromatography of the crude product on 50 g of silica gel (toluene:ethyl acetate=1:4). 2.73 g (89% of theory) of the title compound were obtained as a solid, $R_f$=0.18 (toluene:ethyl acetate=1:4).

IR(KBr) 3326 (OH), 2135 (N2), 1758 (C=O, β-lactam), 1744, 1725, 1658 cm$^{-1}$.

$^1$H NMR (200 MHz, CDCl3): δ=3.1—3.3 (m, 4H, H-1, H-3, OH); 3.83 (s, 3H, COOCH3); 4.01 (m, 1H, H-4); 4.62 (m, 1H, CH—COOCH3); 5.34 (s, 2H, COOCH2); 6.09 (bs, 1H, NH); 7.50 and 8.23 (AB, J=9 Hz, 4H, p—NO2—C6H4).

EXAMPLE 12

(2S, 5R, 6S)-3,7-dioxo-6-[(1-hydroxy-1-methoxycarbonyl]methyl-2-p-nitrobenzyloxycarbonyl-1-azabicyclo[3.2.0]heptane

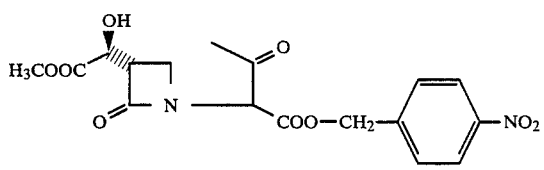

A solution of 2.73 g (6.5 mmol) of (3S, 4R)-3-[(1S)-1-hydroxy-1-methoxycarbonyl]methyl-4-[3-p-nitrobenzyloxycarbonyl-3-diazo-2-oxopropyl]-azetidin-2-one in 50 ml of anhydrous dichloromethane was refluxed for 30 minutes in the presence of 85 mg (3 mol %) of rhodium(II) acetate. The reaction solution was filtered through a little kieselguhr and evaporated in vacuo. 1.45 g (57% of theory) of the title compound were obtained as colorless crystals, melting point: 169° C., $R_f$=0.41 (toluene:ethyl acetate=3:7).

IR(KBr) 3460 (OH), 1760 (C=O, β-lactam), 1744 (C=O, ester), 1519 (NO2, asym.), 1350 cm$^{-1}$ (NO2, sym.).

$^1$H NMR (200 MHz, CDCl3): δ=2.46 (dd, J=19 Hz, 7.5 Hz, 1H, H-1); 2.88 (dd, J=19 Hz, 6 Hz, 1H, H-1); 3.23 (d, J=5 Hz, 1H, OH); 3.58 (dd, J=5 Hz, 2.5 Hz, 1H, H-6); 3.85 (s, 3H, COOCH3); 4.14 (ddd, J=7.5 Hz, 6 Hz, 2.5 Hz, 1H, H-5); 4.69 (m, 1H, CH—COOCH3); 4.76 (s, 1H, H-3); 5.21 and 5.33 (AB, J=12.5 Hz, 2H, COOCH2); 7.49 and 8.21 (AB, J=8.5 Hz, 4H, p—NO2—C6H4).

MS: m/e (FAB) 393 (M+H).

C17H16N2O9 (392.3) Calc.: C 52.05, H 4.11, N 7.14, Found: C 52.0, H 4.1, N 7.0.

EXAMPLE 13 p-nitrobenzyl (5R,6S)-6-[(1S)-1-hydroxy-1-methoxycarbonyl]methyl-7-oxo-3-(4-pyridinylthio)-1-azabicyclo[3.2.0]hept-2-en-2-carboxylate

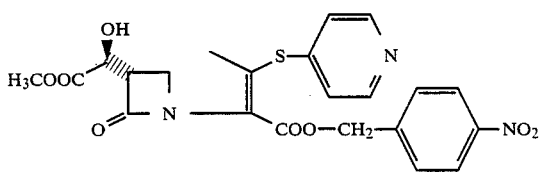

0.3 ml (1.73 mmol-1.05 equiv.) of ethyldiisopropylamine and 0.36 ml (1.73 mmol) of diphenyl chlorophosphate were added simultaneously, within 10 minutes, to a solution, cooled to 0° C. of 645 mg (1.64 mmol) of (2S, 5R,6S)-3,7-dioxo-6-[(1S)-1-hydroxy-1-methoxycarbonyl]methyl-2-p-nitrobenzyloxycarbonyl-1-azabicyclo[3.2.0]-heptane in 8 ml of anhydrous acetonitrile. The mixture was then stirred for 15 minutes at 0° C. and cooled to −40° C., and 0.32 ml (1.81 mmol·1.1 equiv.) of ethyldiisopropylamine and 201 mg (1.81 mmol) of 4-mercaptopyridine were added successively. The reaction mixture was allowed to warm to 0° C., and was then stirred into a cold mixture of NaHCO$_3$ solution and ethyl acetate. The mixture was extracted with ethyl acetate, washed with NaCl solution and water, and dried over MgSO$_4$. After evaporation of the solvent in vacuo and chromatography of the residue on 100 g of silica gel (ethyl acetate:acetone=95:5), 208 mg (26% of theory) of the title compound were obtained as colorless crystals, melting point: 155° C., $R_f$=0.29 (ethyl acetate:acetone=95:5).

IR(KBr) 3395, 1774, 1740, 1710, 1516, 1349 cm$^{-1}$.

$^1$H NMR (200 MHz, CDCl$_3$): δ=2.83 (dd, J=9 Hz, 2.5 Hz, 2H, H-1); 3.63 (dd, J=4 Hz, 3 Hz, 1H, 1H, H-6); 3.83 (s, 3H, COOCH$_3$); 4.23 (dt, J=9 Hz, 3 Hz, 1H, H-5); 4.67 (d, J=4 Hz, 1H, CH—COOCH$_3$); 5.33 and 5.56 (AB, J=14 Hz, 2H, COOCH$_2$); 7.44 and 8.67 (AB, J=5.5 Hz, 4H, pyridinyl-H); 7.71 and 8.26 (AB, J=9.5 Hz, 4H, p—NO$_2$—C$_6$H$_4$).

MS: m/e (FAB) 486 (M+H), 524 (M+K); Calc.: 485.46.

EXAMPLE 14

Sodium (5R,6S)-6-[(1S)-1-hydroxy-1-methoxycarbonyl]methyl-7-oxo-3-(4-pyridinylthio)-1-azabicyclo[3.2.0]hept-2-encarboxylate

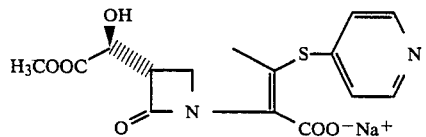

A solution of 245 mg (0.5 mmol) of p-nitrobenzyl (5R,6S)-6-[(1S)-1-hydroxy-1-methoxycarbonyl]methyl-7-oxo-3-(4-pyridinylthio)-1-azabicyclo[3.2.0]hept-2-en-2-caroxylate in 15 ml of a mixture comprising THF and 0.1M phosphate buffer pH 7 (1:1) was hydrogenated for 2 hours in the presence of 245 mg of palladium on charcoal (10%). The catalyst was then separated off by filtration through kieselguhr, the THF was removed in vacuo, and the pH of the remaining solution was adjusted to 7. The aqueous solution was extracted twice with ethyl acetate, concentrated to about 10 ml in vacuo, and transferred to a column with 120 ml of Diaion HP 20. It was eluted with water which contained an increasing proportion of acetonitrile. The fractions containing the product were collected, filtered through a 0.2 μmfilter, and freeze-dried. 93 mg (50% of theory) of the title compound were obtained as a colorless lyophilizate, $R_f$=0.19 (acetonitrile:water=9:1), in a purity of 97% (HPLC).

IR(KBr) 3340, 1752, 1611, 1580 cm$^{-1}$.

$^1$H NMR (200 MHz, D$_2$O): δ=2.95 (d, J=9.5 Hz, 2H, H-1); 3.78 (s, 3H, COOCH$_3$); 3.92 (dd, J=3 Hz, 2.5 Hz, 1H, H-6); 4.27 (dt, J=9.5 Hz, 1H, H-5); 4.80 (d, J=3 Hz, 1H, CH—COOCH$_3$); 7.51 and 8.43 (AB, J=5 Hz, 4H, pyridinyl-H).

EXAMPLE 15 AND EXAMPLE 16

(2R,3S)-1-(t-butoxycarbonylmethyl)-1-(4-methoxyphenyl)-4-[(1S)-1-phenethyl]-2,3-oxiranedicarboxamide

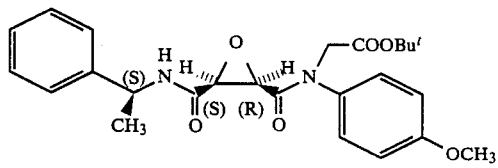

and (2S,3R)-1-(t-butoxycarbonylmethyl)-1-(4-methoxyphenyl)-4-[(1S)-1-phenethyl]-2,3-oxiranedicarboxamide

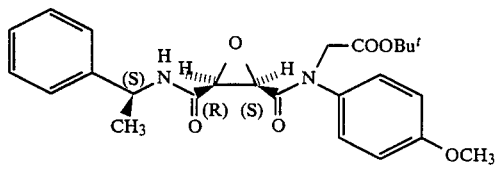

Method A:

A solution of 100.3 g (4.2 mol) of t-butyl N-(4-methoxyphenyl)glycinate [M. Shiozaki et al., Tetrahedron, 40, 1795 (1984)] in 100 ml of THF and a solution of 87.3 g (0.42 mol) of dicyclohexylcarbodiimide in 100 ml of THF were simultaneously added dropwise at room temperature within 30 minutes to a stirred solution of 55.8 g (0.42 mol) of 2,3-oxiranedicarboxylic acid [G. B. Payne et al., J. Org. Chem. 24, 54 (1959)] in 630 ml of THF. The mixture was stirred for 30 minutes at room temperature, a solution of 54.5 ml (0.42 mol) of (S)-(−)-1-phenethylamine in 100 ml of THF and a solution of 87.3 g (0.42 mol) of dicyclohexylcarbodiimide in 100 ml of THF were added successively, and the mixture was stirred for a further 1 hour at room temperature. The precipitate was separated off by filtration, and the filtrate solution was evaporated in vacuo and filtered through 2 kg of silica gel (toluene:ethyl acetate=8:2→7:3). 2 crude fractions were thus obtained which were purified by further chromatography on 1 kg of silica gel in each case and yielded the isomeric title compounds:

non-polar isomer: $R_f$=0.38 (toluene:ethyl acetate=7:3).

[α]$_D^{20}$=164.4° (c=0.897 in CHCl$_3$).

IR(KBr) 3384, 1746, 1682, 1606, 1444, 1370 cm$^{-1}$.

$^1$H NMR (250 MHz, CDCl$_3$): δ=1.48 (s, C(CH$_3$)$_3$); 1.48 (d, J=7.5 Hz, CHCH$_3$); together 13H, 3.41 and 3.46 (AB, J=5.5 Hz, 2H, oxirane-H); 3.83 (s, 3H, OCH$_3$); 4.23 and 4.35 (AB, J=16 Hz, 2H, CH$_2$COO); 5.12 (q, J=7.5 Hz, 1H, CHCH$_3$); 6.96 (d, J=9 Hz, 2H, p—H$_3$CO—C$_6$H$_4$); 7.3-7.4 (m, 7H, Ph, p—H$_3$-CO—C$_6$H$_4$).

C$_{25}$H$_{30}$N$_2$O$_6$ (454.5) Calc.: C 66.07, H 6.65, N 6.16, Found: C 66.3, H 6.9, N 6.2.

polar isomer: $R_f$=0.26 (toluene:ethyl acetate=7:3).

[α]$_D^{20}$=−189.4° (c=0.405 in CHCl$_3$)

$^1$H NMR (200 MHz, acetone-d$_6$): δ=1.44 (s, 9H, C(CH$_3$)$_3$); 1.49 (d, J=7 Hz, 3H, CHCH$_3$); 3.38 and 3.54 (AB, J=6 Hz, 2H, oxirane-H); 3.83 (s, 3H, OCH$_3$); 3.92 and 4.36 (AB, J=17 Hz, 2H, CH₂COO); 5.08 (m, 1H, CHCH₃); 6.95 and 7.23 (d, J=9 Hz, 4H, p—H₃-CO—C₆H₄); 7.38 (m, 5H, Ph).

EXAMPLE 17 WAS OBTAINED AS A BYPRODUCT OF THIS REDUCTION:

(±)-cis-N-(t-butoxycarbonylmethyl)-N-(4-methoxyphenyl)-N'-cyclohexyl-N'-cyclohexylaminocarbonyl-2,3-oxiranedicarboxamide

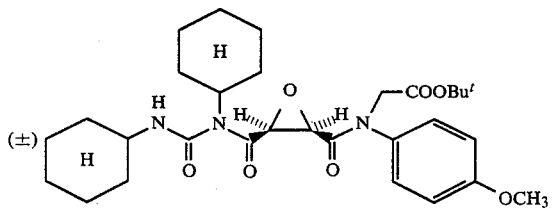

as colorless crystals, melting point: 150° C., R_f=0.40 (toluene:ethyl acetate=4:1).

IR(KBr) 3397, 1739, 1705, 1673, 1513 cm⁻¹.

¹H NMR (200 MHz, DMSO): δ=1.0–1.8 (m, —CH₂—); 1.42 (s, C(CH₃)₃) together 29H, 2.04 (m, 2H, N—CH—CH₂); 3.50 and 3.74 (m, 2H, oxirane-H); 3.76 (s, 3H, OCH₃); 4.16 (bs 2H, CH₂COO); 5.32 (bs, 1H, CONH); 7.00 and 7.36 (AB, J=9 Hz, 4H, p—H₃-CO—C₆H₄).

MS (CI, 150 eV, NH₃): m/e=558 (M+H); Calc. 557.70.

Method B:

1.24 ml (9.5 mmol) of (S)-(−)-phenethylamine, 2.0 g (9.5 mmol) of dicyclohexylcarbodiimide in 3 ml of THF, and 1.28 g (9.5 mmol) of 1-hydroxy-1H-benztriazole were added successively to a solution of 3.34 g (9.5 mmol) of (2R,3SR)-N-(t-butoxycarbonylmethyl)-N-(4-methoxyphenyl)-3-carboxy-2,3-epoxypropionamide in 15 ml of anhydrous THF. The initially clear solution was stirred for 2 hours at room temperature. The resultant precipitate was filtered off under suction, and the filtrate solution was evaporated in vacuo. The mixture thus obtained of the title compounds was separated by chromatography on 640 g of silica gel (toluene:ethyl acetate=4:1), and yielded 646 mg (15% of theory) of the pure non-polar diastereomer, R_f=0.38 (toluene:ethyl acetate=7:3), and 983 mg (21% of theory) of the pure polar diastereomer, R_f=0.26 (toluene:ethyl acetate=7:3).

The physical data were identical to the diastereomers prepared by method A.

EXAMPLE 18

(3S,4S)-4-t-butoxycarbonyl-3-[(1S)-1-hydroxy-1-[(1S)-1-phenethylaminocarbonyl]methyl-1-(4-methoxyphenyl)azetidin-2-one

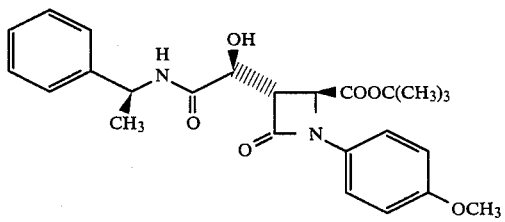

A solution of 880 mg (1.94 mmol) of (2R,3S)-1-(t-butoxycarbonylmethyl)-1-(4-methoxyphenyl)-4-[(1S)-1-phenethyl]-2,3-oxiranedicarboxamide was added dropwise to a mixture, cooled to 0° C., of 2.3 mmol of tetrabutylammonium fluoride and 1 g of molecular sieve 4 Å in 2 ml of THF. After 15 minutes, the mixture was filtered, toluene was added to the filtrate solution, and the THF was evaporated off in vacuo. The remaining toluene solution was washed several times with water and dried over MgSO₄. After evaporation of the solvent in vacuo and chromatography of the residue on 40 g of silica gel (toluene:ethyl acetate=7:3), 285 mg (32% of theory) of the title compound were obtained as colorless crystals, melting point: 184° C., R_f=0.19 (toluene:ethyl acetate=7:3), [α]_D²⁰=−47.3° (c=0.8085 in CHCl₃).

IR(KBr) 3348 (OH), 1769 (C=O, β-lactam), 1748 (C=O, ester), 1658 (C=O, amide), 1515 cm⁻¹.

¹H NMR (250 MHz, CDCl₃): δ=1.45 (s, 9H, C(CH₃)₃); 1.54 (d, J=7 Hz, 3H, CHCH₃); 3.60 (dd, J=7.5 Hz, 2 Hz, 1H, H-3); 3.79 (s, 3H, OCH₃); 4.01 (d, J=4.5 Hz, 1H, OH); 4.42 (dd, J=7.5 Hz, 4.5 Hz, 1H, HO—CH—CON); 4.48 (d, J=2 Hz, 1H, H-4); 5.14 (dq, J=8 Hz, 7 Hz, 1H, CHCH₃); 6.88 (d, J=9 Hz, 2H, C₆H₄); 7.2–7.4 (m, 7H, Ph, P—H₃CO—C₆H₄; 7.83 (d, J=8 Hz, 1H, CONH).

EXAMPLE 19

(3S,4S)-4-carboxy-3-[(1S)-1-hydroxy-1-{(1S)-1-phenethylaminocarbonyl}]methyl-1-(4-methoxyphenyl)acetidin-2-one

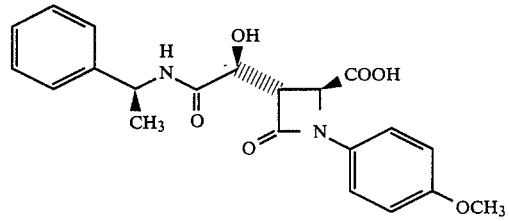

As described for Preparation Example 5, 103 mg (78% of theory) of the title compound were obtained from 150 mg (0.33 mmol) of (3S,4S)-4-t-butoxycarbonyl-3-[(1S)-1-hydroxy-1-{(1S)-1-phenethylaminocarbonyl}]methyl-1-(4-methoxyphenyl)azetidin-2-one, as colorless crystals, melting point: 186° C., R_f=0.68 (BABA).

IR(KBr) 3320, 1750, 1658, 1630, 1515, 1248 cm⁻¹.

¹H NMR (200 MHz, DMSO): δ=1.44 (d, J=7 Hz, 3H, CHCH₃); 3.66 (dd, J=2 Hz, 1.5 Hz, 1H, H-3); 3.74 (s, 3H, OCH₃); 4.34 (m, 1H, HO—CH—CON); 4.60 (d, J=2 Hz, 1H, H-4); 5.00 (dq, J=9 Hz, 7 Hz, 1H, CHCH₃); 6.36 (d, J=6 Hz, 1H, OH); 6.97 and 7.25 (AB, J=9 Hz, 4H, p—H₃CO—C₆H₄); 7.38 (m, 5H, Ph); 8.36 (d, J=9 Hz, 1H, CONH); 12.80 (bs, 1H, COOH).

EXAMPLE 20

(3R,4R)-4-acetoxy-3-[(1S)-1-hydroxy-1-{(1S)-1-phenethylaminocarbonyl}]methyl-1-(4-methoxyphenyl)azetidin-2-one

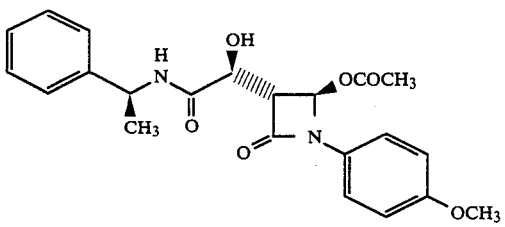

As described for Example 6, 42 mg (39% of theory) of the title compound were obtained from 105 mg (0.26 mmol) of (3S,4S)-4-carboxy-3-[(1S)-1-hydrox-1-{(1S)-1-phenethylaminocarbonyl]}]methyl-1-(4-methoxyphenyl)-azetidin-2-one after 5 minutes at 60° C. and chromatography of the crude product on 6 g of silica gel (toluene:ethyl acetate=3:2), as colorless crystals, melting point: 202° C., (toluene), $R_f$=0.30 (toluene:ethyl acetate=1:1).

IR(KBr) 3290, 1746, 1650, 1627, 1515, 1250 cm$^{-1}$.

$^1$H NMR (200 MHz, acetone-d$_6$): δ=1.51 (d, J=6.5 Hz, 3H, CHC$\underline{H}_3$); 3.73 (dd, J=2 Hz, 1 Hz, 1H, H-3); 3.78 (s, 3H, OC$\underline{H}_3$); 4.48 (d, J=2 Hz, 1H, HO—C$\underline{H}$—(—CON); 5.10 (dq, J=9 Hz, 6.5 Hz, 1H, C$\underline{H}$CH$_3$); 6.63 (d, J=1 Hz, 1H, H-4); 6.95 (d, J=10 Hz, 2H, p—C$_6$H$_4$); 7.2–7.4 (m, 7H, Ph, p—H$_3$CO—C$_6$H$_4$); 7.79 (d, J=9 Hz, 1H, CONH).

EXAMPLE 21

(3R,4R)-4-acetoxy-3-[(1S)-1-butyldimethylsilyloxy-1-{(1S)-1-phenethylaminocarbonyl)}]methyl-1-(4-methoxyphenyl)azetidin-2-one

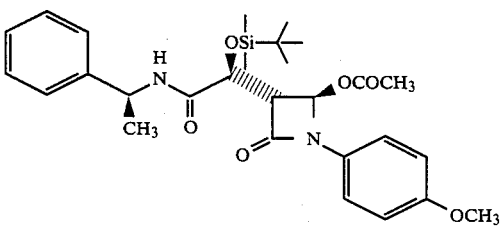

As described for Example 7, 409 mg (76% of theory) of the title compound were obtained from 424 mg (1.028 mmol) of (3R,4R)-4-acetoxy-3-[(1S)-1-hydroxy-1-{(1S)-1-phenethylaminocarbonyl)}]methyl-1-(4-methoxyphenyl)azetidin-2-one after 9 days at room temperature and chromatography of the crude product on 25 g silica gel (toluene:ethyl acetate=4:1), as colorless crystals, melting point: 115° C., $R_f$=0.60 (toluene:ethyl acetate=3:2).

IR(CHCl$_3$) 3390, 1750, 1663, 1510, 840 cm$^{-1}$.

$^1$NMR (200 MHz, acetone-d$_6$): δ=0.03 (s, 6H, CH$_3$—Si), 0.78 (s, 9H, CH$_3$—C—Si); 1.50 (d, J=8 Hz, 3H, CHC$\underline{H}_3$); 3.70 (dd, J=2 Hz, 0.5 Hz, 1H, H-3); 3.79 (s, 3H, OC$\underline{H}_3$); 4.53 (d, J=2 Hz, 1H, C$\underline{H}$—OSi); 5.05 (dq, J=9 Hz, 8 Hz, 1H, C$\underline{H}$CH$_3$); 6.67 (d, J=0.5 Hz, 1H, H-4); 6.95 and 7.40 (AB, J=10 Hz, 4H, p—H$_3$CO—C$_6$H$_4$); 7.40 (m, 5H, Ph).

EXAMPLE 22

(3S*,4S*)-4-t-butoxycarbonyl-3-[(1S*)-1-{(N-cyclohexylaminocarbonyl}cyclohexylaminocarbonyl-1-hydroxymethyl]-1-(4-methoxyphenyl)azetidin-2-one

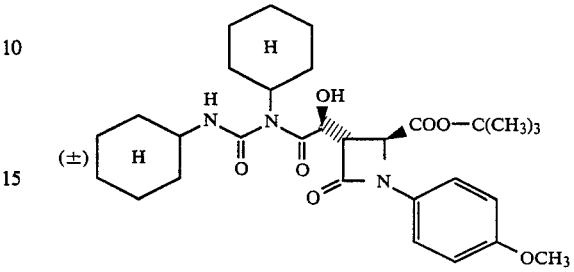

As described for Example 18, the title compound $R_f$=0.15 (toluene:ethyl acetate=9:1), was obtained from 2.23 g (4.00 mmol) of cis-N-(t-butoxycarbonylmethyl)-N-(4-methoxyphenyl)-N'-cyclohexyl-N'-cyclohexylaminocarbonyl-2,3-oxiranedicarboxamide after 2 hours at 0° C. in the presence of 1.7 equivalents of tetrabutylammonium fluoride and chromatography of the crude product on 150 g of silica gel (toluene:ethyl acetate=4:1).

IR(CHCl$_3$) 1748, 1643, 1462, 1255 cm$^{-1}$.

$^1$H NMR (200 MHz, CDCl$_3$): δ=1.0–2.5 (m, 22H, cyclohexyl-H); 3.66 (m, 1H, H-3); 3.83 (s, 3H, OCH$_3$); 4.25 (m, 1H; H-4); 4.48 (d, J=5 Hz, 1H, HO—C$\underline{H}$—CON); 7.40 and 7.80 (AB, J=10 Hz, 4H, p—H$_3$CO—C$_6$H$_4$); 7.60 (d, J=9.5 Hz, 1H, CONH).

EXAMPLE 23

(3S*,4S*)-4-carboxy-3-[(1S*)-1-{N-cyclohexylaminocarbonyl}cyclohexylaminocarbonyl-1-hydroxymethyl]-1-(4-methoxyphenyl)azetidin-2-one

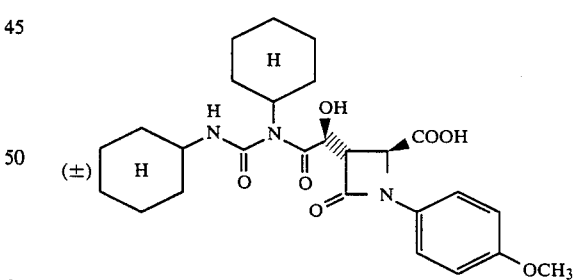

As described for Example 5, 22 mg (79% of theory) of the title compound were obtained from 31 mg (0.06 mmol) of (3S*,4S*)-4-t-butoxycarbonyl-3-[(1S*)-1-{N-cyclohexylaminocarbonyl}cyclohexylaminocarbonyl-1-hydroxymethyl]-1-(4-methoxyphenyl)azetidin-2-one, as crystals, melting point: 169° C., $R_f$=0.08 (BABA).

IR(KBr) 3400, 1759, 1693, 1513, 1440, 1252 cm$^{-1}$.

$^1$H NMR (200 MHz, DMSO); δ=1.0–2.2 (m, 22H, cyclohexyl-H); 3.80 (m, H-3); 3.82 (s, OCH$_3$) together 4H, 4.85 (m, H-4, HO—C$\underline{H}$—CON); 6.96 and 7.60 (AB, J=9.5 Hz, 4H, p—H$_3$CO—C$_6$H$_4$).

EXAMPLE 24

(3R,4R)-4-t-butoxycarbonyl-3-[(1R)-1-hydroxy-1-{(1S)-1-phenethylaminocarbonyl)}]methyl-1-(4-methoxyphenyl)azetidin-2-one

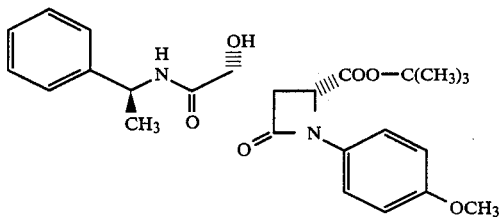

As described for Example 18, 120 mg (36% of theory) of the title compound were obtained from 332 mg (0.73 mmol) of (2S,3R)-[1-(t-butoxycarbonyl)-1-(4-methoxyphenyl)]methyl-4-[(1S)-1-phenethyl]-2,3-oxiranedicarboxamide and after chromatography of the crude product on 28 g of silica gel (toluene:ethyl acetate=3:2), as colorless crystals, melting point: 131° C., R$_f$=0.29 (toluene:ethyl acetate=1:1).

IR (CHCl$_3$) 3340, 1750, 1665, 1510 cm$^{-1}$.

$^1$H NMR (200 MHz, CDCl$_3$): δ=1.45 (s, 9H, C(CH$_3$)$_3$), 1.59 (d, J=7 Hz, 3H, CHCH$_3$); 3,73 (dd, J=7.5 Hz, 0.5 Hz, 1H, H-3); 3.80 (s, 3H, OCH$_3$); 4.49 (m, 2H, HO—CH—CON, H-4); 5.16 (dq, J=8.5 Hz, 7 Hz, 1H, CHCH$_3$); 6.86 and 7.28 (AB, J=9.5 Hz, p—H$_3$-CO— C$_6$H$_4$); 7.38 (m, Ph) together 9H, 7.80 (d, J=8.5 Hz, 1H, CONH).

EXAMPLE 25

(3R,4R)-4-carboxy-3-[(1R)-1-hydroxy-1-{(1S)-1-phenethylaminocarbonyl)}]methyl-1-(4-methoxyphenyl)azetidin-2-one

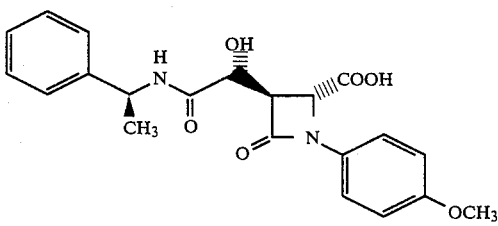

As described for Example 5, 84 mg (91% of theory) of the title compound were obtained from 105 mg (0.23 mmol) of (3R,4R)-4-t-butoxycarbonyl-3-[(1R)-1-hydroxy-1{(1S)-1-phenethylaminocarbonyl)}]methyl-1-(4-methoxyphenyl)azetidin-2-one, as a colorless solid, melting point: 161° C., R$_f$=0.61 (BABA).

IR (KBr) 1746, 1654, 1512, 1249 cm$^{-1}$.

$^1$H NMR (200 MHz, acetone-d$_6$): δ=1.56 (d, J=7 Hz, 3H, CHCH$_3$); 3.81 (s, 3H, OCH$_3$); 3.90 (dd, J=2 Hz, 2 Hz, 1H, H-3); 4.66 (m, 2H, HO—CH—CON, H-4); 5.18 (dq, J=8 Hz, 7 Hz, 1H, CHCH$_3$); 6.98 (d, J=9.5 Hz, 2H, p—C$_6$H$_4$); 7.3–7.5 (m, 7H, Ph, p—H$_3$-CO—C$_6$H$_4$); 8.00 (d, J=8 Hz, 1H, CONH).

EXAMPLE 26

(3S,4S)-4-acetoxy-3-[(1R)-1-hydroxy-1-(1S)-1-phenethylaminocarbonyl)]methyl-1-(methoxyphenyl)azetidin-2-one

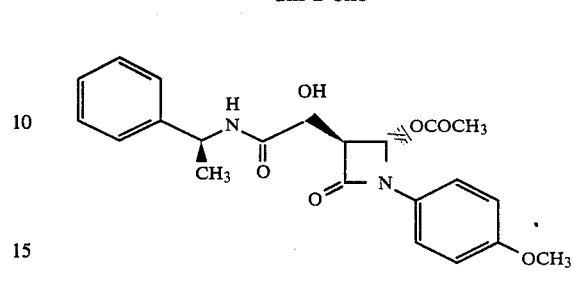

As described for Example 6, 316 mg (32% of theory) of the title compound were obtained from 966 mg (2.43 mmol) of (3R,4R)-4-t-butoxycarbonyl-3-[(1R)-1-hydroxy-1-{(1S)-1-phenethylaminocarbonyl)}]methyl-1-(4-methoxyphenyl)azetidin-2-one after 5 minutes at 60° C. and chromatography of the crude product on 60 g of silica gel (toluene:ethyl acetate=1:1), as a colorless solid, melting point: 197° C. (acetone), R$_f$=0.18 (toluene:ethyl acetate=3:2).

IR(KBr) 3300 (OH), 1753 (C=O, β-lactam, ester), 1652 (C=O, amide), 1515 cm$^{-1}$.

$^1$H NMR (200 MHz, acetone-d$_6$): δ=1.49 (d, J=7.5 Hz, 3H, CHCH$_3$); 2.03 (s, with acetone, OCOCH$_3$); 3.76 (s, OCH$_3$); 3.76 (m, OH, H-3) together 5H); 4.50 (d, J=2 Hz, 1H, HO—CH—CON); 5.05 (dq, J=9 Hz, 7.5 Hz, 1H, CH—CH$_3$); 6.61 (d, J=1 Hz, 1H, H-4); 6.91 (d, J=9.5 Hz, 2H, p—C$_6$H$_4$); 7.2–7.4 (m, 7H, Ph, p—H$_3$-CO—C$_6$H$_4$); 7.79 (d, J=9 Hz, 1H, CONH).

EXAMPLE 27

(3S,4S)-4-acetoxy-3-[(1R)-1-t-butyldimethylsilyloxy-1-{(1S)-1-phenethylaminocarbonyl)}]methyl-1-(4-methoxyphenyl)azetidin-2-one

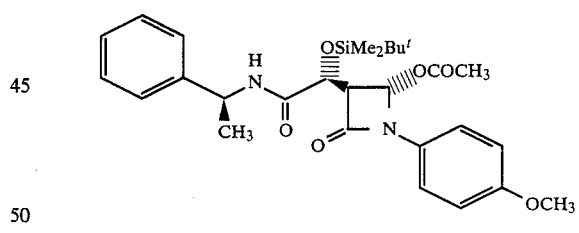

As described for Example 7, 282 mg (83% of theory) of the title compound were obtained from 267 mg (0.65 mmol) of (3S,4S)-4-acetoxy-3-[(1R)-1-hydroxy-1-{(1S)-1-phenethylaminocarbonyl)}]methyl-1-(4-methoxyphenyl)azetidin-2-one after 7 days at room temperature and chromatography of the crude product on 15 g of silica gel (toluene:ethyl acetate=4:1), as colorless crystals, melting point: 120° C., R$_f$=0.27 (toluene:ethyl acetate=4:1).

IR(KBr) 3426, 1767 (C=O, β-lactam), 1748 (C=O, ester), 1681 (C=O, amide), 1511, 1399, 1264 cm$^{-1}$.

$^1$H NMR (250 MHz, CDCl$_3$): δ=0.03 (s, 3H, CH$_3$Si); 0.15 (s, 3H, CH$_3$Si); 0.83 (s, 9H, CH$_3$—C—Si); 1.53 (d, J=8 Hz, 3H, CH$_3$CH); 1.98 (s, 3H, OCOCH$_3$); 3.78 (s, 3H, OCH$_3$); 3.81 (dd, J=2 Hz, 0.5 Hz, 1H, H-3); 4.59 (d, J=2 Hz, 1H, CH—OSi); 5.08 (dq, J=8 Hz, 8 Hz, 1H, CH$_3$CH); 6.51 (d, J=0.5 Hz, 1H, H-4); 6.84 (d, J=10

Hz, 2H, p—C6H4); 6.93 (d, J=8 Hz, 1H, CONH); 7.3–7.4 (m, 7H, Ph, p—H3CO—C6H4).

EXAMPLE 28

(3S,4S)-4-acetoxy-3-[(1R)-1-t-butyldimethylsilyloxy 1-{(1S)-1-phenethylaminocarbonyl)}]methyl-azetidin-2-one

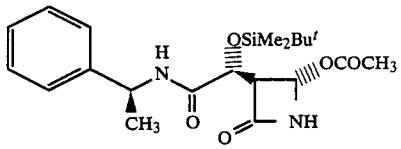

As described for Example 8, 76 mg (69% of theory) of the title compound were obtained from 138 1 mg (0.26 mmol) of (3S,4S)-4-acetoxy-3-[(1R)-1-butyldimethyl-silyloxy-1-{(1S)-1-phenethylaminocarbonyl)}]methyl-1-(4-methoxyphenyl)azetidin-2-one after chromatography of the crude product on 18 g of silica gel (toluene-:ethyl acetate=7:3), as colorless crystals, melting point: 126° C., (n-heptane), R$_f$=0.35 (toluene:ethyl acetate=3:2); [α]$_D^{20}$=−9.3° (c: 0.925, CHCl3).

IR(KBr) 3420, 1786 (C=O, β-lactam), 1750 (C=O, ester), 1680 (C=O, amide), 1526, 1228 cm$^{-1}$.

$^1$H NMR (250 MHz, CDCl3): δ=0.14 and 0.16 (s, 6H, CH3—Si); 0.95 (s, 9H, CH3—C—Si); 1.51 (d, J=8 Hz, 3H, CH3CH); 1.96 (s, 3H, OCOCH3); 3.75 (dd, J=2 Hz, 1 Hz, 1H, H-3); 4.51 (d, J=2 Hz, 1H, CH—OSi); 5.12 (dq, J=9.5 Hz, 8 Hz, 1H, CH3CH); 5.63 (d, J=1 Hz, 1H, H-4); 5.43 (bs, 1H, azetidinone NH); 6.91 (d, J=9.5 Hz, 1H, CONH, 7.2–7.3 (m, 5H, Ph).

EXAMPLE 29

(2RS,3SR)-N-(t-butoxycarbonylmethyl)-N-(4-methoxphenyl)-3-carboxy-2,3-epoxypropionamide

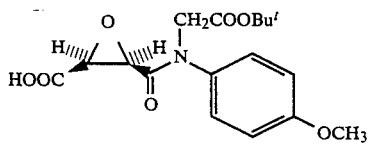

A solution of 230 mg (10.0 mg-atoms) of sodium in 10 ml of anhydrous methanol were added at room temperature to a solution of (2RS,3SR)-N-(t-butoxycarbonyl-methyl)-N-(4-methoxyphenyl)-3-methoxycarbonyl-2,3-epoxypropionamide. Exactly 180 μl (10 mmol-1 equiv.) of water were added to this solution, and the mixture was stirred for a further 15 hours at room temperature. The reaction mixture was subsequently evaporated in vacuo, dissolved in 15 ml of water, washed with ether, covered with 10 ml of ethyl acetate and adjusted to pH 2.5 using 2.5N H2SO4 with cooling. The mixture was extracted 4 times with ethyl acetate, the organic phase was dried over MgSO4, and the solvent was evaporated in vacuo. 3.44 g (98% of theory) of the title compound were obtained as a colorless solid, R$_f$=0.36 (BABA).

$^1$H NMR (200 MHz, DMSO): δ=1.39 (s, 9H, C(CH3)3), 3.52 and 3.59 (AB, J=5 Hz, 2H, H-2, H-3); 3.78 (s, 3H, OCH3); 4.22 (bs, 2H, NCH2COO); 7.02 and 7.35 (AB, J=9.5 Hz, 4H, p—H3CO—C6H4); 12.87 (bs, 1H, COOH).

EXAMPLE 30

(3R,4R)-4-acetoxy-3-[(1S)-1-tert-butyldimethylsilyloxy1-{(1S)-1-phenethylaminocarbonyl)}]methyl-azetidin-2-one

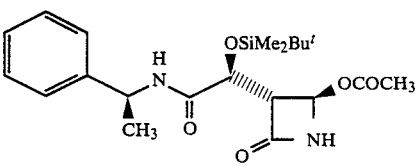

As described for Example 8, 342 mg (73% of theory) of the title compound were obtained from 590 mg (1.12 mmol) of (3R,4R)-4-acetoxy-3-[(1S)-tert-butyldimethyl-silyloxy-1-{(1S)-1-phenethylaminocarbonyl)}]methyl-1-(4-methoxyphenyl)azetidin-2-one and chromatography of the crude product on 60 g of silica gel (toluene-:ethyl acetate=3:2), as a hard colorless foam, R$_f$=0.24 (toluene:ethyl acetate=3:2).

IR (CHCl3): 3390, 1782 (C=O, β-lactam, 1739 (C=O, ester), 1662 (C=O, amide), 1500 cm$^{-1}$.

$^1$H NMR (250 MHz, acetone-d6): δ=0.01 and 0.07 (s, 6H, CH3Si); 0.85 (s, 9H, CH3—C—Si); 1.45 (d, J=7.5 Hz, 3H, CH3CH); 2.04 (s, 3H, OCOCH3); 3.52 (dd, J=2 Hz, 1 Hz, 1H, H-3); 4.41 (d, J'Hz, 1H, CH—O—Si); 5.07 (dq, J=8 Hz, 7.5 Hz, 1H, CH3CH); 6.03 (d, J=1 Hz, 1H, H-4); 7.2–7.4 (m, 5H, Ph); 8.12 (bs, 1H, NH).

EXAMPLE 31

(3S,4R)-3-[(1S)-1-tert-butyldimethylsilyloxy-1-{(1S)-1-phenethylaminocarbonyl)}]methyl-4-[3-p-nitrobenzyloxycarbonyl-3-diazo-2-oxopropyl]azetidin-2-one

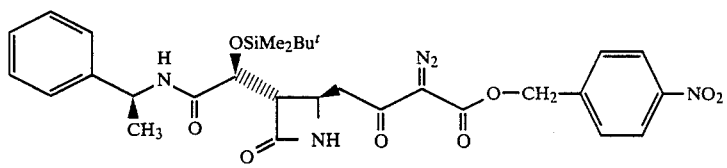

As described for Example 10, 121 mg (38% of theory) of the title compound were obtained from 210 mg (0.5 mmol) of (3R,4R)-4-acetoxy-3-[(1S)-tert-butyldimethyl-silyloxy-1-{(1S)-1-phenethylaminocarbonyl)}]methyl-azetidin-2-one after 40 minutes at room temperature and chromatography of the crude product on 15 g of silica gel (toluene:ethyl acetate=1:1), as a pale solid, R$_f$=0.16 (Toluene:ethyl acetate=3:2).

IR(KBr) 2140 (N2), 1758 (C=O, β-lactam), 1717 (C=O, ester), 1655 (C=O, amide).

$^1$H NMR (200 MHz, acetone-d6): δ=0.16 and 0.21 (s, 6H, CH3Si); 0.97 (s, 9H, CH3—C—Si); 1.52 (d, J=7.5 Hz, 3H, CH3CH); 2.61 (dd, J=18 Hz, 3.5 Hz), 1H H-1); 2.91 (dd, J=18 Hz, 10 Hz, 1H, H-1); 3.20 (dd, J=2.5 Hz, 2 Hz, 1H, H-3); 4.03 (ddd, J= Hz, 3.5 Hz, 2 Hz, 1H, H-4); 4.47 (d, J=2.5 Hz, 1H, CH—O—Si); 5.06 (dq, J=7.5 Hz, 7.5 Hz, 1H, CH3CH); 5.47 (s, COOCH2); 5.5

(bs, NH) together 3H, 7.2–7.5 (m, 6H, Ph, NH); 7.75 and 8.35 (AB, J=10 Hz, 4H, p—NO$_2$—C$_6$H$_4$).

EXAMPLE 32

(3S,4R)-3-[(1S)-1-hydroxy-1{(1S)-1-phenethylaminocarbonyl}]methyl-4-[3-p-nitrobenzyloxycarbonyl-3-diazo-2-oxopropyl]azetidin-2-one

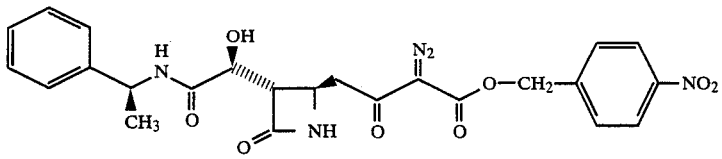

As described for Example 11, 86 mg (92% of theory) of the title compound were obtained from 115 mg (0.18 mmol) of (3S,4R)-3-[(1S)-1-tert-butyldimethylsilyloxy 1-{(1S)-1-phenethylaminocarbonyl)}]methyl-4-[3-p-nitrobenzyloxycarbonyl-3-diazo-2-oxopropyl]azetidin-2-one, as a pale solid, R$_f$=0.28 (toluene:ethyl acetate=1:9).

IR (KBr) 3350 (OH), 2138 (N$_2$), 1758 (C═O, β-lactam), 1725 (C═O, ester); 1657 (C═O, amide); 1520 (NO$_2$, asym.), 1350 cm$^{-1}$ (NO$_2$, sym.).

$^1$H NMR (200 MHz, acetone-d$_6$); δ=1.49 (d, J=8 Hz, 3H, C$\underline{H_3}$CH); 2.59 (dd, J=17.5 Hz, 3 Hz, 1H, H-1); 2.87 (dd, J=17.5 Hz, 9.5 Hz, 1H, H-1); 3.18 (dd, J=2 Hz, 2 Hz, 1H, H-3); 4.0 (m, 1H, H-4); 4.44 (d, J=2 Hz, 1H, CO—CH—O); 5.10 (dq, J=8 Hz, 7.5 Hz, 1H, CH$_3$C$\underline{H}$); 5.45 (s, 2H, COOC$\underline{H_2}$); 5.7 (bs, 1H, NH); 7.25–7.45 (m, 5H, Ph), 7.78 and 8.29 (AB, J=9.5 Hz, 4H, p—NO$_2$—C$_6$H$_4$).

It is understood that the specification and examples are illustrative but not limitative of the present invention and that other embodiments within the spirit and scope of the invention will suggest themselves to those skilled in the art.

We claim:

1. A substituted 6-hydroxymethyl-carbapenem antibiotic of the formula

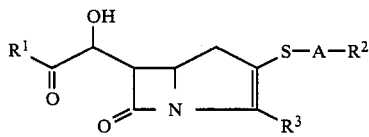

in which
R$^1$ represents a group of the formula —OR$^4$,

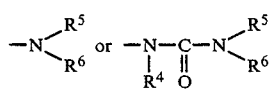

in which
R$^4$, R$^5$ and R$^6$ are identical or different and denote hydrogen or C$_6$–C$_{12}$-aryl which is optionally up to trisubstituted, identically or differently, by nitro, hydroxyl, cyano, halogen, trifluoromethyl, trifluoromethoxy, C$_1$–C$_6$-alkyl or C$_1$–C$_6$-alkoxy, or denote C$_1$–C$_{12}$-alkyl, C$_2$–C$_{12}$-alkenyl or C$_3$–C$_8$-cycloalkyl, these radicals being optionally polysubstituted, identically or differently by C$_1$–C$_4$alkoxy, halogen, hydroxyl, cyano and/or phenyl, where this phenyl radical may again carry up to three identical or different substituents from the series comprising C$_1$–C$_4$-alkyl, C$_1$–C$_4$-alkoxy, nitro, cyano, hydroxyl or halogen, and/or by a group of the formula —CO$_2$R$^7$ and/or —NR$^8$R$^9$, in which
R$^7$ represents hydrogen, phenyl, benzyl, C$_1$–C$_8$-alkyl or C$_2$–C$_6$-alkenyl, and
R$^8$ and R$^9$ are identical or different and represent hydrogen, C$_1$–C$_6$-alkyl, phenyl, benzyl or an amino-protecting group, A represents a direct bond or
represents a C$_1$–C$_{12}$-alkylene or C$_2$–C$_{12}$-alkenylene chain which is optionally interrupted in the chain by an oxygen atom or a sulphur atom, or
represents cycloalkylene having 3 to 8 carbon atoms, cycloalkylene-alkylene or alkylenecycloalkylene having 3 to 8 atoms in the cycloalkylene part and 1 to 8 carbon atoms in the alkylene chain, or
represents alkylene-cycloalkylene-alkylene having 3 to 8 atoms in the cycloalkyl part and 1 to 8 carbon atoms in each alkylene part, R$^2$
(a) represents a group of the formula

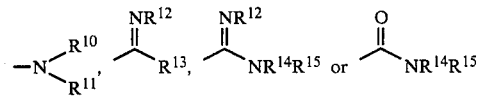

in which
R$^{10}$ denotes hydrogen, C$_1$–C$_{10}$-alkyl, C$_6$–C$_{12}$-aryl or C$_7$–C$_{14}$-aralkyl,
R$^{11}$ represents hydrogen, C$_1$–C$_{10}$-alkyl, C$_6$–C$_{12}$-aryl, C$_7$–C$_{14}$-aralkyl, C$_1$–C$_{10}$-alkylsulphonyl, C$_6$–C$_{12}$-arylsulphonyl, C$_7$–C$_{14}$-aralkylsulphonyl, an amino-protecting group, or a group of the formula

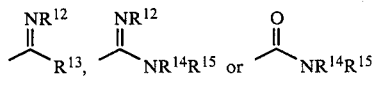

and
R$^{12}$, R$^{13}$, R$^{14}$ and R$^{15}$ are identical or different and denote hydrogen, C$_1$–C$_{10}$-alkyl, C$_6$–C$_{12}$ aryl or C$_7$–C$_{14}$-aralkyl, or
(b) represents a C$_6$–C$_{12}$-aryl radical which is optionally up to trisubstituted, identically or differently, or
(c) represents a radical of the formula

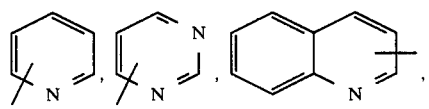

-continued

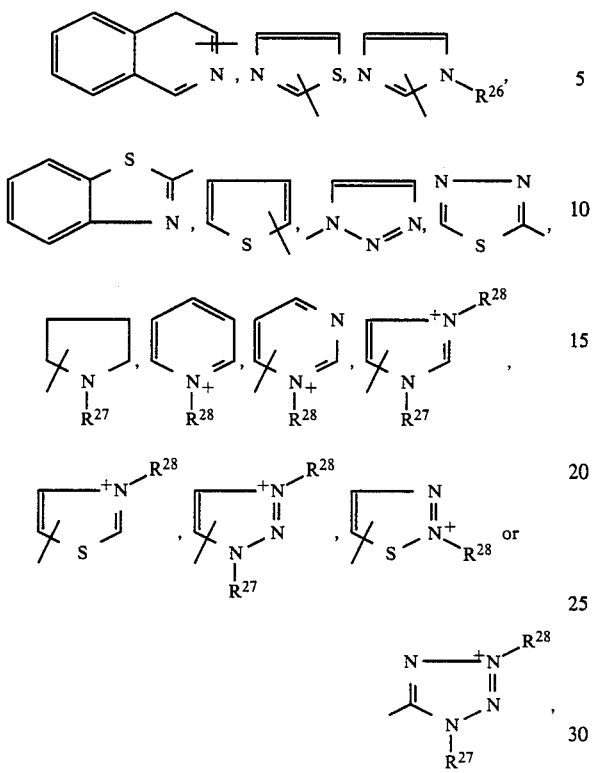

in which
R²⁶ denotes hydrogen, C₁-C₄-alkyl or phenyl,
R²⁷ denotes C₁-C₄-alkyl, C₁-C₄-alkylcarbonyl or a group of the formula

in which
R¹² and R¹³ are identical or different and have the abovementioned meaning, and
R²⁸ denotes C₁-C₄-alkyl or phenyl,
which is optionally substituted by methoxy, amino, methylamino, dimethylamino, acetylamino, formylamino, formylimidoamino, acetylimidoamino, guanidino, fluorine, chlorine, carbamoyl, sulphamoyl, C₁-C₄-alkyl, amino-C₁-C₂-alkyl, methylamino-C₁-C₂-alkyl, dimethylamino-C₁-C₂-alkyl, hydroxy-C₁-C₂-alkyl or carbamoyl-C₁-C₂-alkyl, or (d) represents a group of the formula

in which
R¹⁶, R¹⁷ and R¹⁸ are identical or different and represent a C₁-C₆-alkyl radical which is optionally substituted by hydroxyl, amino, carboxyl, cyano, nitro, methoxy, methoxycarbonyl, fluorine, chlorine, cyclopropyl, cyclopentyl, cyclohexyl, phenyl or pyridyl, or in which
R¹⁶ has the abovementioned meaning, and R¹⁷ and R¹⁸, together, represent the radical of the formula

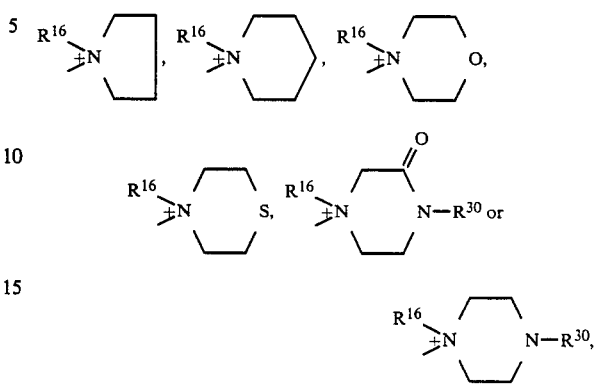

in which
R³⁰ represents C₁-C₄-alkyl, carbamoyl, formyl, acetylimido, formylimido, sulphamoyl, C₁-C₄-hydroxyalkyl, C₁-C₄-aminoalkyl or C₁-C₄-alkylsulphonyl,
which is optionally substituted by C₁-C₄-alkyl, C₁-C₄-hydroxyalkyl, C₁-C₄-aminoalkyl, carboxyl, methoxycarbonyl, formyl, acetyl, carbamoyl, amino, methylamino, dimethylamino, acetylamino, C₁-C₄-alkoxy, C₁-C₄-alkylsulphonyl or dimethylaminosulphonyl, or in which the

group represents a radical of the formula

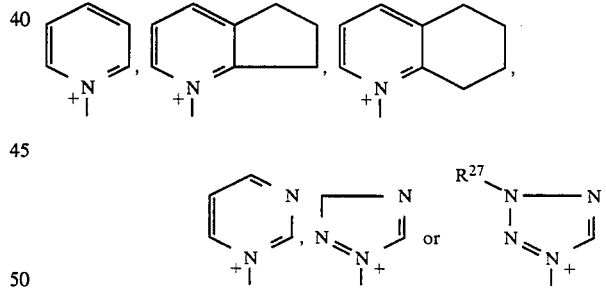

in which
R²⁷ has the indicated meaning, which is optionally substituted by C₁-C₄-alkyl, hydroxymethyl, carboxymethyl, methoxycarbonylmethyl, formylmethyl, carbamoylmethyl, methoxymethyl, methylsulphonylmethyl, cyanomethyl, trifluoromethyl, cyclopropyl, C₁-C₄-alkoxy, amino, methylamino, dimethylamino, acetylamino, formylamino, formylimidoamino, acetylimidoamino, guanidino, carbamoyl, N-methylcarbamoyl, dimethylcarbamoyl, dimethylaminosulphonyl, cyano, hydroxyl, fluorine or chlorine, or (e) represents C₁-C₈-alkoxycarbonylmethyl, carboxymethyl, hydroxymethyl or a group of the formula $$-\underset{\underset{R^{10}}{|}}{\overset{|}{C}H}-B-R^{19}$$
$$\phantom{-CH-B-}\underset{R^{11}}{}$$

in which
R$^{10}$ and R$^{11}$ have the abovementioned meaning,
B denotes a methylene or carbonyl group, and
R$^{19}$ denotes hydroxyl, amino, C$_1$–C$_6$-alkylamino, di-C$_1$–C$_6$-alkylamino, C$_6$–C$_{12}$-arylamino, C$_7$–C$_{14}$-aralkylamino, C$_2$–C$_7$-acylamino or pyridylamino and
R$^3$ represents a carboxyl group of the formula COOR$^{20}$,
in which
R$^{20}$ denotes hydrogen, a carboxyl-protecting group, or an ester radical which can be cleaved off in vivo, or
represents COO$^-$ if R$^2$ represents a radical having positive charge,
or a salt thereof.

2. A compound or salt according to claim 1, in which R$^2$ (a) represents a group of the formula $$-N\underset{R^{11}}{\overset{R^{10}}{\diagdown}}, \quad \overset{NR^{12}}{\underset{}{\|}}_{R^{13}}, \quad \overset{NR^{12}}{\underset{}{\|}}_{NR^{14}R^{15}} \text{ or } \overset{O}{\underset{}{\|}}_{NR^{14}R^{15}}$$

in which
R$^{10}$ denotes hydrogen, C$_1$–C$_8$-alkyl, phenyl or benzyl,
R$^{11}$ denotes hydrogen, C$_1$–C$_8$-alkyl, phenyl, benzyl, C$_1$–C$_8$-alkylsulphonyl, phenylsulphonyl, benzylsulphonyl, an amino-protecting group, or a group of the formula $$\overset{NR^{12}}{\underset{}{\|}}_{R^{13}}, \quad \overset{NR^{12}}{\underset{}{\|}}_{NR^{14}R^{15}} \text{ or } \overset{O}{\underset{}{\|}}_{NR^{14}R^{15}}$$

and
R$^{12}$, R$^{13}$, R$^{14}$ and R$^{15}$ are identical or different and denote hydrogen, C$_1$–C$_8$-alkyl, phenyl or benzyl, or (b) represents phenyl which is optionally up to disubstituted by fluorine, chlorine, bromine, hydroxyl, mercapto, C$_1$–C$_4$-alkyl, C$_1$–C$_4$-alkoxy, C$_1$–C$_4$-alkylthio, cyano, nitro, trifluoromethyl, trifluoromethoxy, carboxyl, C$_1$–C$_4$-alkoxycarbonyl, sulpho, C$_1$–C$_4$-alkylsulphonyl, phenylsulphonyl, tolylsulphonyl, carbamoyl, sulphamoyl, C$_1$–C$_4$-aminoalkyl, C$_1$–C$_4$-hydroxyalkyl, C$_1$–C$_4$-cyanoalkyl, C$_1$–C$_4$-carboxyalkyl, C$_1$–C$_4$-alkoxycarbonyl, C$_1$–C$_4$-alkyl or a group of the formula $$-N\underset{R^{11}}{\overset{R^{10}}{\diagdown}}, \quad \overset{NR^{12}}{\underset{}{\|}}_{R^{13}}, \quad \overset{NR^{12}}{\underset{}{\|}}_{NR^{14}R^{15}} \text{ or } \overset{O}{\underset{}{\|}}_{NR^{14}R^{15}}$$

in which
R$^{10}$, R$^{11}$, R$^{12}$, R$^{13}$, R$^{14}$ and R$^{15}$ have the abovementioned meaning, or (c) represents a radical of the formula

[heterocyclic ring structures including pyridine, pyrimidine, quinoline, isoquinoline, indane, pyrrole, thiazole, imidazole with R$^{26}$, thiazoline, pyrazole, tetrazole, thiadiazole, N-substituted pyrrolidine (R$^{27}$), pyridinium (R$^{28}$), imidazolium (R$^{28}$), thiazolium (R$^{28}$), pyrazolium, triazolium, thiadiazolium structures]

in which
R$^{26}$ denotes hydrogen, C$_1$–C$_4$-alkyl or phenyl,
R$^{27}$ denotes C$_1$–C$_4$-alkyl, C$_1$–C$_4$-alkylcarbonyl or a group of the formula $$\overset{NR^{12}}{\underset{}{\|}}_{R^{13}}$$

in which
R$^{12}$ and R$^{13}$ are identical or different and have the abovementioned meaning, and
R$^{28}$ denotes C$_1$–C$_4$-alkyl or phenyl,
is optionally substituted by methoxy, amino, methylamino, dimethylamino, acetylamino, formylamino, formylimidoamino, acetylimidoamino, guanidino, fluorine, chlorine, carbamoyl, sulphamoyl, C$_1$–C$_4$-alkyl, amino-C$_1$–C$_2$-alkyl, methylamino-C$_1$–C$_2$-alkyl, dimethylamino-C$_1$–C$_2$-alkyl, hydroxy-C$_1$–C$_2$-alkyl or carbamoyl-C$_1$–C$_2$-alkyl, or (d) represents a group of the formula $$-\overset{+}{N}\underset{R^{18}}{\overset{R^{16}}{\diagdown R^{17}}}$$

in which
R$^{16}$, R$^{17}$ and R$^{18}$ are identical or different and represent a C$_1$–C$_6$-alkyl radical which is optionally substituted by hydroxyl, amino, carboxyl, cyano, nitro, methoxy, methoxycarbonyl, fluorine, chlorine, cyclopropyl, cyclopentyl, cyclohexyl, phenyl or pyridyl, or in which $R^{16}$ has the abovementioned meaning, and $R^{17}$ and $R^{18}$, together, represent the radical of the formula

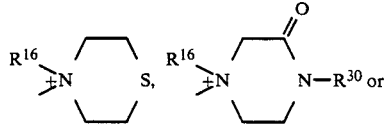

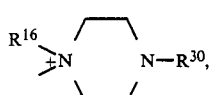

in which $R^{30}$ represents $C_1$-$C_4$-alkyl, carbamoyl, formyl, acetylimido, formylimido, sulphamoyl, $C_1$-$C_4$-hydroxyalkyl, $C_1$-$C_4$-aminoalkyl or $C_1$-$C_4$-alkylsulphonyl, which is optionally substituted by $C_1$-$C_4$-alkyl, $C_1$-$C_4$-hydroxyalkyl, $C_1$-$C_4$-aminoalkyl, carboxyl, methoxycarbonyl, formyl, acetyl, carbamoyl, amino, methylamino, dimethylamino, acetylamino, $C_1$-$C_4$-alkoxy, $C_1$-$C_4$-alkylsulphonyl or dimethylaminosulphonyl, or in which the

group represents a radical of the formula

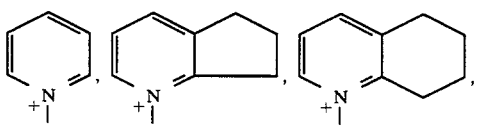

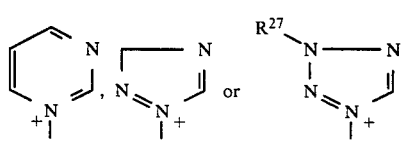

in which $R^{27}$ has the indicated meaning, which is optionally substituted by $C_1$-$C_4$-alkyl, hydroxymethyl, carboxymethyl, methoxycarbonylmethyl, formylmethyl, carbamoylmethyl, methoxymethyl, methylsulphonylmethyl, cyanomethyl, trifluoromethyl, cyclopropyl, $C_1$-$C_4$-alkoxy, amino, methylamino, dimethylamino, acetylamino, formylamino, formylimidoamino, acetylimidoamino, guanidino, carbamoyl, N-methylcarbamoyl, dimethylcarbamoyl, dimethylaminosulphonyl, cyano, hydroxyl, fluorine or chlorine, or (e) represents $C_1$-$C_4$-alkoxycarbonylmethyl, carboxymethyl, hydroxymethyl, or a group of the formula

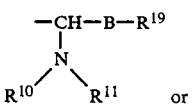

in which $R^{10}$ and $R^{11}$ have the abovementioned meaning,

B denotes a methylene or a carbonyl group and $R^{19}$ denotes hydroxyl, amino, $C_1$-$C_4$-alkylamino, di-$C_1$-$C_4$-alkylamino, phenylamino, benzylamino, acetylamino, benzoylamino or pyridylamino.

3. A compound or salt according to claim 1, in which $R^1$ represents a group of the formula

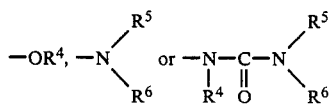

in which $R^4$, $R^5$ and $R^6$ are identical or different and denote hydrogen or phenyl which is optionally substituted by nitro, hydroxyl, fluorine, chlorine, methyl or methoxy, or denote $C_1$-$C_8$-alkyl, $C_2$-$C_4$-alkenyl, cyclopentyl or cyclohexyl, these radicals being optionally up to disubstituted, identically or differently, by methoxy, fluorine, chlorine, bromine, hydroxyl, cyano or phenyl, where this phenyl radical may again carry up to two identical or different substituents from the series comprising methyl, methoxy, nitro, hydroxyl or chlorine, and/or by a group of the formula $-CO_2R^7$ or $-NR^8R^9$, in which $R^7$ represents hydrogen, benzyl, $C_1$-$C_6$-alkyl, or $C_2$-$C_4$-alkenyl, and $R^8$ and $R^9$ are identical or different and represent hydrogen, $C_1$-$_4$-alkyl, benzyl or an amino-protecting group from the series comprising allyl, tert-butoxycarbonyl, benzyl, benzyloxycarbonyl, 4-nitrobenzyl, 4-nitrobenzyloxycarbonyl, 4-methoxybenzyloxycarbonyl, 4-methoxyphenyl, 2,4-dimethoxybenzyl, 2-nitrobenzyloxycarbonyl, tert-butyldimethyl-silyl, methyldiphenylsilyl, trimethylsilyl, acetyl, trifluoroacetyl, formyl or trichloroacetyl, A represents a direct bond or
straight-chain or branched $C_1$-$C_8$-alkylene,
straight-chain or branched $C_2$-$C_8$-alkenylene having up to two double bonds,
cyclopentylene, cyclohexylene,
cyclopentylene-$C_1$-$C_4$-alkylene, cyclohexylene-$C_1$-$C_4$-alkylene, $C_1$-$C_4$-alkylene-cyclopentylene or $C_1$-$C_4$-alkylene-cyclohexylene, $R^2$ (a) represents a group of the formula

in which

R$^{10}$ denotes hydrogen, C$_1$-C$_6$-alkyl, phenyl or benzyl,

R$^{11}$ denotes hydrogen, C$_1$-C$_6$-alkyl, phenyl, benzyl, C$_1$-C$_4$-alkylsulphonyl, benzylsulphonyl, an amino-protecting group from the series comprising allyl, tert-butoxycarbonyl, benzyl, benzyloxycarbonyl, 4-nitrobenzyl, 4-nitrobenzyloxycarbonyl, 4-methoxybenzyloxycarbonyl, formyl, acetyl, trichloroacetyl, 4-methoxyphenyl, 4-methoxybenzyl, 2,4-dimethoxybenzyl, 2-nitrobenzyloxycarbonyl, tert-butyl-dimethylsilyl, methyldiphenylsilyl, trimethylsilyl or trifluoroacetyl, or a group of the formula

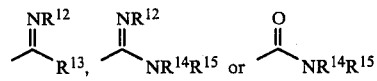

in which

R$^{12}$, R$^{13}$, R$^{14}$ and R$^{15}$ are identical or different and represent hydrogen, C$_1$-C$_6$-alkyl, phenyl or benzyl,

R$^2$ (b) represents phenyl which is optionally substituted by fluorine, chlorine, hydroxyl, methoxy, cyano, trifluoromethyl, carbamoyl, sulphamoyl, C$_1$-C$_4$-alkyl cyanomethyl, carboxymethyl, hydroxymethyl, aminomethyl or a group of the formula

in which

R$^{10}$ and R$^{11}$ have the abovementioned meaning, or

R$^2$ (c) represents a radical of the formula

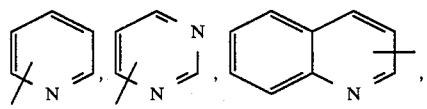

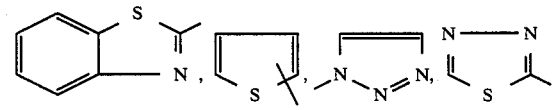

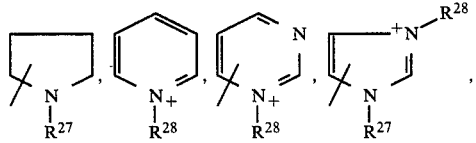

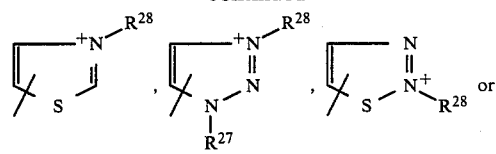

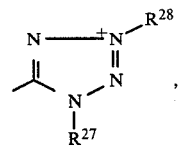

in which

R$^{26}$ denotes hydrogen, C$_1$-C$_4$-alkyl or phenyl,

R$^{27}$ denotes C$_1$-C$_4$-alkyl, C$_1$-C$_4$-alkylcarbonyl or a group of the formula

in which

R$^{12}$ and R$^{13}$ are identical or different and have the abovementioned meaning, and R$^{28}$ denotes C$_1$-C$_4$-alkyl or phenyl, which is optionally substituted by methoxy, amino, methylamino, dimethylamino, acetylamino, formylamino, formylimidoamino, acetylimidoamino, guanidino, fluorine, chlorine, carbamoyl, sulphamoyl, C$_1$-C$_4$-alkyl, amino-C$_1$-C$_2$-alkyl, methylamino-C$_1$-C$_2$-alkyl, dimethylamino-C$_1$-C$_2$-alkyl, hydroxy-C$_1$-C$_2$-alkyl or carbamoyl-C$_1$-C$_2$-alkyl, or

R$^2$ (d) represents a group of the formula

in which

R$^{16}$, R$^{17}$ and R$^{18}$ are identical or different and represent a C$_1$-C$_6$-alkyl radical which is optionally substituted by hydroxyl, amino, carboxyl, cyano, nitro, methoxy, methoxycarbonyl, fluorine, chlorine, cyclopropyl, cyclopentyl, cyclohexyl, phenyl or pyridyl, or in which R$^{16}$ has the abovementioned meaning, and R$^{17}$ and R$^{18}$, together, represent the radical of the formula

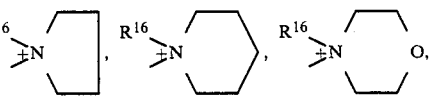

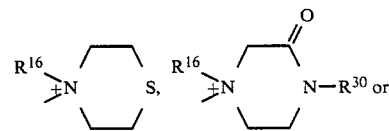

-continued

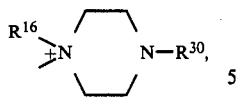

in which
R$^{30}$ represents C$_1$–C$_4$-alkyl, carbamoyl, formyl, acetylimido, formylimido, sulphamoyl, C$_1$–C$_4$-hydroxyalkyl, C$_1$–C$_4$-aminoalkyl or C$_1$–C$_4$-alkylsulphonyl,
which is optionally substituted by C$_1$–C$_4$-alkyl, C$_1$–C$_4$-hydroxyalkyl, C$_1$–C$_4$-aminoalkyl, carboxyl, methoxycarbonyl, formyl, acetyl, carbamoyl, amino, methylamino, dimethylamino, acetylamino, C$_1$–C$_4$-alkoxy, C$_1$–C$_4$-alkylsulphonyl or dimethylaminosulphonyl, or in which the

group represents a radical of the formula

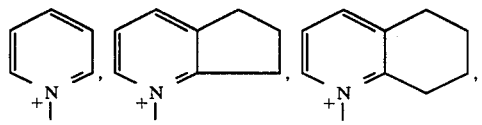

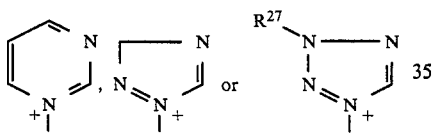

in which
R$^{27}$ has the indicated meaning,
which is optionally substituted by C$_1$–C$_4$-alkyl, hydroxymethyl, carboxymethyl, methoxycarbonylmethyl, formylmethyl, carbamoylmethyl, methoxymethyl, methylsulphonylmethyl, cyanomethyl, trifluoromethyl, cyclopropyl, C$_1$–C$_4$-alkoxy, amino, methylamino, dimethylamino, acetylamino, formylamino, formylimidoamino, acetylimidoamino, guanidino, carbamoyl, N-methylcarbamoyl, dimethylcarbamoyl, dimethylaminosulphonyl, cyano, hydroxyl, fluorine or chlorine, or R$^2$
(e) represents C$_1$–C$_4$-alkoxycarbonylmethyl, carobxymethyl, hydroxymethyl or a group of the formula

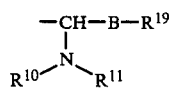

in which
R$^{10}$ and R$^{11}$ have the abovementioned meaning,
B denotes a methylene or carbonyl group and
R$^{19}$ denotes hydroxyl, amino, C$_1$–C$_4$-alkylamino, di-C$_1$–C$_4$-alkylamino, phenylamino, benzylamino, acetylamino or pyridylamino, and R$^3$ represents a carboxyl group of the formula COOR$^{20}$, in which
R$^{20}$ represents hydrogen, methyl, ethyl, tert-butyl, 2,2,2-trichloroethyl, allyl, acetylmethyl, 4-nitrobenzyl, 2-nitrobenzyl, 4-methoxybenzyl, benzyl, trimethylsilylethyl or a radical of the formula

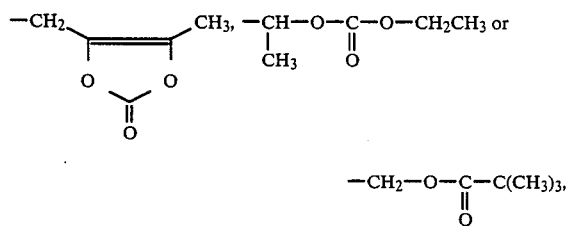

or
R$^3$ represents COO$^-$ if R$^2$ represents a radical having a positive charge.
4. A compound or salt according to claim 1, in which
R$^1$ represents a group of the formula

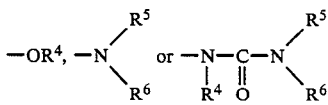

in which
R$^4$, R$^5$ and R$^6$ are identical or different and denote hydrogen, allyl or straight-chain or branched C$_1$–C$_4$-alkyl, cyclopentyl or cyclohexyl, the alkyl radical being optionally substituted by chlorine, phenyl, nitrophenyl, amino, tert-butyloxycarbonylamino, benzyloxycarbonylamino, acetylamino and/or a group of the formula —COOR$^7$,
in which
R$^7$ represents hydrogen, C$_1$–C$_4$-alkyl, allyl or 4-nitrobenzyl,
A represents a direct bond or
represents straight-chain or branched C$_1$–C$_4$-alkylene or C$_2$–C$_4$-alkenylene, or
represents cyclohexylene, cyclopentylene, cyclopentylenemethyl, cyclohexylenemethyl, methylenecyclopentylene or methylenecyclohexylene, R$^2$
(a) represents a group of the formula

in which
R$^{10}$ denotes hydrogen, C$_1$–C$_4$-alkyl or phenyl,
R$^{11}$ denotes hydrogen, C$_1$–C$_4$-alkyl, phenyl, tert-butoxycarbonyl, benzyloxycarbonyl, acetyl, ethylcarbonyl or a group of the formula

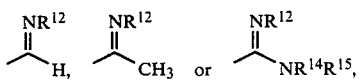

in which
R$^{12}$, R$^{14}$ and R$^{15}$ are identical or different and represent hydrogen, methyl or phenyl, or $R^2$
(b) represents phenyl which is optionally substituted by hydroxyl, methyl, methoxy, hydroxymethyl amino, formylimidoamino, acetylimidoamino, guanidino or aminomethyl, $R^2$
(c) represents a group of the formula

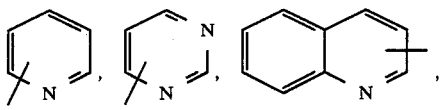

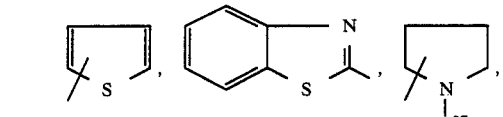

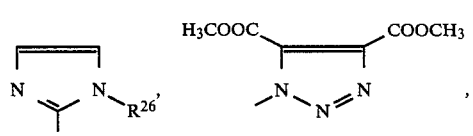

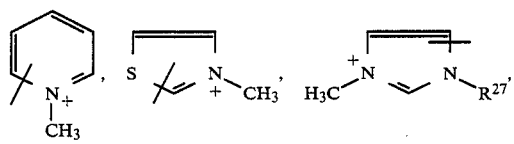

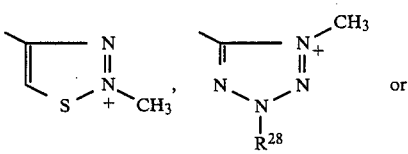

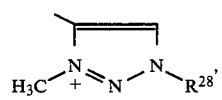

in which
$R^{26}$ represents hydrogen, methyl or phenyl,
$R^{27}$ represents acetyl, formylimido or acetylimido, and
$R^{28}$ represents methyl or phenyl,
which is optionally substituted by methyl, amino, formylimidoamino, acetylimidoamino, guanidino or aminomethyl, $R^2$
(d) represents a group of the formula

in which
$R^{16}$, $R^{17}$ and $R^{18}$ are identical or different and denote a $C_1$-$C_4$-alkyl radical which is optionally substituted by hydroxyl, amino, phenyl or pyridyl, or
$R^{16}$ denotes methyl or ethyl, and
$R^{17}$ and $R^{18}$, together, represent a group of the formula

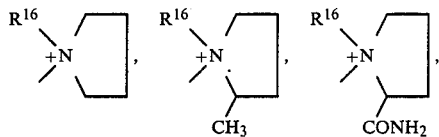

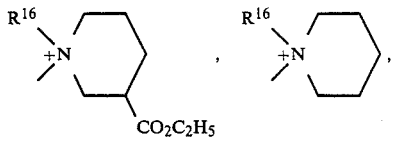

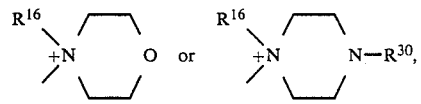

in which
$R^{30}$ represents $C_1$-$C_4$-alkyl, carbamoyl, formyl, $C_1$-$C_4$-hydroxyalkyl or methylsulphonyl, or the

group represents a group of the formula

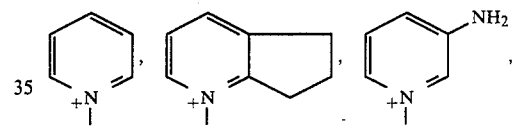

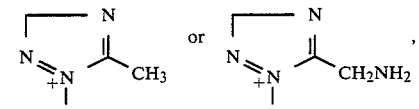

$R^2$
(e) represents carboxymethyl or a group of the formula

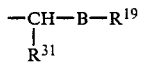

in which
B denotes a methylene or carbonyl group,
$R^{19}$ denotes hydroxyl, amino, methylamino, dimethylamino, acetylamino or pyridylamino, and
$R^{31}$ denotes amino, methylamino, dimethylamino or acetylamino, and
$R^3$ represents a carboxyl group of the formula $COOR^{20}$, in which
$R^{20}$ denotes hydrogen, allyl, 4-nitrobenzyl or 4-methoxybenzyl, or
represents $COO^-$ if $R^2$ represents a radical having a positive charge.

5. A compound or salt according to claim 1, in which
$R^1$ represents a group of the formula —$OCH_3$, —$OC_2H_5$, —$OC_3H_7$, —$OCH(CH_3)_2$, —$OC_4H_9$, —OC(CH₃)₃, —O—CH₂—CH=CH₂, —O—CH₂—C₆H₅,
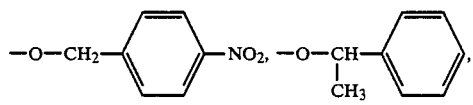
—NH₂, —NHCH₃, —N(CH₃)₂, —NHC₂H₅, —N(C₂H₅)₂, —NHC₃H₇, —N(C₃H₇)₂, —NHCH(CH₃)₂,
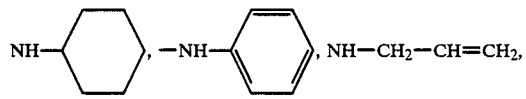, NH—CH₂—CH=CH₂,
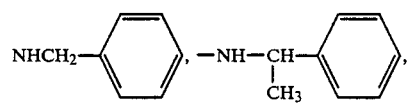
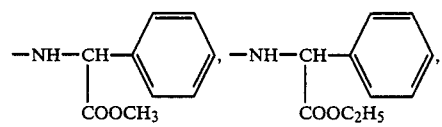
—NH—CO—NH₂, —NH—CO—NHCH₃, —NH—CO—N(CH₃)₂,
—N(CH₃)—CO—NH₂, —N(CH₃)—CO—NHCH₃, —N(CH₃)—CO—N(CH₃)₂,
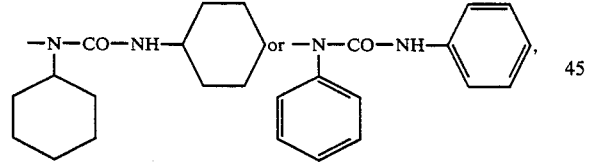
the AR² group represents a radical of the formula
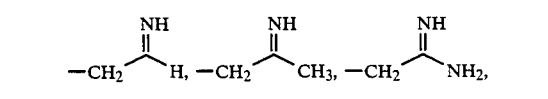
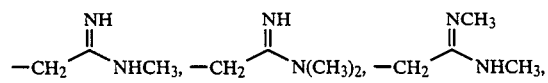
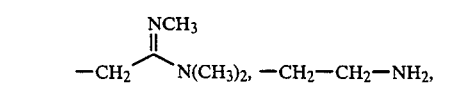
—CH₂—CH₂—NHCH₃, —CH₂—CH₂—N(CH₃)₂,
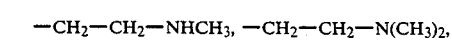
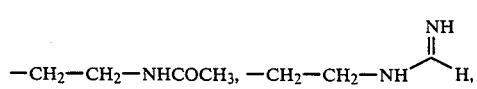
-continued
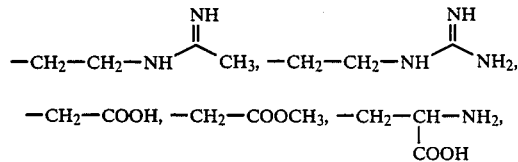
—CH₂—COOH, —CH₂—COOCH₃, —CH₂—CH(NH₂)—COOH,
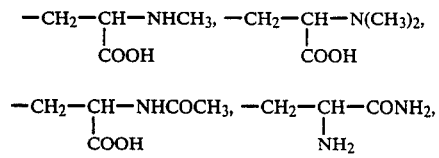
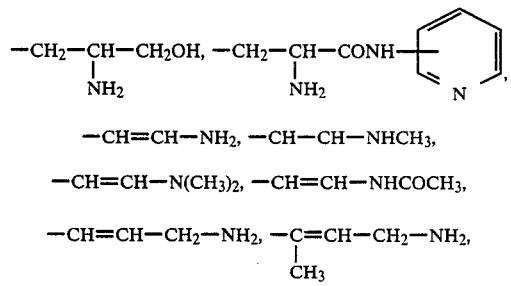
—CH=CH—NH₂, —CH—CH—NHCH₃,
—CH=CH—N(CH₃)₂, —CH=CH—NHCOCH₃,
—CH=CH—CH₂—NH₂, —C(CH₃)=CH—CH₂—NH₂,
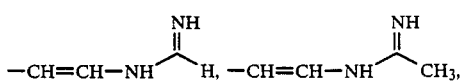
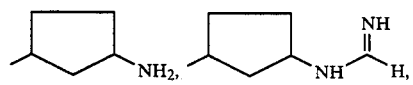
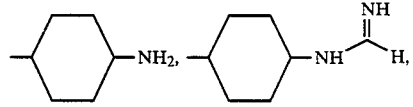
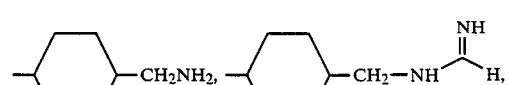
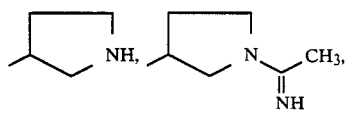
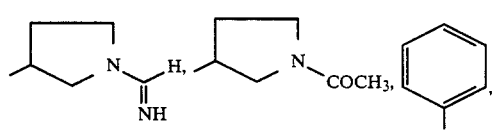
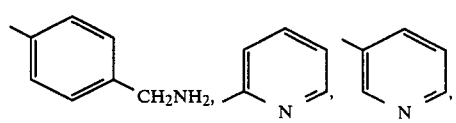
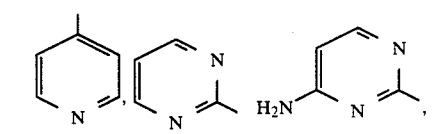

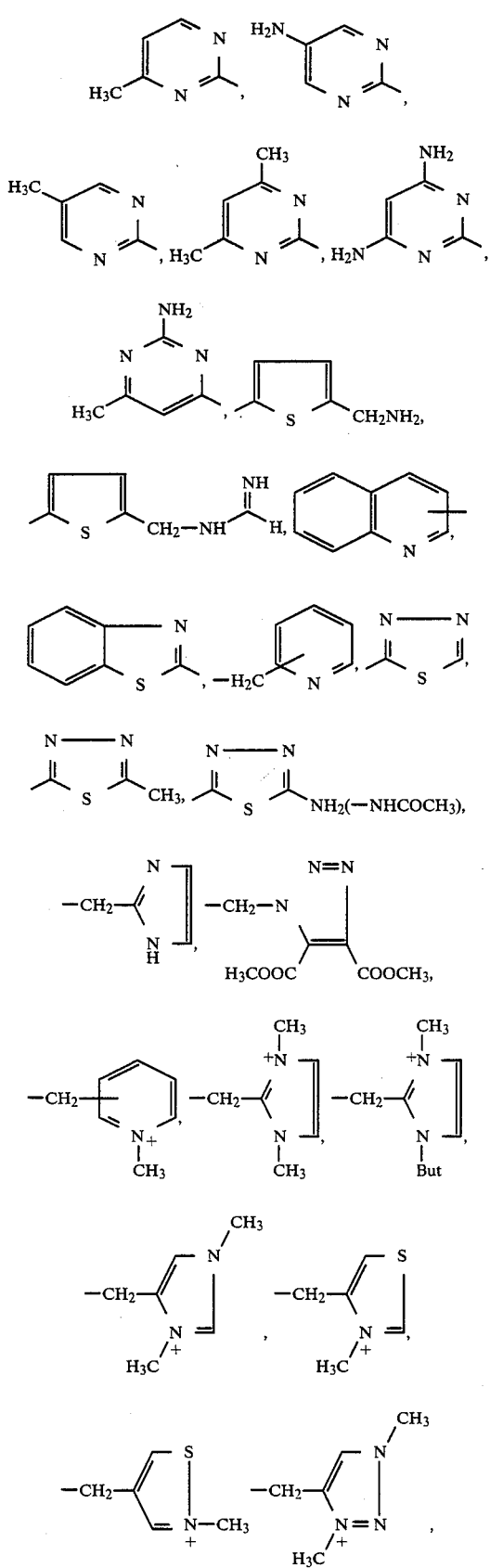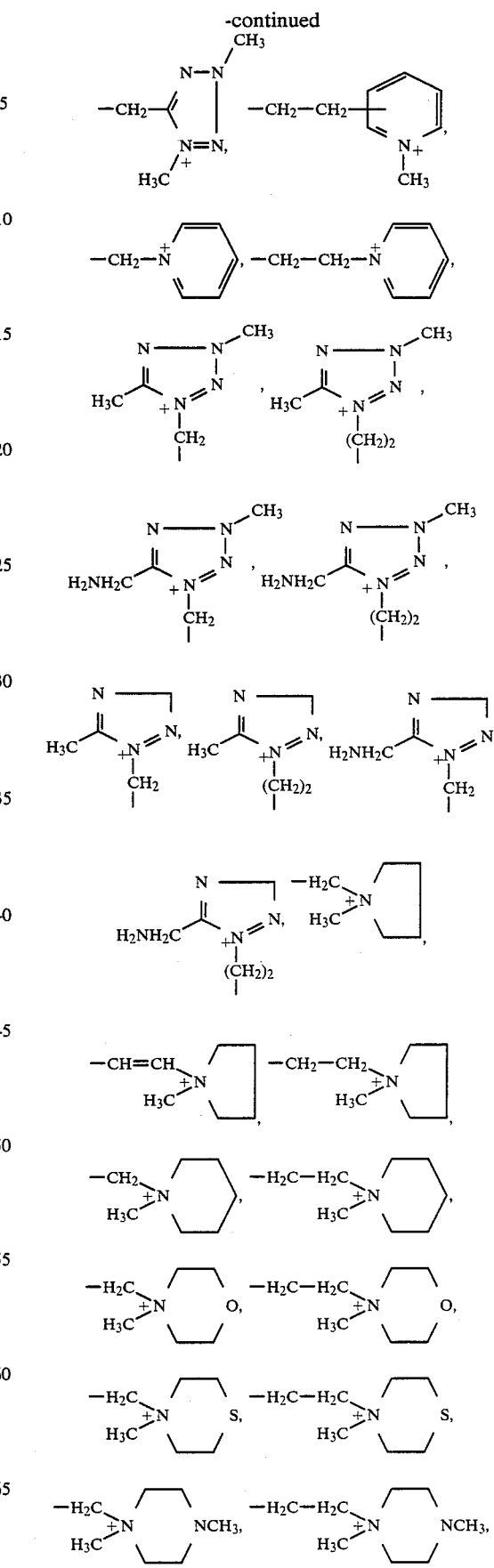

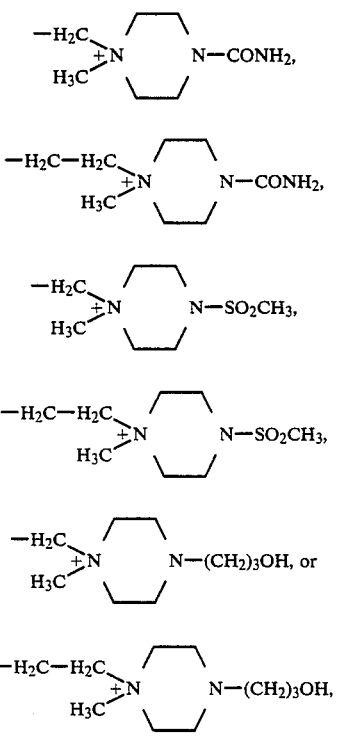

and

R³ represents a carboxyl group COOR²⁰, in which
R²⁰ denotes hydrogen, allyl, 4-nitrobenzyl or 4-methoxybenzyl, or represents COO⁻ if the AR² group represents a positively charged radical.

6. A compound according to claim 1, wherein such compound is (2S, 5R, 6S)-3,7-dioxo-6-[(1S)-1-hydroxy-1-methoxycarbonyl]methyl-2-p-nitrobenzyloxycarbonyl-1-azabicyclo[3.2.0]heptane of the formula

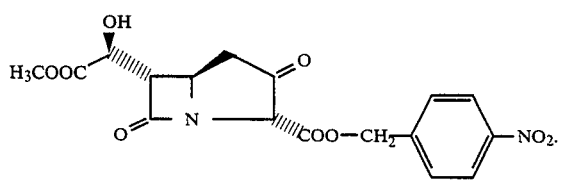

7. A compound according to claim 1, wherein such compound is p-nitrobenzyl (5R,6S)-6-[(1S)-1-hydroxy-1-methoxycarbonyl]methyl-7-oxo-3-(4-pyridinylthio)-1-azabicyclo[3.2.0]hept-2-en-2-carboxylate of the formula

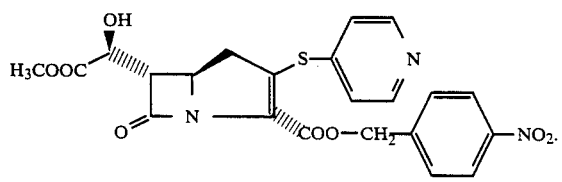

8. A compound according to claim 1, wherein such compound is sodium (5R,6S)-6-[(1S)-1-hydroxy-1-methoxycarbonyl]methyl-7-oxo-3-(4-pyridinylthio)-1-azabicyclo[3.2.0]hept-2-en-carboxylate of the formula

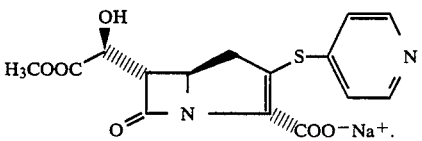

9. An antibiotic composition comprising a diluent and an antibiotically effective amount of a substituted 6-hydroxymethylcarbapenem antibiotic of the formula

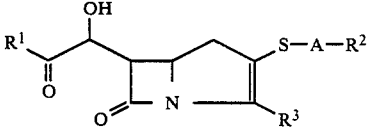

in which

R¹ represents a group of the formula —OR⁴,

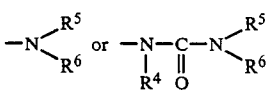

in which

R⁴, R⁵ and R⁶ are identical or different and denote hydrogen or $C_6$–$C_{12}$-aryl which is optionally up to trisubstituted, identically or differently, by nitro, hydroxyl, cyano, halogen, trifluoromethyl, trifluoromethoxy, $C_1$–$C_6$-alkyl or $C_1$–$C_6$-alkoxy, or denote $C_1$–$C_{12}$-alkyl, $C_2$–$C_{12}$-alkenyl or $C_3$–$C_8$-cycloalkyl, these radicals being optionally polysubstituted, identically or differently by $C_1$–$C_4$-alkoxy, halogen, hydroxyl, cyano and/or phenyl, where this phenyl radical may again carry up to three identical or different substituents from the series comprising $C_1$–$C_4$-alkyl, $C_1$–$C_4$-alkoxy, nitro, cyano, hydroxyl or halogen, and/or —NR⁸R⁹, in which R⁷ represents hydrogen, phenyl, benzyl, $C_1$–$C_8$-alkyl or $C_2$–$C_6$-alkenyl, and R⁸ and R⁹ are identical or different and represent hydrogen, $C_1$–$C_6$-alkyl, phenyl, or benzyl, A represents a direct bond or represents a $C_1$–$C_{12}$-alkylene or $C_2$–$C_{12}$-alkenylene chain which is optionally interrupted in the chain by an oxygen atom or a sulphur atom, or represents cycloalkylene having 3 to 8 carbon atoms, cycloalkylene-alkylene or alkylenecycloalkylene having 3 to 8 carbon atoms in the cycloalkylene part and 1 to 8 carbon atoms in the alkylene chain, or represents alkylene-cycloalkylene-alkylene having 3 to 8 carbon atoms in the cycloalkyl part and 1 to 8 carbon atoms in each alkylene part,

R²

(a) represents a group of the formula

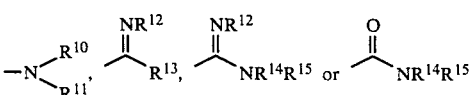

in which $R^{10}$ denotes hydrogen, $C_1$–$C_{10}$-alkyl, $C_6$–$C_{12}$-aryl or $C_7$–$C_{14}$-aralkyl, $R^{11}$ represents hydrogen, $C_1$–$C_{10}$-alkyl, $C_6$–$C_{12}$-aryl, $C_7$–$C_{14}$-aralkyl, $C_1$–$C_{10}$-alkylsulphonyl, $C_6$–$C_{12}$-arylsulphonyl, $C_7$–$C_{14}$-aralkylsulphonyl, or a group of the formula

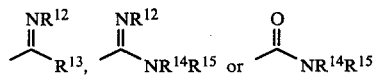

and $R^{12}$, $R^{13}$, $R^{14}$ and $R^{15}$ are identical or different and denote hydrogen, $C_1$–$C_{10}$-alkyl, $C_6$–$C_{12}$ aryl or $C_7$–$C_{14}$-aralkyl, or (b) represents a $C_6$–$C_{12}$-aryl radical which is optionally up to trisubstituted, identically or differently, or (c) represents a radical of the formula

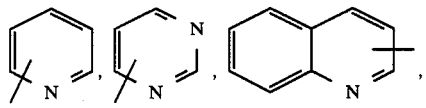

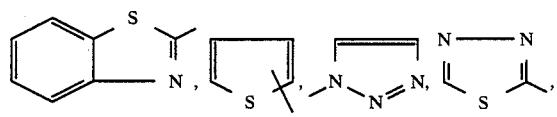

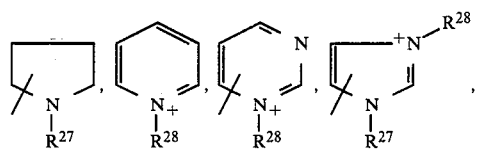

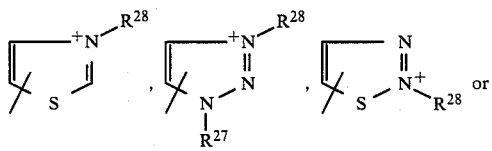

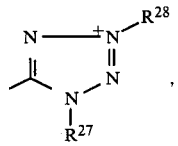

in which $R^{26}$ denotes hydrogen, $C_1$–$C_4$-alkyl or phenyl, $R^{27}$ denotes $C_1$–$C_4$-alkyl, $C_1$–$C_4$-alkylcarbonyl or a group of the formula

in which $R^{12}$ and $R^{13}$ are identical or different and have the abovementioned meaning, and $R^{28}$ denotes $C_1$–$C_4$-alkyl or phenyl, which is optionally substituted by methoxy, amino, methylamino, dimethylamino, acetylamino, formylamino, formylimidoamino, acetylimidoamino, guanidino, fluorine, chlorine, carbamoyl, sulphamoyl, $C_1$–$C_4$-alkyl, amino-$C_1$–$C_2$-alkyl, methylamino-$C_1$–$C_2$-alkyl, dimethylamino-$C_1$–$C_2$-alkyl, hydroxy-$C_1$–$C_2$-alkyl or carbamoyl-$C_1$–$C_2$-alkyl, or (d) represents a group of the formula

in which $R^{16}$, $R^{17}$ and $R^{18}$ are identical or different and represent a $C_1$–$C_6$-alkyl radical which is optionally substituted by hydroxyl, amino, carboxyl, cyano, nitro, methoxy, methoxycarbonyl, fluorine, chlorine, cyclopropyl, cyclopentyl, cyclohexyl, phenyl or pyridyl, or in which $R^{16}$ has the abovementioned meaning, and $R^{17}$ and $R^{18}$, together, represent the radical of the formula

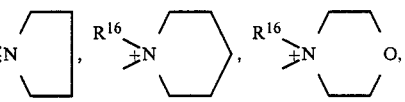

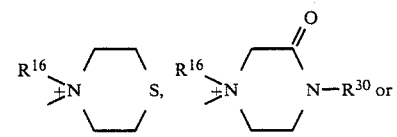

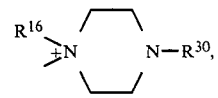

in which $R^{30}$ represents $C_1$–$C_4$-alkyl, carbamoyl, formyl, acetylimido, formylimido, sulphamoyl, $C_1$–$C_4$-hydroxyalkyl, $C_1$–$C_4$-aminoalkyl or $C_1$–$C_4$-alkylsulphonyl, which is optionally substituted by $C_1$–$C_4$-alkyl, $C_1$–$C_4$-hydroxyalkyl, $C_1$–$C_4$-aminoalkyl, carboxyl, methoxycarbonyl, formyl, acetyl, carbamoyl, amino, methylamino, dimethylamino, acetylamino, $C_1$–$C_4$-alkoxy, $C_1$–$C_4$-alkylsulphonyl or dimethylaminosulphonyl, or in which the

group represents a radical of the formula

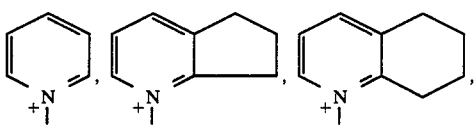

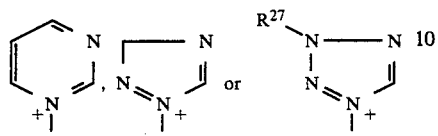

in which R²⁷ has the indicated meaning, which is optionally substituted by $C_1$-$C_4$-alkyl, hydroxymethyl, carboxymethyl, methoxycarbonylmethyl, formylmethyl, carbamoylmethyl, methoxymethyl, methylsulphonylmethyl, cyanomethyl, trifluoromethyl, cyclopropyl, $C_1$-$C_4$-alkoxy, amino, methylamino, dimethylamino, acetylamino, formylamino, formylimidoamino, acetylimidoamino, guanidino, carbamoyl, N-methylcarbamoyl, dimethylcarbamoyl, dimethylaminosulphonyl, cyano, hydroxyl, fluorine or chlorine, or (e) represents $C_1$-$C_8$-alkoxycarbonylmethyl, carboxymethyl, hydroxymethyl or a group of the formula

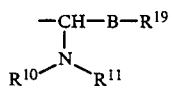

in which $R^{10}$ and $R^{11}$ have the abovementioned meaning,

B denotes a methylene or carbonyl group, and $R^{19}$ denotes hydroxyl, amino, $C_1$-$C_6$-alkylamino, di-$C_1$-$C_6$-alkylamino, $C_6$-$C_{12}$-arylamino, $C_7$-$C_{14}$-aralkylamino, $C_2$-$C_7$-acylamino or pyridylamino and $R^3$ represents a carboxyl group of the formula $COOR^{20}$, in which $R^{20}$ denotes hydrogen, or an ester radical which can be cleaved off in vivo, or represents COO⁻ if $R^2$ represents a radical having positive charge, or a salt thereof.

10. A unit does of a composition according to claim 9 in the form of a tablet, capsule or ampule.

11. A method of combating bacterial infection in a patient, which comprises administering to a patient an antibiotically effective amount of a substituted 6-hydroxymethyl-carbapenem antibiotic of the formula

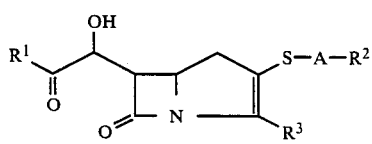

in which $R^1$ represents a group of the formula —OR⁴,

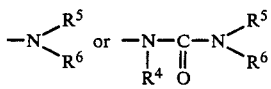

in which $R^4$, $R^5$ and $R^6$ are identical or different and denote hydrogen or $C_6$-$C_{12}$-aryl which is optionally up to trisubstituted, identically or differently, by nitro, hydroxyl, cyano, halogen, trifluoromethyl, trifluoromethoxy, $C_1$-$C_6$-alkyl or $C_1$-$C_6$-alkoxy, or denote $C_1$-$C_{12}$-alkyl, $C_2$-$C_{12}$-alkenyl or $C_3$-$C_8$-cycloalkyl, these radicals being optionally polysubstituted, identically or differently by $C_1$-$C_4$-alkoxy, halogen, hydroxyl, cyano and/or phenyl, where this phenyl radical may again carry up to three identical or different substituents from the series comprising $C_1$-$C_4$-alkyl, $C_1$-$C_4$-alkoxy, nitro, cyano, hydroxyl or halogen, and/or by a group of the formula —$CO_2R^7$ and/or —$NR^8R^9$, in which $R^7$ represents hydrogen, phenyl, benzyl, $C_1$-$C_8$-alkyl or $C_2$-$C_6$-alkenyl, and $R^8$ and $R^9$ are identical or different and represent hydrogen, $C_1$-$C_6$-alkyl, phenyl, or benzyl, A represents a direct bond or represents a $C_1$-$C_{12}$-alkylene or $C_2$-$C_{12}$-alkenylene chain which is optionally interrupted in the chain by an oxygen atom or a sulphur atom, or represents cycloalkylene having 3 to 8 carbon atoms, cycloalkylene-alkylene or alkylenecycloalkylene having 3 to 8 carbon atoms in the cycloalkylene part and 1 to 8 carbon atoms in the alkylene chain, or represents alkylene-cycloalkylene-alkylene having 3 to 8 carbon atoms in the cycloalkyl part and 1 to 8 carbon atoms in each alkylene part, $R^2$ (a) represents a group of the formula

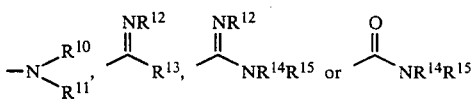

in which $R^{10}$ denotes hydrogen, $C_1$-$C_{10}$-alkyl, $C_6$-$C_{12}$-aryl or $C_7$-$C_{14}$-aralkyl, $R^{11}$ represents hydrogen, $C_1$-$C_{10}$-alkyl, $C_6$-$C_{12}$-aryl, $C_7$-$C_{14}$-aralkyl, $C_1$-$C_{10}$-alkylsulphonyl, $C_6$-$C_{12}$-arylsulphonyl, $C_7$-$C_{14}$-aralkylsulphonyl, or a group of the formula

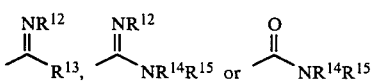

and $R^{12}$, $R^{13}$, $R^{14}$ and $R^{15}$ are identical or different and denote hydrogen, $C_1$-$C_{10}$-alkyl, $C_6$-$C_{12}$ aryl or $C_7$-$C_{14}$-aralkyl, or (b) represents a $C_6$-$C_{12}$-aryl radical which is optionally up to trisubstituted, identically or differently, or (c) represents a radical of the formula

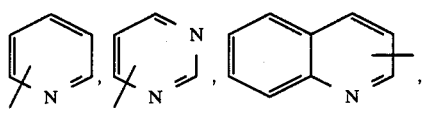

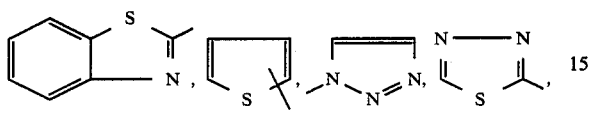

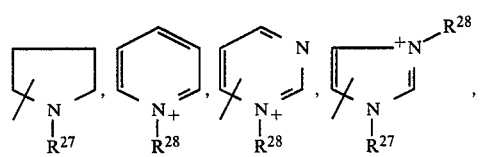

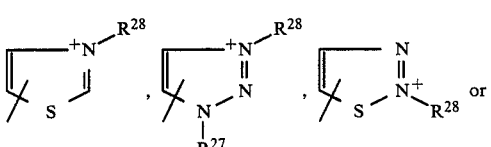

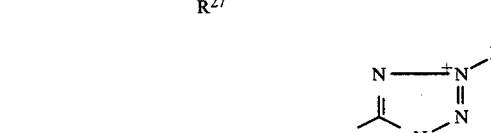
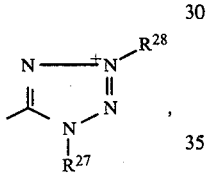

in which $R^{26}$ denotes hydrogen, $C_1$-$C_4$-alkyl or phenyl, $R^{27}$ denotes $C_1$-$C_4$-alkyl, $C_1$-$C_4$-alkylcarbonyl or a group of the formula

in which $R^{12}$ and $R^{13}$ are identical or different and have the abovementioned meaning, and $R^{28}$ denotes $C_1$-$C_4$-alkyl or phenyl, which is optionally substituted by methoxy, amino, methylamino, dimethylamino, acetylamino, formylamino, formylimidoamino, acetylimidoamino, guanidino, fluorine, chlorine, carbamoyl, sulphamoyl, $C_1$-$C_4$-alkyl, amino-$C_1$-$C_2$-alkyl, methylamino-$C_1$-$C_2$-alkyl, dimethylamino-$C_1$-$C_2$-alkyl, hydroxy-$C_1$-$C_2$-alkyl or carbamoyl-$C_1$-$C_2$-alkyl, or (d) represents a group of the formula

in which $R^{16}$, $R^{17}$ and $R^{18}$ are identical or different and represent a $C_1$-$C_6$-alkyl radical which is optionally substituted by hydroxyl, amino, carboxyl, cyano, nitro, methoxy, methoxycarbonyl, fluorine, chlorine, cyclopropyl, cyclopentyl, cyclohexyl, phenyl or pyridyl, or in which $R^{16}$ has the abovementioned meaning, and $R^{17}$ and $R^{18}$, together, represent the radical of the formula

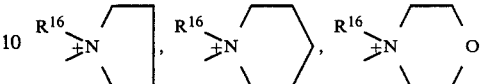

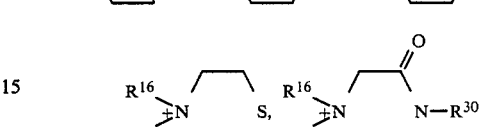

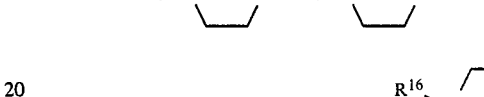

in which $R^{30}$ represents $C_1$-$C_4$-alkyl, carbamoyl, formyl, acetylimido, formylimido, sulphamoyl, $C_1$-$C_4$-hydroxyalkyl, $C_1$-$C_4$-aminoalkyl or $C_1$-$C_4$-alkylsulphonyl, which is optionally substituted by $C_1$-$C_4$-alkyl, $C_1$-$C_4$-hydroxyalkyl, $C_1$-$C_4$-aminoalkyl, carboxyl, methoxycarbonyl, formyl, acetyl, carbamoyl, amino, methylamino, dimethylamino, acetylamino, $C_1$-$C_4$-alkoxy, $C_1$-$C_4$-alkylsulphonyl or dimethylaminosulphonyl, or in which the

group represents a radical of the formula

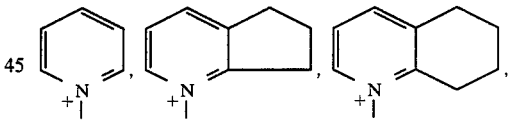

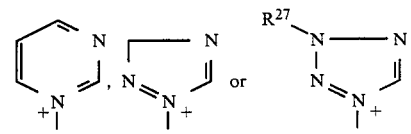

in which $R^{27}$ has the indicated meaning, which is optionally substituted by $C_1$-$C_4$-alkyl, hydroxymethyl, carboxylmethyl, methoxycarbonylmethyl, formylmethyl, carbamoylmethyl, methoxmethyl, methylsulphonylmethyl, cyanomethyl, trifluoromethyl, cyclopropyl, $C_1$-$C_4$-alkoxy, amino, methylamino, dimethylamino, acetylamino, formylamino, formylimidoamino, acetylimidoamino, guanidino, carbamoyl, N-methylcarbamoyl, dimethylcarbamoyl, dimethylaminosulphonyl, cyano, hydroxyl, fluorine or chlorine, or (e) represents $C_1$–$C_8$-alkoxycarbonylmethyl, carboxymethyl, hydroxymethyl or a group of the formula

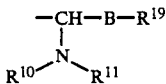

in which $R^{10}$ and $R^{11}$ have the abovementioned meaning,

B denotes a methylene or carbonyl group, and $R^{19}$ denotes hydroxyl, amino, $C_1$–$C_6$-alkylamino, di-$C_1$–$C_6$-alkylamino, $C_6$–$C_{12}$-arylamino, $C_7$–$C_{14}$-aralkylamino, $C_2$–$C_7$-acylamino or pyridylamino and $R^3$ represents a carboxyl group of the formula $COOR^{20}$, in which $R^{20}$ denotes hydrogen, or an ester radical which can be cleaved off in vivo, or represents $COO^-$ if $R^2$ represents a radical having positive charge, or a salt thereof.

12. The method according to claim 11, wherein such compound is (2S, 5R, 6S)-3,7-dioxo-6-[(1S)-1-hydroxy-1-methoxycarbonyl]methyl-2-p-nitrobenzyloxycarbonyl-1-azabicyclo-[3.2.0]heptane, p-nitrobenzyl (5R,6S)-6-[(1S)-1-hydroxy-1-methoxycarbonyl]methyl-7-oxo-3-(4-pyridinylthio)-1-azabicyclo[3.2.0]hept-2-en-2-carboxylate or sodium (5R,6S)-6-[(1S)-1-hydroxy-1-methoxycarbonyl]methyl-7-oxo-3-(4-pyridinylthio)-1-azabicyclo[3.2.0]hept-2-en-carboxylate.

* * * * *